US012806603B2

(12) United States Patent
Hermans et al.

(10) Patent No.: US 12,806,603 B2
(45) Date of Patent: Nov. 24, 2026

(54) CARBON-SUPPORTED BORON CATALYSTS FOR OXIDATIVE DEHYDROGENATION OF ALKANES

(71) Applicant: Wisconsin Alumni Research Foundation, Madison, WI (US)

(72) Inventors: Ive Hermans, Middleton, WI (US); Lesli Mark, Madison, WI (US); William Mcdermott, Madison, WI (US); Theodore Agbi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 521 days.

(21) Appl. No.: 18/263,966

(22) PCT Filed: Feb. 2, 2022

(86) PCT No.: PCT/US2022/014872

§ 371 (c)(1),
(2) Date: Aug. 2, 2023

(87) PCT Pub. No.: WO2022/169817

PCT Pub. Date: Aug. 11, 2022

(65) Prior Publication Data

US 2024/0123428 A1 Apr. 18, 2024

Related U.S. Application Data

(60) Provisional application No. 63/144,561, filed on Feb. 2, 2021.

(51) Int. Cl.

| | |
|---|---|
| ***B01J 21/18*** | (2006.01) |
| ***B01J 6/00*** | (2006.01) |
| ***B01J 21/02*** | (2006.01) |
| ***B01J 37/02*** | (2006.01) |
| ***B01J 37/08*** | (2006.01) |
| ***B01J 37/14*** | (2006.01) |
| ***C07C 5/333*** | (2006.01) |

(52) U.S. Cl.

CPC ............... *B01J 21/18* (2013.01); *B01J 6/001* (2013.01); *B01J 21/02* (2013.01); *B01J 37/0201* (2013.01); *B01J 37/08* (2013.01); *B01J 37/14* (2013.01); *C07C 5/333* (2013.01); *C07C 2521/02* (2013.01); *C07C 2521/18* (2013.01)

(58) Field of Classification Search

CPC ... B01J 21/18; B01J 6/001; B01J 21/02; B01J 37/0201; B01J 37/08; B01J 37/14; C07C 5/333; C07C 2521/02; C07C 2521/18

USPC ......... 502/180, 182, 202; 423/460; 585/654, 585/440, 601

See application file for complete search history.

(56) References Cited

U.S. PATENT DOCUMENTS

| | | | | |
|---|---|---|---|---|
| 4,371,454 | A | 2/1983 | Hisatsugu et al. | |
| 5,449,529 | A * | 9/1995 | Okada | C04B 35/645 442/127 |
| 10,011,540 | B2 | 7/2018 | Hermans et al. | |
| 10,125,059 | B2 | 11/2018 | Hermans et al. | |
| 10,407,364 | B2 | 9/2019 | Hermans et al. | |
| 2018/0069247 | A1 * | 3/2018 | Iijima | H01M 4/96 |

FOREIGN PATENT DOCUMENTS

| | | | | |
|---|---|---|---|---|
| CN | 108484349 | A * | 9/2018 | B01J 21/02 |
| CN | 111211310 | A | 5/2020 | |
| CN | 111686766 | A | 9/2020 | |
| CN | 107866239 | B | 10/2020 | |
| CN | 110302769 | B | 12/2020 | |
| JP | 2022099330 | A * | 7/2022 | C01B 32/00 |

OTHER PUBLICATIONS

Lesli O. Mark, et al., “Highly Selective Carbon-Supported Boron for Oxidative Dehydrogenation of Propane.” ChemCatChem, vol. 13, pp. 3611-3618. (Year: 2021).*

Chunyu Xin et al., “Boron-doped nanocarbon catalysts for oxidative dehydrogenation of ethane to ethylene.” Carbon 193, pp. 381-393. (Year: 2022).*

Wen-Duo Lu et al., “Supported boron-based catalysts for oxidative dehydrogenation of light alkanes to olefins.” Catalysis Science and Technology 13, pp. 1696-1707. (Year: 2023).*

Tingcong Wang et al., “Effect of boron species on carbon surface on oxidative dehydrogenation of propane.” Chinese Journal of Chemical Engineering 62, pp. 310-317. (Year: 2023).*

Mawhinney, D.B. and Yates Jr. Jt. Carbon, 2001, 39, 1167-1173.

Mckee, D. W.; Spiro, C. L.; Lamby, E. J. The Effects of Boron Additives on the Oxidation Behavior of Carbons. Carbon N Y 1984, 22 (6), 507-511. https://doi.org/10.1 OI 6/0008-6223(84)90083-6.

Medek A., J. S. Harwood, L. Frydman, J. Am. Chem. Soc. 1995, 117, 12779-12787.

Mestl G., N. I. Maksimova, N. Keller, V. V. Roddatis, R. Schlogl, Angew. Chem. Int. Ed. 2001, 40, 2066-2068.

Nikolla E., A. Holewinski, J. Schwank, S. Linic, J. Am. Chem. Soc. 2006, 128, 11354-11355.

Nozawa, S et al., “Effect of Dissolved Silica on Immobilization of Boron by Magnesium Oxide”, Minerals, vol. 8, No. 76, Feb. 24, 2018, doi:10.3390/min8020076.

Peak, D.; Luther, G. W.; Sparks, D. L. ATR-FTIR Spectroscopic Studies of Boric Acid Adsorption on Hydrous Ferric Oxide. Geochim. Cosmochim. Acta 2003, 67 (14), 2551-2560. https://doi.org/10.1016/S0016-7037(03)00096-6.

Perdew J.P., K. Burke, M. Ernzerhof, Phys. Rev. Lett. 1996, 77, 3865-3868.

Pereira M.F.R., J. J. M. Órfão, J. L. Figueiredo, Appl. Catal. A 1999, 184, 153-160.

(Continued)

*Primary Examiner* — Patricia L. Hailey
(74) *Attorney, Agent, or Firm* — Quarles & Brady LLP

(57) ABSTRACT

Improved catalytic materials for and methods of oxidative dehydrogenation (ODH) of short chain alkanes or ethylbenzene to the corresponding olefins are disclosed. The disclosed methods use catalysts made by impregnating boron onto the surface of oxidized amorphous carbon, and result in higher selectivity and a lower induction period than methods using conventional ODH catalysts.

19 Claims, 27 Drawing Sheets
(10 of 27 Drawing Sheet(s) Filed in Color)

(56) References Cited

OTHER PUBLICATIONS

Pereira M.F.R., J. J. M. Órfão, J. L. Figueiredo, Appl. Catal. A 2001, 218, 307-318.
Pickard C.J., F. Mauri, Phys. Rev. B. 2001, 63, 2451011-2451013.
Qi W., D. Su, ACS Catal. 2014, 4, 3212-3218.
Romanos, J.; Beckner, M.; Stalla, D.; Tekeei, A; Suppes, G.; Jalisatgi, S.; Lee, M.; Hawthorne, F.; Robertson, J. D.; Firlej, L.; et al. Infrared Study of Boron-Carbon Chemical Bonds in Boron-Doped Activated Carbon. Carbon N Y 2013, 54, 208-214. https://doi.org/10.1016/j .carbon.2012.11.031.
Saleh, T. A The Influence of Treatment Temperature on the Acidity ofMWCNT Oxidized by HNO3 or a Mixture of HNO3 /H2SO4. Appl. Surf Sci. 2011, 257 (17), 7746-7751. https://doi.org/10.1016/j .apsusc.2011.04.020.
Sattler et al., Chem. Rev., 2014, 114 (20), 10613-10653.
Wu et al., "Carbon nanotubes oxidized by a green method as efficient metal-free catalysts for nitroarene reductiont", Phys. Chem. Chem. Phys. 2015, 17, 1567-1571.
Schwartz V., W. Fu, Y. T. Tsai, H. M. Meyer, A. J. Rondinone, J. Chen, Z. Wu, S. H. Overbury, C. Liang, ChemSusChem 2013, 6, 840-846.
Sekiya, T.; Machida, N.; Ohtsuka, A; Soejima, A Raman Spectra ofBO3 2TeO2 Glasses. J Non. Cryst. Solids 1992, 151 (3), 222-228. https://doi.org/10.1016/0022-3093(92)90033-G.
Shi L. B. Yan, D. Shao, F. Jiang, D. Wang, A. H. Lu, Chin. J. Catal. 2017, 38, 389-395.
Shi L., Y. Wang, B. Yan, W. Song, D. Shao, A.-H. H. Lu, Chem. Commun. 2018, 54, 10936-10946.
Shi, L.; Wang, D.; Song, W.; Shao, D.; Zhang, W.-P.; Lu, A.-H. Edge-Hydroxylated Boron Nitride for Oxidative Dehydrogenation of Propane to Propylene. ChemCatChem 2017,9, 1788-1793.
Shim, J. W.; Park, S. J.; Ryu, S. K. Effect of Modification with HNO3 and NaOH on Metal Adsorption by Pitch-Based Activated Carbon Fibers. Carbon N Y 2001, 39 (11), 1635-1642. https://doi.org/10.1 0I 6/S0008-6223(00)00290-6.
Takaoka, M.; Yokokawa, H.; Takeda, N. The Effect of Treatment of Activated Carbon by H2O2 or HNO3 on the Decomposition of Pentachlorobenzene. Appl. Cata!. B Environ. 2007, 74 (3-4), 179-186. https://doi.org/10.1016/j.apcatb.2007.02.009.
Tamayo, A et al., "Synthesis and characterization of boron silicon oxycarbide glass fibers", Journal of Non-Crystalline Solids, vol. 358, 2012, doi:10.1016/j.noncrysol.2011.09.002, pp. 155-162.
Thomas A., A. Fischer, F. Goettmann, M. Antonietti, J. O. Müller, R. Schlogl, J. M. Carlsson, J. Mater. Chem. 2008, 18, 4893-4908.
Tkatchenko A., M. Scheffler, Phys. Rev. Lett. 2009, 102, 073005.
Trebosc J., B. Hu, J. P. Amoureux, Z. Gan, J. Magn. Reson. 2007, 186, 220-227.
Ud, I.; Shaharun, M. S.; Subbarao, D.; Naeem, A Surface Modi Fi Cation of Carbon Nano Fi Bers by HNO 3 Treatment. 2016, 42, 966-970.
Van Meerten S.G.J., W. M. J. Franssen, A. P. M. Kentgens, J. Magn. Reson. 2019, 301, 56-66.
Venegas J.M., Z. Zhang, T. O. Agbi, W. P. McDermott, A. Alexandrova, I. Hermans, Angew. Chem., Int. Ed. 2020, ,59, 16527-16535.
Venkatesh A., M. P. Hanrahan, A. J. Rossini, Solid State Nucl. Magn. Reson. 2017, 84, 171-181.
Wang Q., B. Hu, O. Lafon, J. Trebosc, F. Deng, J. P. Amoureux, J. Magn. Reson. 2009, 200, 251-260.
Wong Y.T.A., D. L. Bryce, Annu. Rep. NMR Spectrosc. 2018, 93, 213-279.
Yates J.R., C. J. Pickard, F. Mauri, Phys. Rev. B. 2007, 76, 024401-1-11.
Yu Y., B. Stevensson, M. Eden, J. Phys. Chem. Lett. 2018, 9, 6372-6376.
Zawadzki, J. IR Spectroscopic Investigations of the Mechanism of Oxidation of Carbonaceous Films with HNO3 Solution. Carbon N Y 1980, 18 (4), 281-285. https://doi.org/10.1 0I 6/0008-6223(80)90052-4.
Zhang J., D. Su, A. Zhang, D. Wang, R. Schlogl, C. Hebert, Angew. Chem. Int. Ed. 2007, 46, 7319-7323.
Zhang J., J. O. Müller, W. Zheng, D. Wang, D. Su, R. Schlogl, Nano Lett. 2008, 8, 2738-2743.
Zhang, G.; Sun, S.; Yang, D.; Dodelet, J. P.; Sacher, E. The Surface Analytical Characterization of Carbon Fibers Functionalized by H2SO4/HNO3 Treatment. Carbon N Y 2008, 46 (2), 196-205. https://doi.org/10.1016/j .carbon.2007.11.002.
Zhao T.J., W. Z. Sun, X. Y. Gu, M. Rønning, D. Chen, Y. C. Dai, W. K. Yuan, A. Holmen, Appl. Catal. A 2007, 323, 135-146.
Zhou Y., J. Lin, L. Li, X. Pan, X. Sun, X. Wang, J. Catal. 2018, 365, 14-23.
Zhou, L.; Lin, H.; Chen, W.; Luo, L. IR and Raman Investigation on the Structure of (100-x) B2O3-x[0.5 BaO-0.5 ZnO] Glasses. J Phys. Chem. Solids 2008, 69 (10), 2499-2502. https://doi.org/10.1016/j .jpcs.2008.05.013.
Aldrich S., "IR Spectrum Table & Chart," 2019.
Altvater N., R. Dorn, M. Cendejas, W. McDermott, B. Thomas, A. Rossini, I. Hermans, "B-MWW Zeolite: The Case Against Single-Site Catalysis", Angew. Chem. Int. Ed. 2020, 59, 6546-6550.
Andrews, , L.; Burkholder, T. R. Infrared Spectra of Molecular B(OH)3 and HOBO in Solid Argon. J Chem. Phys. 1992, 97 (10), 7203-7210. https://doi.org/10.1063/1.463545.
Ariggo R., M. E. Schuster, Z. Xie, Y. Yi, G. Wowsnick, L. L. Sun, K. E. Hermann, M. Friedrich, P. Kast, M. Havecker, et al., ACS Catal. 2015, 5, 2740-2753.
Ariharan, A; Viswanathan, B.; Nandhakumar, V. Hydrogen Storage on Boron Substituted Carbon Materials. Int. J Hydrogen Energy 2016, 41 (5), 3527-3536. https://doi.org/10.1016/j .ijhydene.2015.12.169.
Baidoc, S. C.; Ardelean, I. FT-IR and Ramn Spectropic Studies of Ag2O • (100-x) [B2O3•As2O3] Glass System. Mod Phys. Lett. B 2010, 24 (1), 51-58. https://doi.org/10. I 142/S0217984910022172.
Brinkman A., A. P. M. Kentgens, J. Am. Chem. Soc. 2006, 128, 14758-14759.
Brown S.P., S. Wimperis, J. Magn. Reson. 1997, 124, 279-285.
Chaturbedy P., M. Ahamed, M. Eswaramoorthy, "Oxidative Dehydrogenation of Propane over a High Surface Area Boron Nitride Catalyst: Exceptional Selectivity for Olefins at High Conversion", ACS Omega 2018, 3, 369-374.
Chizari K., I. Janowska, M. Houllé, I. Florea, O. Ersen, T. Romero, P. Bernhardt, M. J. Ledoux, C. Pham-Huu, Appl. Catal., A 2010, 380, 72-80.
Clark S.J., M. D. Segall, C. J. Pickard, P. J. Hasnip, M. I. J. Probert, K. Refson, M. C. Payne, Z. Krist. 2005, 220, 567-570.
Collins, J.; Ngo, T.; Qu, D.; Foster, M. Spectroscopic Investigations of Sequential Nitric Acid Treatments on Granulated Activated Carbon: Effects of Surface Oxygen Groups on n Density. Carbon N Y 2013, 57, 174-183. https://doi.org/10.1016/j .carbon.2013.01.061.
Dorn R.W., M. C. Cendejas, K. Chen, I. Hung, N. R. Altvater, W. P. McDermott, Z. Gan, I. Hermans, A. J. Rossini, ACS Catal. 2020, 10, 13852-13866.
Dorn R.W., M. J. Ryan, T.-H. Kim, T. W. Goh, A. Venkatesh, P. M. Heintz, L. Zhou, W. Huang, A. J. Rossini, Chem. Mater. 2020, 32, 3109-3121.
Eden M., D. Zhou, J. Yu, Chem. Phys. Lett. 2006, 431, 397-403.
Esteves L.M., H. A. Oliveira, F. B. Passos, J. Ind. Eng. Chem. 2018, 65, 1-12.
Feng N., Q. Wang, A. Zheng, Z. Zhang, J. Fan, S. Bin Liu, J. P. Amoureux, F. Deng, J. Am. Chem. Soc. 2013, 135, 1607-1616.
Floweri, O.; Jo, H.; Seo, Y.; Lee, N. Improving the Thermal Stability of Carbon Nanotubes and Their Field Emission Characteristics by Adding Boron and Phosphorus Compounds. CarbonN Y 2018, 139, 404-414. https://doi.org/10.1016/j .carbon.2018.06.072.
Frank B., A. Rinaldi, R. Blume, R. Schlögl, D. S. Su, Chem. Mater. 2010, 22, 4462-4470.
Fung B.M., A. K. Khitrin, K. Ermolaev, J. Magn. Reson. 2000, 142, 97-101.
Gilson, T. R. Characterisation of Ortho- and Meta-Boric Acids in the Va Pou r Phase. 1991, 2463-2466.
Gomez-Serrano, V.; Acedo-Ramos, M.; Lopez-Peinado, A.J.; Valenzuela-Calahorrro, C. Mass and Surface Changes of Activated Carbon

(56) References Cited

OTHER PUBLICATIONS

Treated with Nitric Acid. Thermal Behavior of the Samples. Thermochim. Acta 1997, 291 (1-2), 109-115. https://doi.org/10.1016/s0040-6031(96)03098-5.
Grant et al., "Selective Oxidative Dehydrogenation fo Propane to Propene Using Boron Nitride Catalysts", Science (80-), 2016 354 (6319), 1570-1573, https://doi.org/10.1126/science.aaf7885.
Grant J.T., C. A. Carrero, A. M. Love, R. Verel, I. Hermans, ACS Catal. 2015, 5, 5787-5793.
Grant, J. T.; McDermott, W. P.; Venegas, J.M.; Burt, S. P.; Micka, J.; Phivilay, S. P.; Carrero, C. A; Hermans, I. Boron and Boron-Containing Catalysts for the Oxidative Dehydrogenation of Propane. ChemCatChem 2017, 9, 3623-3626. https://doi.org/10.1002/cctc.201701140.
Green T.F.G., J. R. Yates, J. Chem. Phys 2014, 140, 234106.
Harris R.K., E. D. Becker, S. M. Cabral de Menezes, R. Goodfellow, P. Granger, Solid State Nucl. Magn. Reson. 2002, 22, 458-483.
Herold F., S. Prosch, N. Oefner, K. Brunnengraber, O. Leubner, Y. Hermans, K. Hofmann, A. Drochner, J. P. Hofmann, W. Qi, et al., "Nanoscale Hybrid Amorphous/Graphitic Carbon as Key Towards Next-Generation Carbon-Based Oxidative Dehydrogenation Catalysts", Angew. Chem. Int. Ed. 2021,60, 5898-5906.
Hwang S.J., C. Fernandez, J. P. Amoureux, J. Cho, S. W. Martin, M. Pruski, Solid State Nucl. Magn. Reson. 1997, 8, 109-121.
Hwang S.J., C. Y. Chen, S. I. Zones, J. Phys. Chem. B. 2004, 108, 18535-18546.
International Search Report and Written Opinion for corresponding PCT Application No. PCT/US2022/014872, mailed May 4, 2022, 18 pages.
Jaramillo, J.; Alvarez, P. M.; Gomez-Serrano, V. Oxidation of Activated Carbon by Dry and Wet Methods Surface Chemistry and Textural Modifications. Fuel Process. Technol. 2010, 91 (11), 1768-1775. https://doi.org/10.1016/j .fuproc.2010.07.018.
Jawhari T., A. Roid, J. Casado, Carbon 1995, 33, 1561-1565.
Jun, L.; Shuping, X.; Shiyang, G. FT-IR and Raman Spectroscopic Study of Hydrated Borates. Spectrochim. Acta Part A Mal. Spectrosc. 1995, 51 (4), 519-532. https://doi.org/10.1 0I 6/0584-8539(94)00183-C.
Kamitsos, E. I.; Karakassides, M. A; Chryssikos, G. D. Vibrational Spectra of Magnesium-Sodium-Borate Glasses. 2. Raman and Mid-Infrared Investigation of the Network Structure. J Phys. Chem. 1987, 91 (5), 1073-1079. https://doi.org/10.1021/j 100289a014.
Karanjkar, P. U.; Burt, S. P.; Chen, X.; Barnett, K. J.; Ball, M. R.; Kumbhalkar, M. D.; Wang, X.; Miller, J. B.; Hermans, I.; Dumesic, J. A; et al. Effect of Carbon Supports on RhRe Bifunctional Catalysts for Selective Hydrogenolysis of Tetrahydropyran-2-Methanol. Cat. Sci. Technol. 2016, 6, 7841-7851. https://doi.org/10.1039/c6cy01763k.
Keller N., N. I. Maksimova, V. V Roddatis, M. Schur, G. Mestl, Y. V Butenko, V. L. Kuznetsov, R. Schlogl, Angew. Chem. Int. Ed. 2002, 41, 1885-1888.
Kim, U. J.; Furtado, C. A; Liu, X.; Chen, G.; Eklund, P. C. Raman and IR Spectroscopy of Chemically Processed Single-Walled Carbon Nanotubes. J Am. Chem. Soc. 2005, 127 ( 44), 15437-15445. https://doi.org/10.102 l/ja05295 lo.
Konijnendijk, W.L., Stevels, J. M. The Structure of Borate Glasses Studied by Raman Scattering. J Non-Cryst. Solids 1975, 18, 307-331.
Krishnan, K. The Raman Spectrum of Boric Acid. Proc. Ind Acad Sci. 1963, 60 (4), 103-109.
Kroeker S., J. F. Stebbins, Inorg. Chem. 2001, 40, 6239-6246.
Krogh-Moe, J. The Structure of Vitreous and Liquid Boron Oxide. J Non-Cryst. Solids 1969, 1 (4), 269-284.
Lam E., J. H. T. Luong, ACS Catal 2014, 4, 3393-3410.
Love A.M., C. A. Carrero, A. Chieregato, J. T. Grant, S. Conrad, R. Verel, I. Hermans, Chem. Mater. 2016, 28, 5495-5504.
Love, Am.; Cendejas, M. C.; Thomas, B.; McDermott, W. P.; Uchupalanun, P.; Kruszynski, C.; Burt, S. P.; Agbi, T.; Rossini, A J.; Hermans, I. Synthesis and Characterization of Silica-Supported Boron Oxide Catalysts for the Oxidative Dehydrogenation of Propane. J Phys. Chem. C 2019, 123 (44), 27000-27011. https://doi.org/10.102 I/acs.jpcc.9b07429.
Love, AM.; Thomas, B.; Specht, S. E.; Hanrahan, M. P.; Venegas, J.M.; Burt, S. P.; Grant, J. T.; Cendejas, M. C.; McDermott, W. P.; Rossini, A J.; et al. Probing the Transformation of Boron Nitride Catalysts under Oxidative Dehydrogenation Conditions. J Am. Chem. Soc. 2019, 141 (1), 182-190. https://doi.org/10.1021/jacs.8b08165.
Lu W.D., D. Wang, Z. Zhao, W. Song, W. C. Li, A. H. Lu, ACS Catal. 2019, 9, 8263-8270.
Mali G., G. Fink, F. Taulelle, J. Chem. Phys 2004, 120, 2835-2845.
Maniua, D.; Iliescu, T.; Ardelean, I.; Cinta-Pinzaru, S.; Tarcea, N.; Kiefer, W. Raman Study on B2O3—CaO Glasses. J Mal. Struct. 2003, 651-653, 485-488. https://doi.org/10.1016/S0022-2860(03)00129-7.
Marinkas A., F. Arena, J. Mitzel, G. M. Prinz, A. Heinzel, V. Peinecke, H. Natter, Carbon 2013, 58, 139-150.

* cited by examiner

CARBON-SUPPORTED BORON CATALYSTS FOR OXIDATIVE DEHYDROGENATION OF ALKANES

CROSS REFERENCE TO RELATED APPLICATIONS

This application is the U.S. National Stage of PCT/US2022/014872, filed Feb. 2, 2022, and claims benefit of priority to U.S. Provisional application 63/144,561, filed Feb. 2, 2021, the contents of each are incorporated by reference in their entireties.

STATEMENT REGARDING FEDERALLY SPONSORED RESEARCH OR DEVELOPMENT

This invention was made with government support under 1916775 awarded by the National Science Foundation and under DE-SC0017918 awarded by the US Department of Energy. The government has certain rights in the invention.

FIELD OF THE INVENTION

The disclosure relates to catalytic materials containing oxidized amorphous carbon impregnated with boron and methods of producing the same, as well as methods for the oxidative dehydrogenation of alkanes using the catalytic materials.

BACKGROUND OF THE INVENTION $C_3$ and $C_4$ olefins, such as propylene (propene), 1-butene, isobutene and butadiene, are widely used starting materials in the industrial synthesis of a variety of important chemical products. The principal industrial method for producing $C_3$ and $C_4$ olefins is steam cracking, a petrochemical process in which saturated hydrocarbons are broken down into smaller, often unsaturated, hydrocarbons. The products obtained by steam cracking depend on the composition of the feed, the hydrocarbon-to-steam ratio, and on the cracking temperature and furnace residence time. For example, a feed composition that primarily contains ethane (ethane cracking) would result in high ethylene yields, while a feed composition including larger hydrocarbons, such as naptha (naptha cracking), would result in a larger yield of $C_3$ and $C_4$ olefins.

In recent years, the demand for $C_3$ and $C_4$ olefins has outstripped supply from traditional cracker units, and this trend is expected to accelerate. This trend is primarily due to the availability of cheap shale gas, prompting many chemical companies to convert their naphtha crackers into ethane crackers, thus shifting production towards ethylene and away from longer chain $C_3$ and $C_4$ olefins. Accordingly, the demand for $C_3$ and $C_4$ olefins is growing faster than can be supplied by cracking.

Because $C_3$ and $C_4$ olefin production by conventional steam cracking has not kept pace with rising demand, several alternative "on-purpose" olefin production technologies that convert short chain alkanes to the corresponding olefins have been developed. Examples include the catalytic dehydrogenation (DH) of short chain alkanes, such as propane, to the corresponding olefin, such as propene, using a supported $CrO_x/Al_2O_3$ catalyst ("CATOFIN®" (Lummus)), a Pt/Sn alloy supported on $Al_2O_3$ ("OLEFLEX™" (UOP)), or Pt/Sn supported on Zn-aluminate with co-fed steam ("STAR®" (Uhde)) (see Sattler et al., *Chem. Rev.,* 2014, 114 (20), 10613-10653).

These and other currently used on-purpose dehydrogenation technologies are energy intensive, because the dehydrogenation reaction is highly endothermic. Furthermore, because they require high temperature conditions, they result in substantial catalyst deactivation due to the formation of coke. Thus, they require continuous catalyst regeneration. In addition, these processes may require substantially reduced pressure to shift the dehydrogenation equilibrium towards the desired products, further contributing to the high production costs associated with these methods.

Oxidative dehydrogenation (ODH), the catalytic dehydrogenation of feedstock alkanes in the presence of oxygen, is an intriguing alternative to conventional dehydrogenation that addresses each of the disadvantages of current DH technology. When oxygen is co-fed to act as a reactant, the reaction thermodynamics are altered such that the resulting net reaction is exothermic. Accordingly, the reaction can proceed at much lower reaction temperatures, resulting in decreased energy costs and increased catalyst stability. Oxygen in the feed stream also eliminates coke formation on the catalyst surface and thus creates no need for catalyst regeneration.

Despite these purported advantages, industrial-scale ODH processes have not been implemented, due to poor control of unwanted side-reactions (mainly the over-oxidation of olefin to CO and $CO_2$), which results in low olefin selectivity at conversions necessary for industrial implementation. For example, existing catalysts for propane ODH typically provide ~50-60% selectivity to propene at 10% propane conversion, with the byproducts largely made up of CO and $CO_2$. As a result, even after more than 30 years of research into catalysis development for ODH (almost entirely focused on supporting vanadium oxide on amorphous oxide supports (e.g., $SiO_2$, $Al_2O_3$, $TiO_2$, $CeO_2$, $ZrO_2$) and structured oxides (e.g., MCM-41, SBA-15)), ODH has not been successfully used in the industrial-scale production of $C_3$ and $C_4$ olefins.

In recent years, Iye Hermans et al. have disclosed the use of various boron-containing materials as high performing catalysts for the ODH of alkanes (see, e.g., U.S. Pat. Nos. 10,011,540; 10,125,059 and 10,407,364). More specifically, bulk boron materials, such as hexagonal boron nitride (h-BN), exhibit high selectivity towards propylene, and are currently recognized as the benchmark catalyst for the ODH of propane. However, such materials are expensive to synthesize, making them unlikely candidates for large-scale, industrial applications.

Accordingly, there is a need in the art for improved methods and catalysts for the oxidative dehydrogenation of $C_2$-$C_5$ alkanes to the corresponding olefins that exhibit the improved selectivity of bulk boron materials, while potentially being less expensive to implement in large-scale industrial settings.

BRIEF SUMMARY

We disclose herein new and improved catalytic materials and methods for catalyzing the oxidative dehydrogenation of $C_2$-$C_5$ alkanes or $C_2$-$C_5$ alkylbenzene to the corresponding $C_2$-$C_5$ olefins or styrene. The improved methods use catalysts containing an oxidized amorphous carbon support having its surface impregnated with boron. Selectivity for the desired olefin reaction product is comparable to h-BN catalysts, while exhibiting a significantly shorter induction period.

Accordingly, in a first aspect, the disclosure encompasses a catalytic material comprising oxidized amorphous carbon impregnated with boron.

In some embodiments, the catalytic material comprises a plurality of 3-coordinate boron species bound to the oxidized amorphous carbon, wherein the plurality of 3-coordinate boron species comprise $B(OB)(OH)_2$, $B(OB)_2(OH)$, $B(OB)_3$, $B(OB)_2(OC)$, $B(OB)(OC)$, and $B(OC)_3$. In some such embodiments, the majority of 3-coordinate boron species are clustered. In some embodiments, between 60 and 90% of the plurality of 3-coordinate boron species are $B(OB)(OH)_2$, $B(OB)_2(OH)$, and $B(OB)_3$. In some embodiments between 40% and 70% of the plurality of 3-coordinate boron species are $B(OB)(OH)_2$ and $B(OB)_2(OH)$.

In some embodiments, (i) the catalytic material comprises from 25 wt % to 40 wt % boron, based on the total weight of the catalytic material, (ii) the catalytic material comprises a complete layer of boron covering the oxidized amorphous carbon, (iii) the boron is impregnated onto the surface of the oxidized amorphous carbon, (iv) the oxidized amorphous carbon comprises, at its unimpregnated surface, one or more moieties selected from the group consisting of a carboxyl, a phenolic hydroxyl, a carbonyl, an anhydride, and a —C—O, (v) the oxidized amorphous carbon is oxidized activated carbon, (vi) the catalytic material is capable of catalyzing oxidative dehydrogenation (ODH) of an alkane or an alkyl group (e.g. ethane, propane, n-butane, isobutane, or any combination thereof), (vii) wherein the catalytic material has an ODH induction period of less than 12 hours, (viii) the catalytic material is thermally stable (e.g. at a temperature equal to or less than 600° C.), or any combination thereof.

In a second aspect, the disclosure encompasses a method of producing a catalytic material comprising impregnating oxidized amorphous carbon with boron.

In some such embodiments, impregnating the surface of the oxidized amorphous carbon with boron is performed by contacting the oxidized amorphous carbon with excess boric acid solution.

In some embodiments, the method further comprises oxidizing amorphous carbon to produce the oxidized amorphous carbon, calcining the impregnated oxidized amorphous carbon, thermally treating the impregnated oxidized amorphous carbon, or any combination thereof.

In some such embodiments, oxidizing amorphous carbon to produce the oxidized amorphous carbon is completed by contacting amorphous carbon with an oxidizing agent under conditions suitable for producing the oxidized amorphous carbon. In some such embodiments, the oxidizing agent is nitric acid, ozone, or hydrogen peroxide.

In some such embodiments, thermally treating the impregnated oxidized amorphous carbon is completed by heating the impregnated oxidized amorphous carbon under an inert atmosphere.

In some embodiments, the method produces the catalytic material disclosed in the first aspect.

In a third aspect, the disclosure encompasses a method of making one or more desired chemical products. The method includes the step of contacting a heterogeneous catalyst including the catalytic material as described above with oxygen and one or more liquid or gaseous reactants. The heterogeneous catalyst catalyzes the oxidative dehydrogenation of the one or more liquid or gaseous reactants to form the one or more desired chemical products.

In some embodiments, the one or more liquid or gaseous reactants comprise an alkane or a hydrocarbon comprising an alkyl group, and the one or more desired chemical products comprise one or more olefins or one or more hydrocarbons comprising an alkenyl group.

In some embodiments, the one or more liquid or gaseous reactants comprise a $C_2$-$C_5$ alkane or $C_2$-$C_5$ alkylbenzene.

In some embodiments, the one or more liquid or gaseous reactants comprise ethane, propane, n-butane, isobutane, or any combination thereof.

In some embodiments, the one or more desired chemical products comprise ethene, propene, isobutene, 1-butene, 2-butene, butadiene, or any combinations thereof. In some such embodiments, the one or more liquid or gaseous reactants comprise propane and the one or more desired chemical produces comprises propene. In some embodiments, the one or more liquid or gaseous reactants comprise ethylbenzene.

In some embodiments, (i) the contacting step occurs at a temperature of from 400° C. to 800° C., (ii) the oxygen and one or more liquid or gaseous reactants are in a reactant stream that is contacted with the heterogeneous catalyst, (iii) the heterogeneous catalyst has an induction period of less than 12 hours, (iv) the heterogeneous catalyst has a selectivity for the one or more desired chemical products of 70% or greater, or any combination thereof.

In some embodiments, the reactant stream comprises from 0% to 70% nitrogen by volume.

In some embodiments, the heterogeneous catalyst has an induction period of eight hours or less.

In some embodiments, the heterogeneous catalyst has the selectivity for the one or more desired chemical products of 85% or greater.

Further features and advantages of the disclosed methods and catalytic materials will be apparent from the following detailed description when taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood and features, aspects and advantages other than those set forth above will become apparent when consideration is given to the following detailed description thereof. Such detailed description makes reference to the following drawings.

Figure 15:
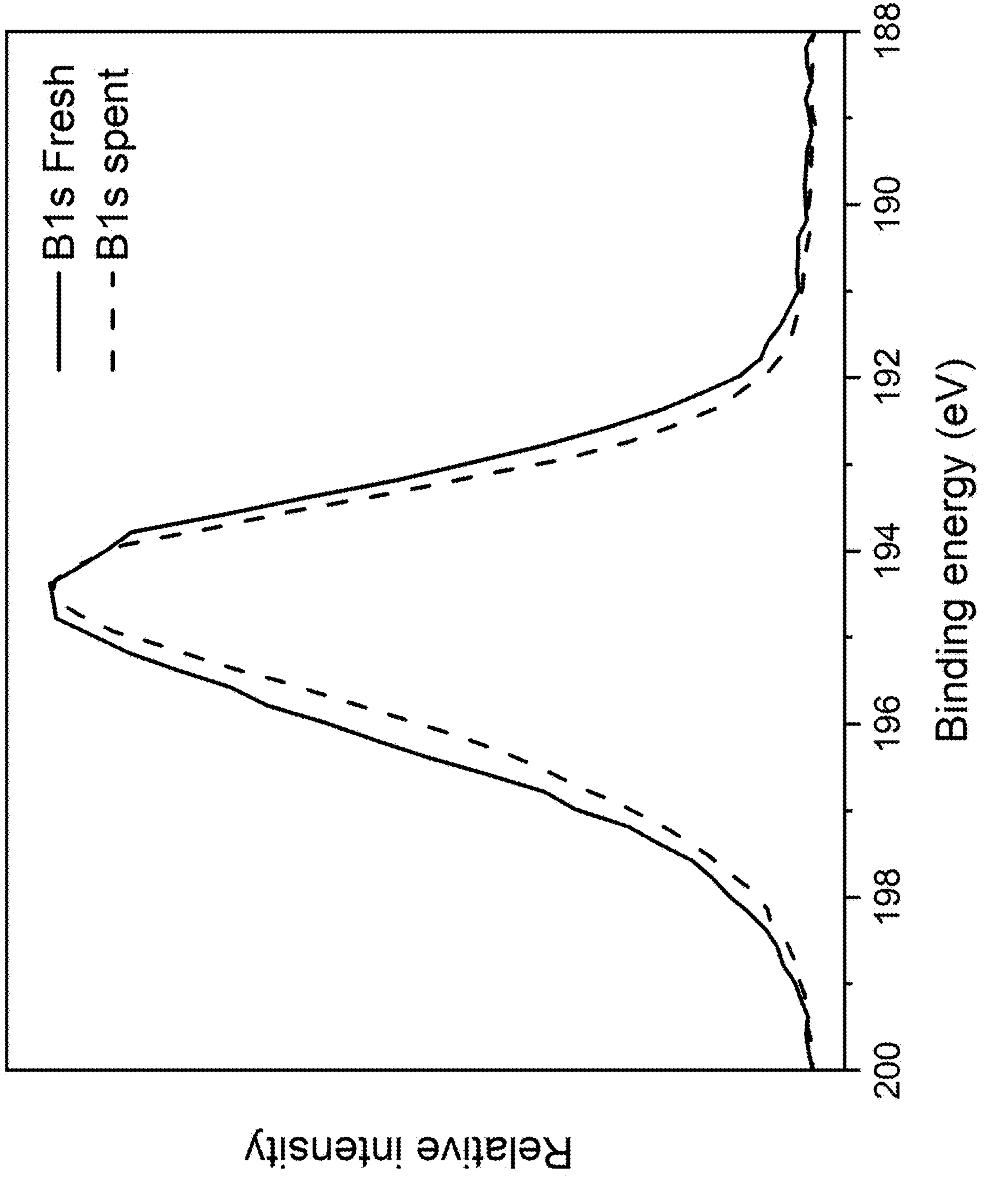

$cm^{-1}$ (full spectrum is given in FIG. 15). Deconvolution of (top right) the 1238 $cm^{-1}$ peak for OAC and (bottom right) the 1436 $cm^{-1}$ peak for fresh B/OAC. Deconvolutions were completed using the fityk software package and the spectra features were assigned based on literature reports.

Figures 4A, 4B:
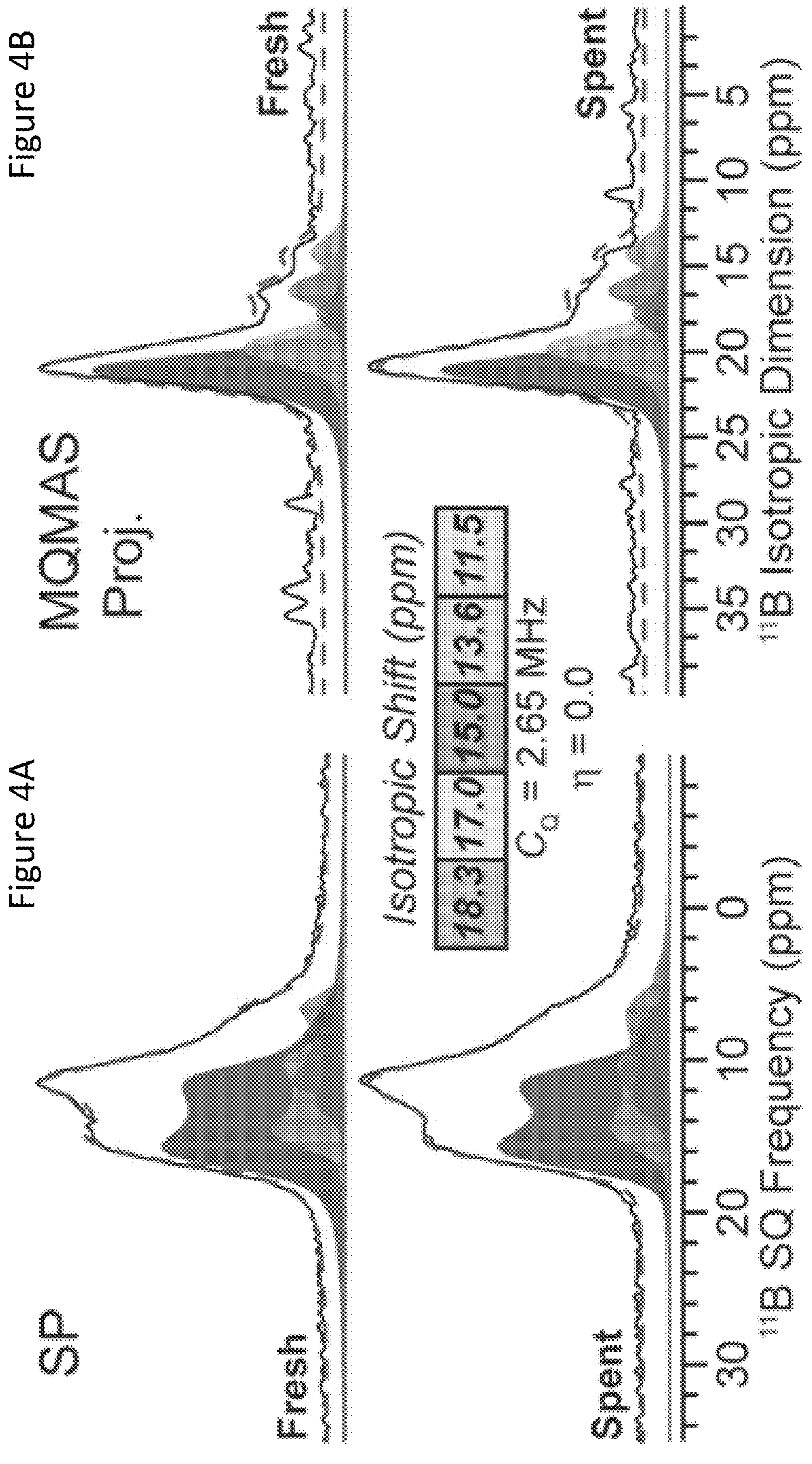

FIG. 4A is a graph illustrating 1D $^{11}B$ 10° tip-angle single-pulse (SP) spectra of (upper) fresh and (lower) spent B/OAC.

FIG. 4B is a graph illustrating $^{11}B$ 3Q-MQMAS isotropic (indirect) dimension projections of (upper) fresh and (lower) spent B/OAC. The black and red spectra correspond to the experimental and analytically simulated spectra, respectively.

Figure 4C:
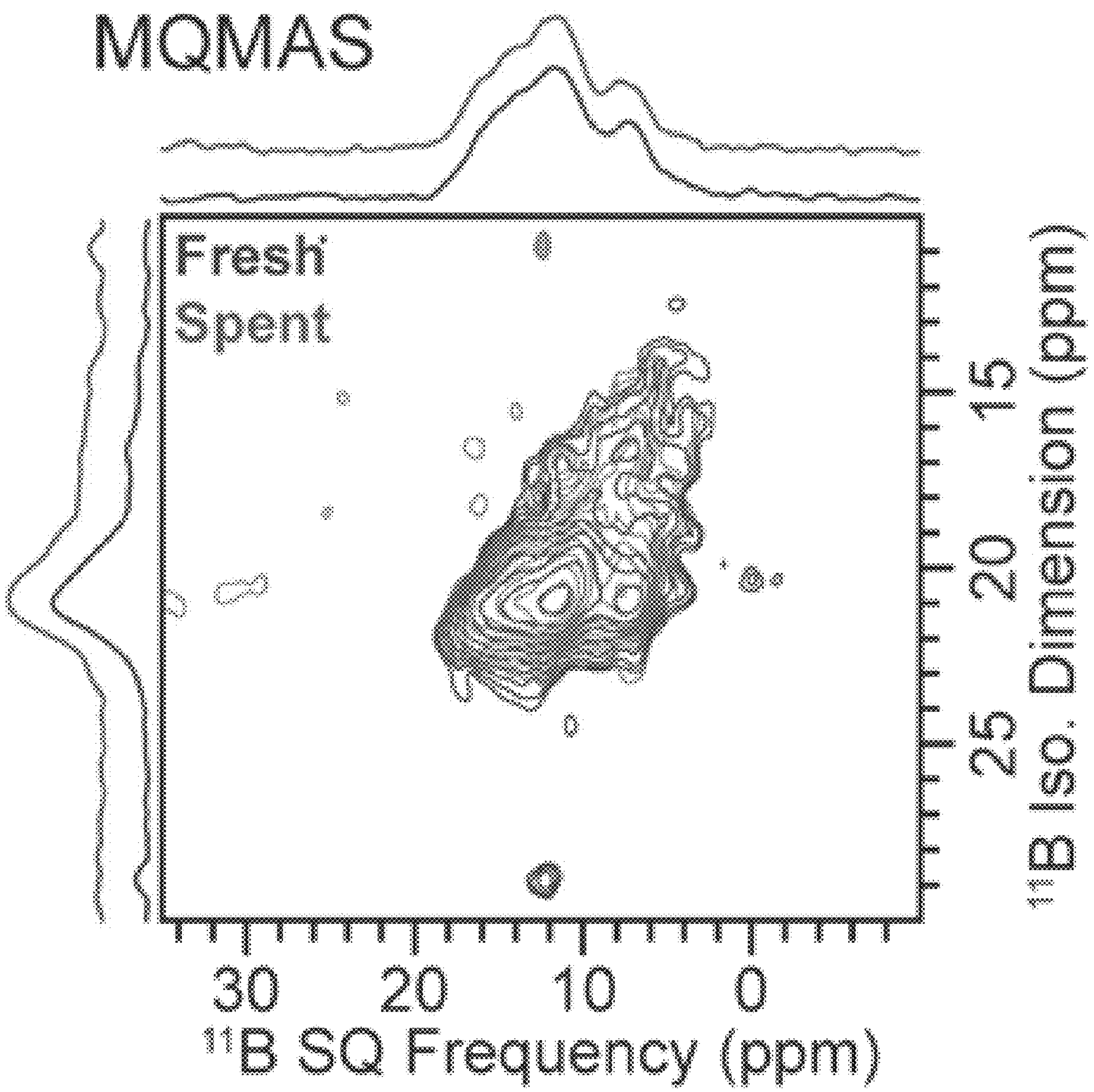

FIG. 4C is a graph illustrating 2D $^{11}B$ 3Q-MQMAS spectra of (blue) fresh and (red) spent B/OAC. All spectra were acquired with 25 kHz MAS and $B_0$=14.1 T.

Figure 5A:
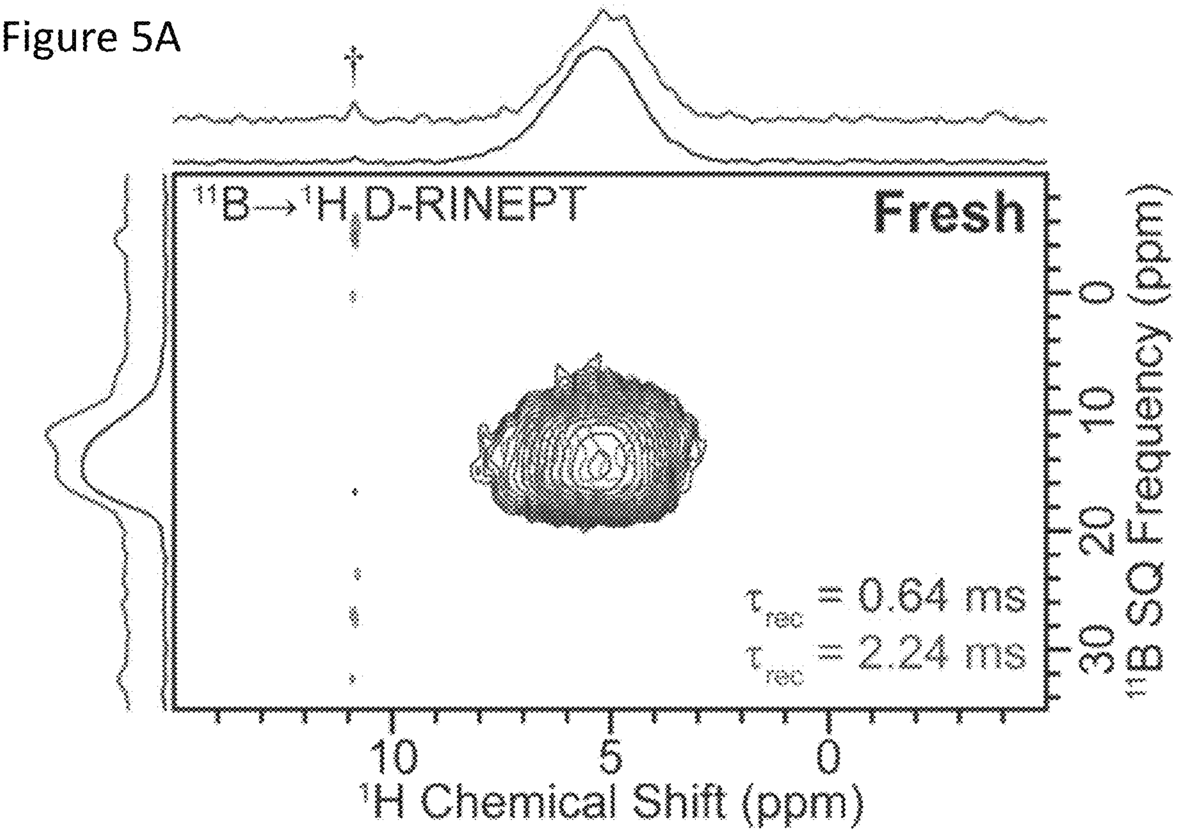

FIG. 5A is a graph showing 2D $^{11}B \rightarrow {}^{1}H$ D-RINEPT spectra of fresh B/OAC recorded with either (blue) 0.64 or (red) 2.24 ms of total $$SR4_1^2$$

heteronuclear dipolar recoupling applied to the $^1H$ spins, 25 kHz MAS and $B_0$=14.1 T. The dagger at ca. 11 ppm indicates an artefact in the 2D NMR spectra.

Figure 5B:
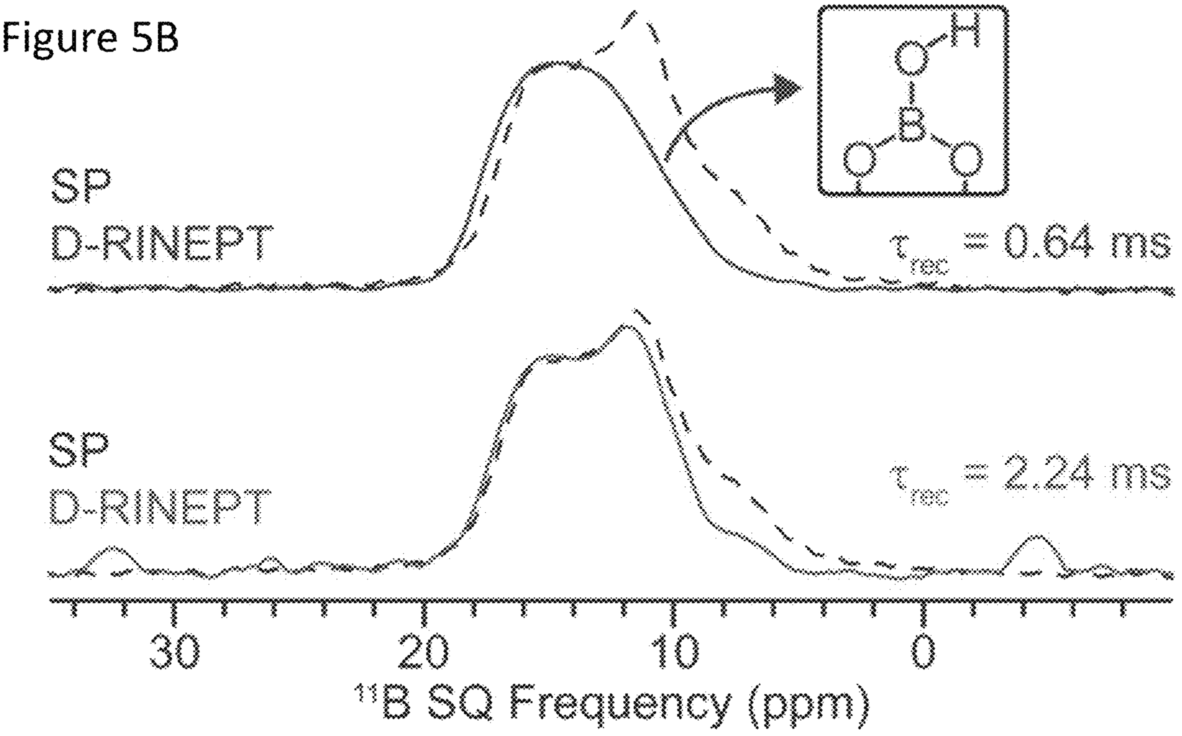

FIG. 5B is a graph illustrating comparison of the (red or blue solid lines of FIG. 5A) D-RINEPT $^{11}B$ projections with the (black dashed lines) 10° tip-angle single pulse (SP) $^{11}B$ NMR spectrum of fresh B/OAC.

Figure 6:
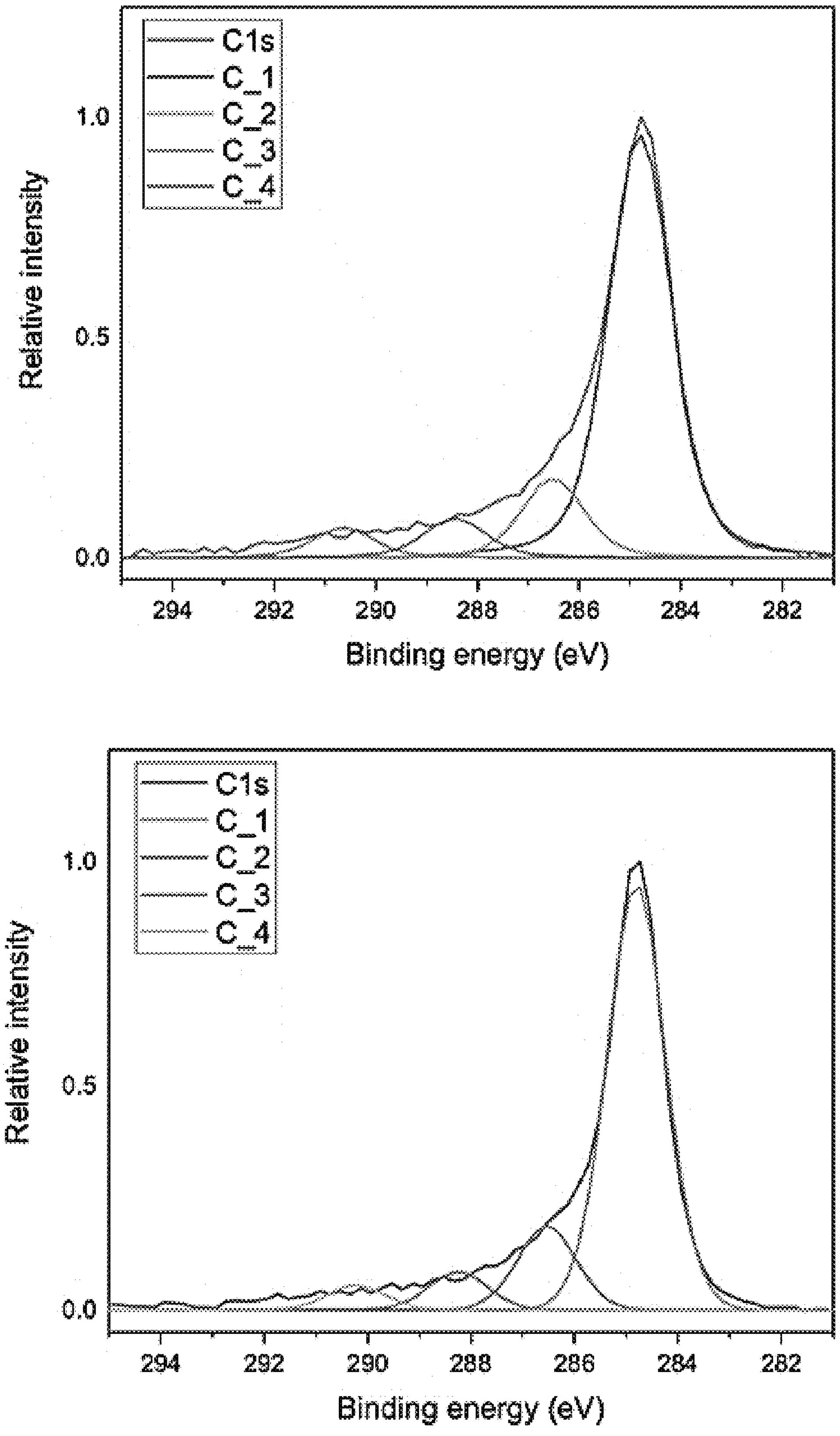

FIG. 6 shows carbon 1s spectra of fresh and spent B/OAC. The dominating peak is $sp^3$ hybridized carbon. Peaks under the C1s envelope from left to right: (upper panel) C_3 (C═C), C_4 (O—C═O), C_2 (C—OC/C—OH), and C_1 (C—C) and (lower panel) C_4 (C═C), C_3 (O—C═O), C_2 (C—OC/C—OH) and C_1 (C—C).

Figure 7:
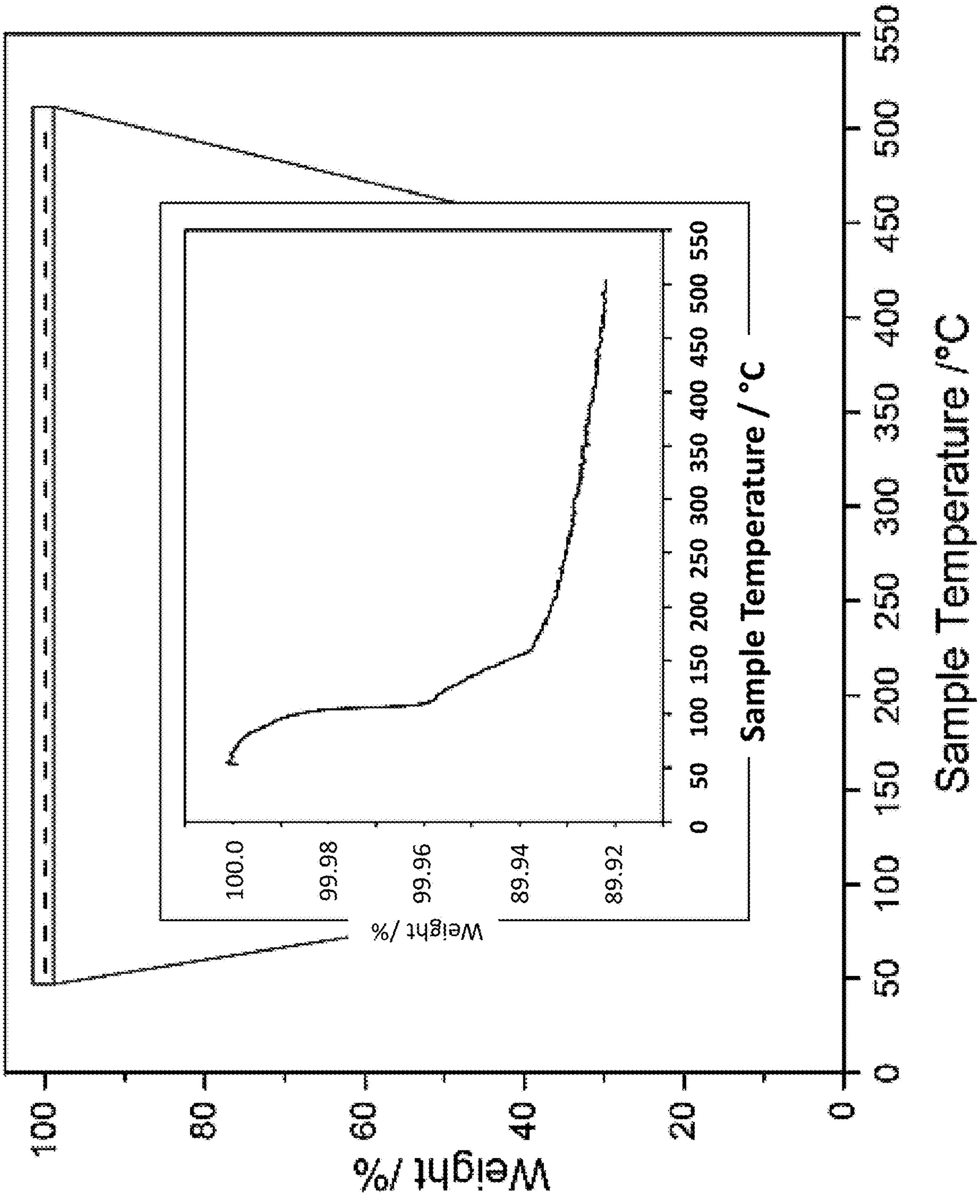

FIG. 7 shows TGA of B/OAC from 50 to 500° C. Inset shows zoomed in weight loss curve.

Figure 8A:
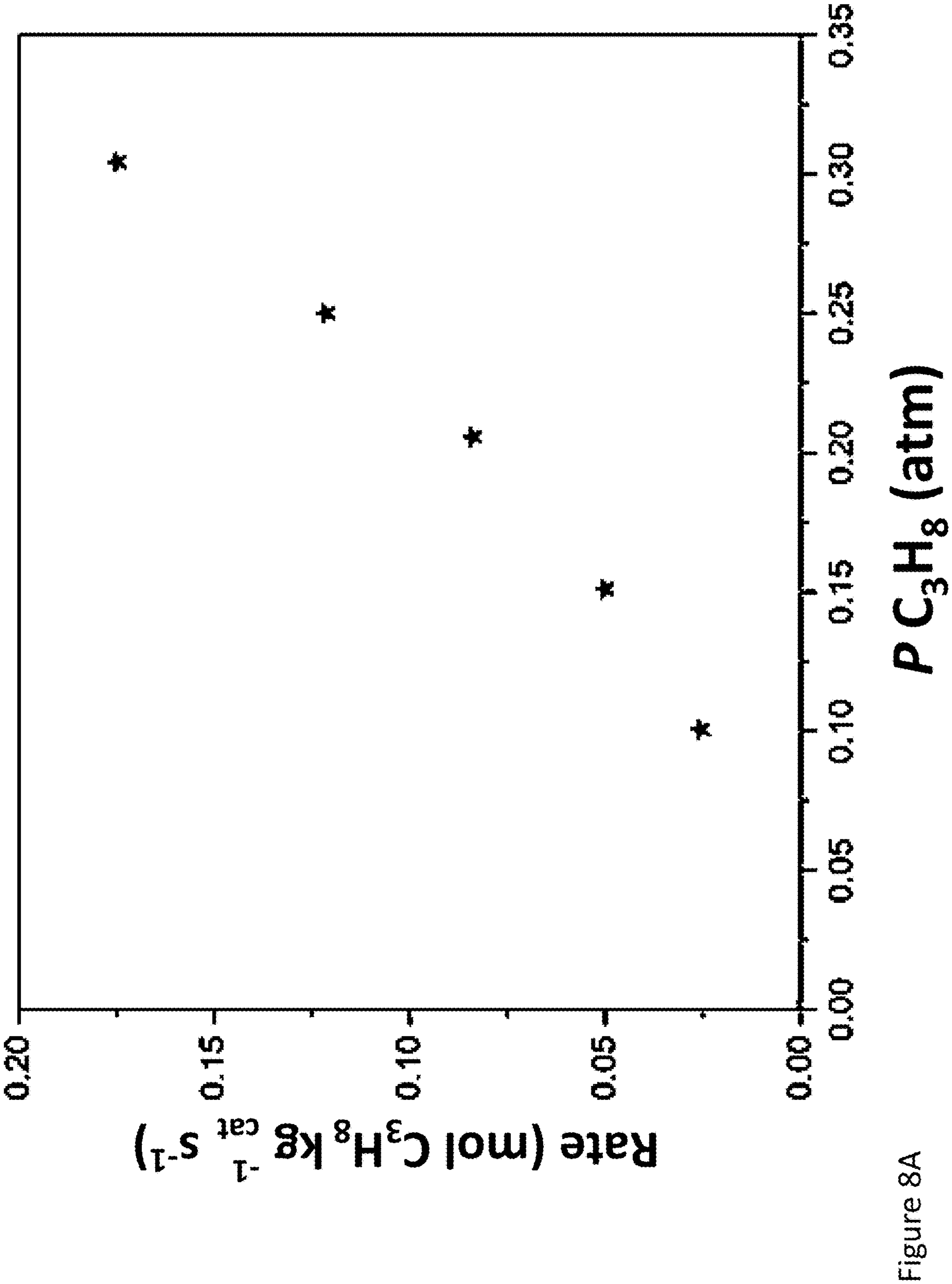
Figure 8B:
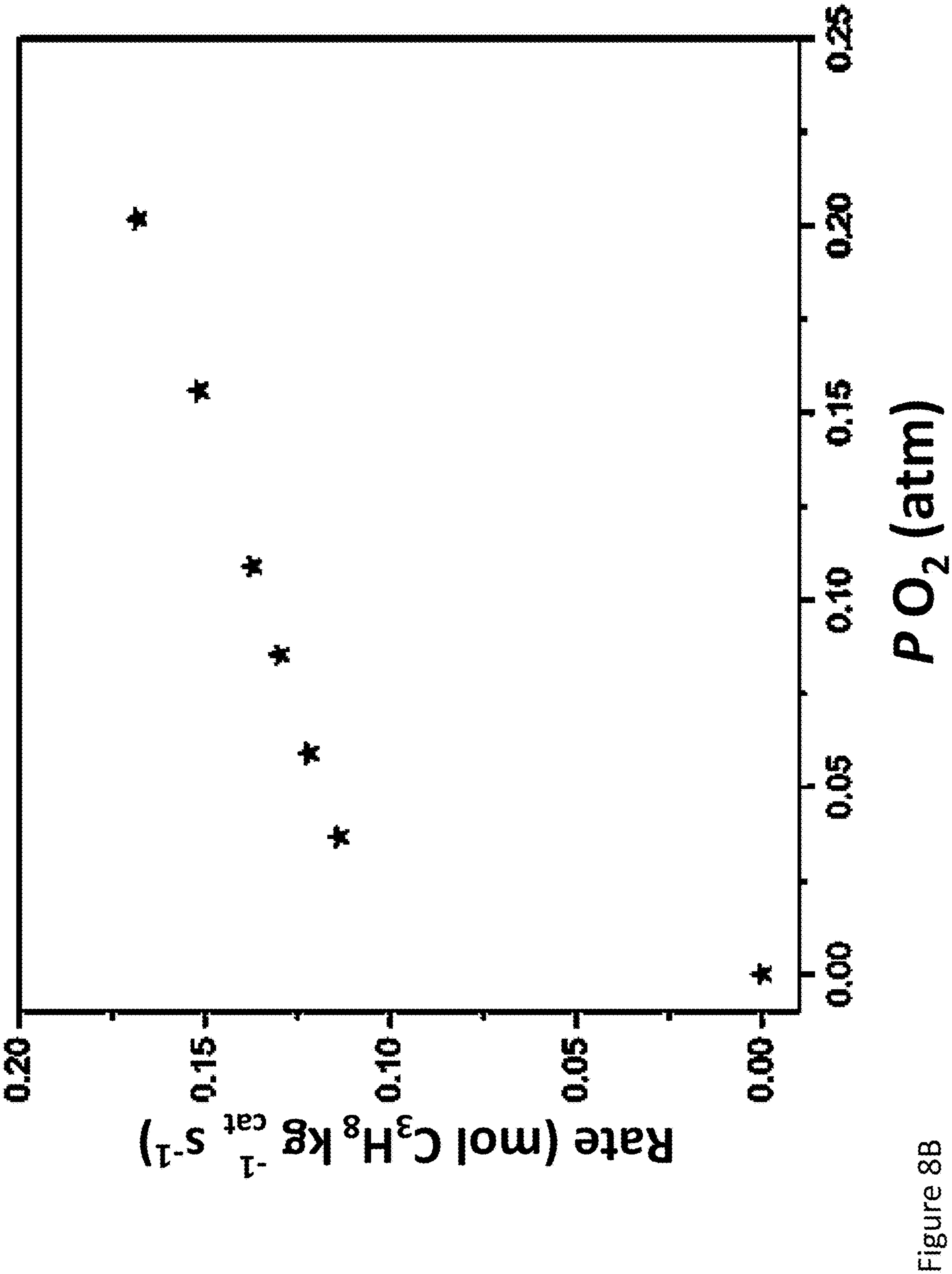

FIGS. 8A-8B shows rate as a function of the partial pressure of (FIG. 8A) propane and (FIG. 8B) oxygen. The strongly asymptotic kinetic behavior typically described with previously investigated systems is less pronounced here, with slight increases in rate still observed at higher Poe which suggest that saturation kinetics may not accurately describe the mechanism of boron-catalyzed ODH, which may be addressed with further kinetic studies.

Figure 9:
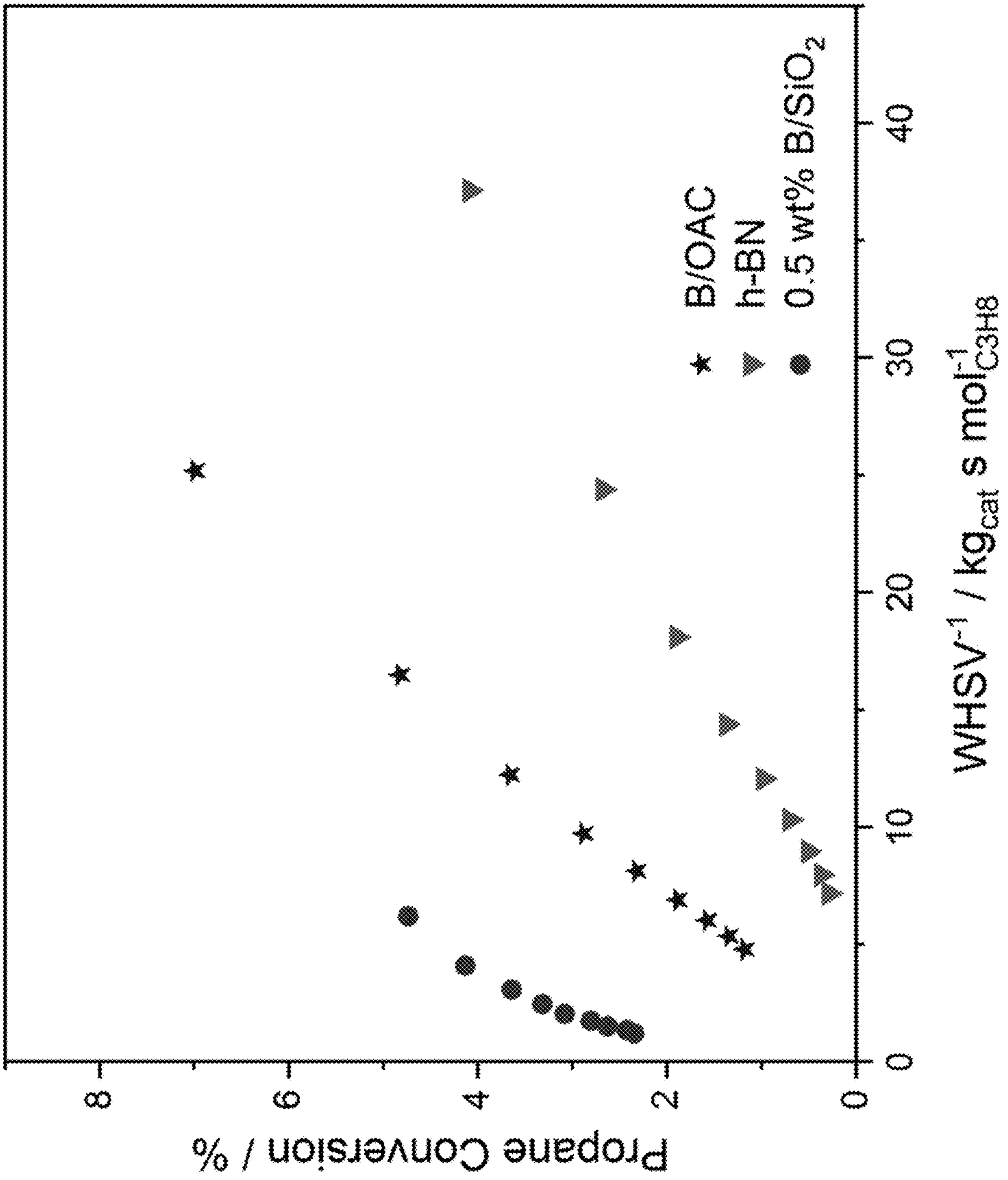

FIG. 9 shows propane conversion as a function of inverse weight-hourly space velocity ($WHSV^{-1}$) at 500° C.

Figure 10:
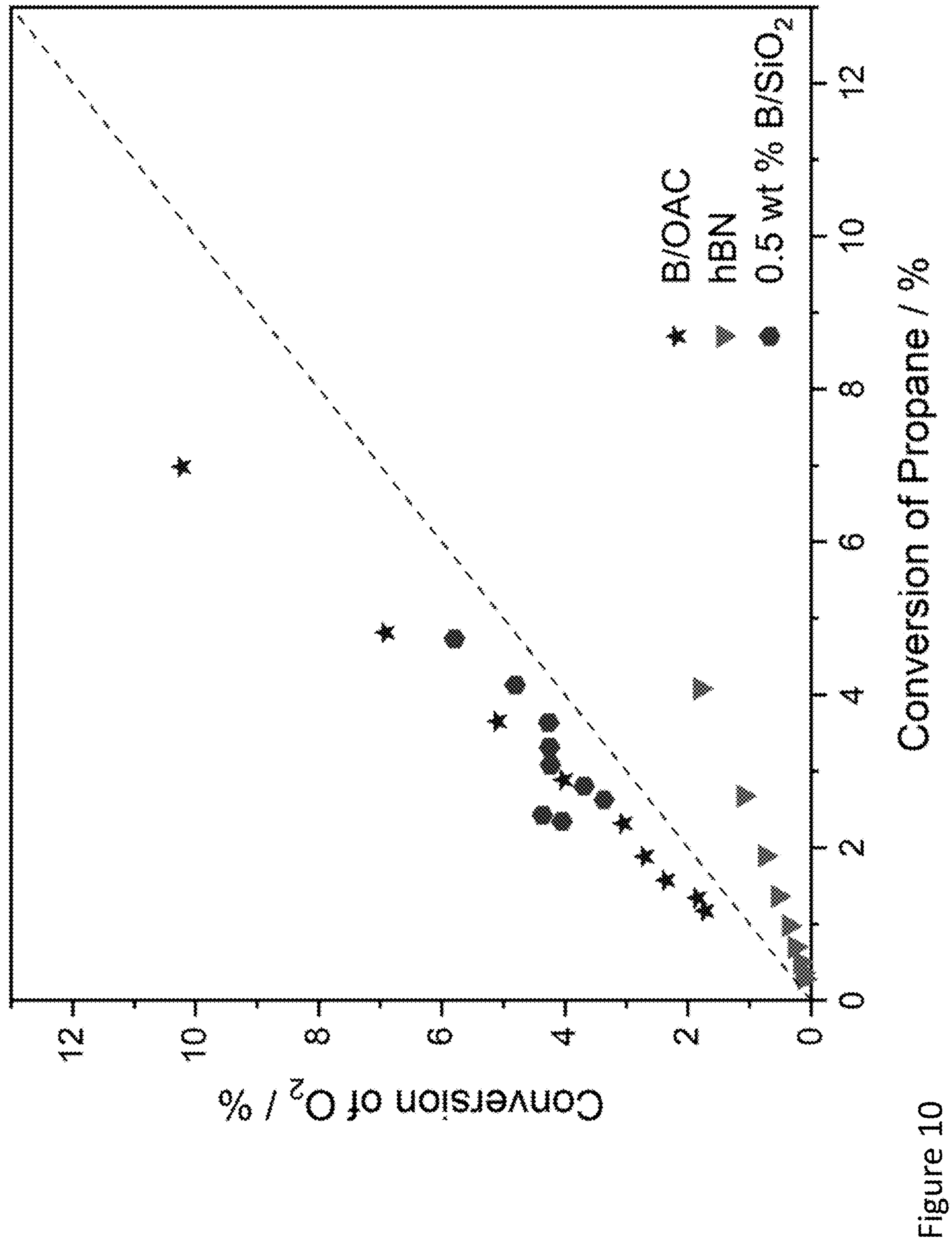

FIG. 10 shows conversion of propane versus conversion of oxygen for B/OAC, h-BN, and 0.5 wt % $B/SiO_2$ at 500° C.

Figure 11:
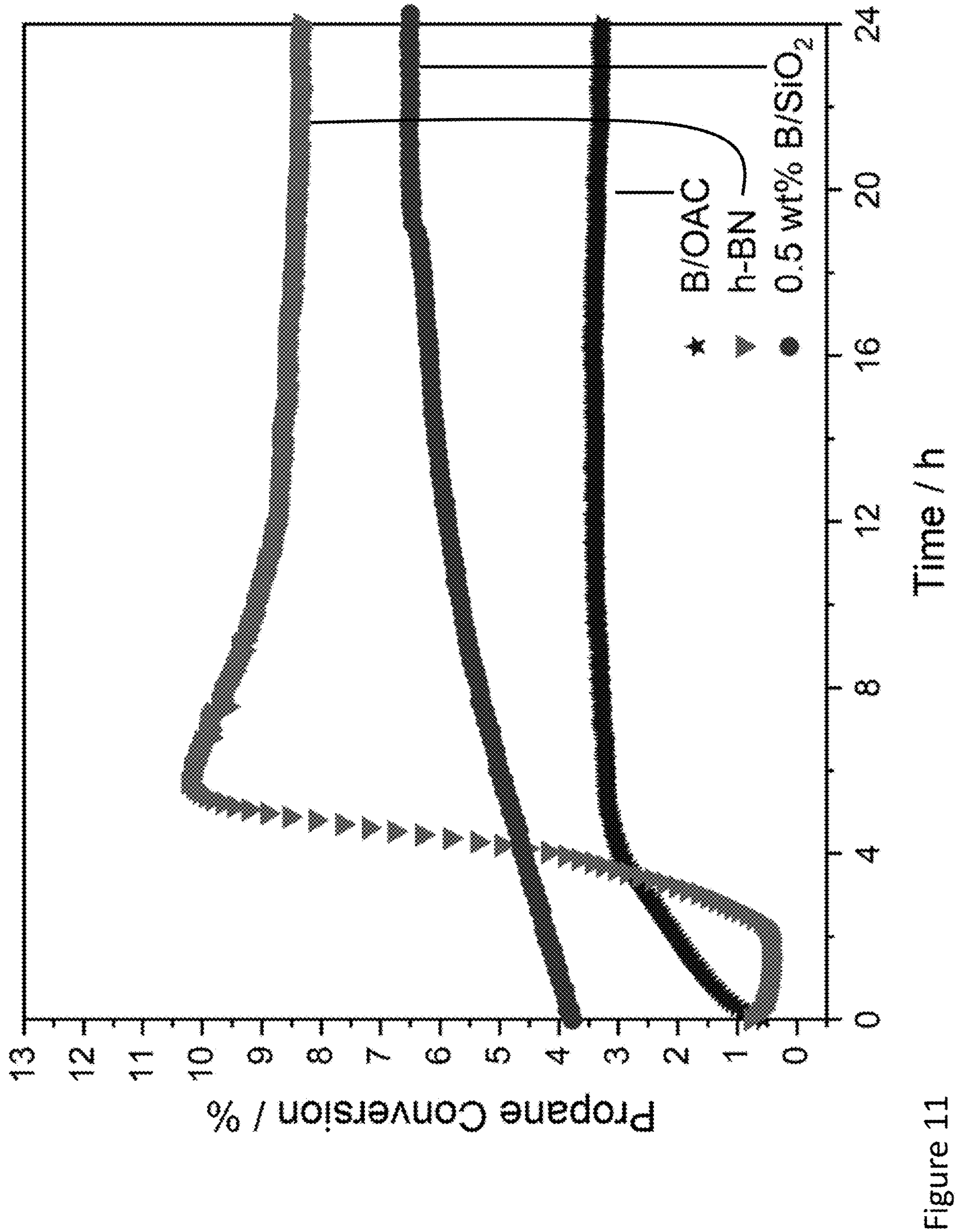

FIG. 11 shows propane conversion as a function of time for B/OAC, h-BN, and 0.5 wt % $B/SiO_2$. B/OAC and $B/SiO_2$ were held at 500° C. and h-BN was held at 550° C. While h-BN required higher temperatures to activate, all other conversion and selectivity data for h-BN was collected at 500° C.

Figure 12:
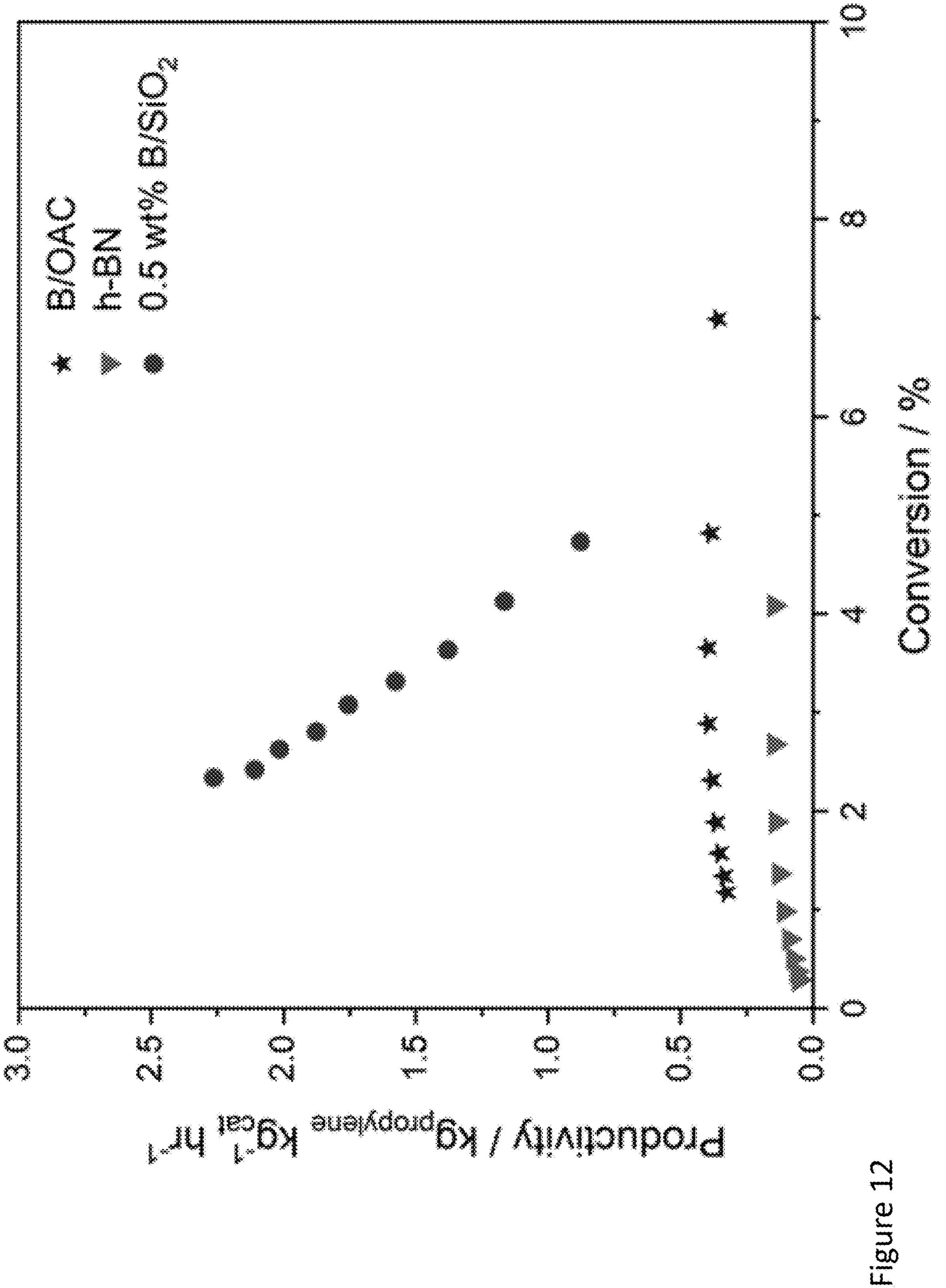

FIG. 12 shows productivity as a function of conversion for B/OAC, h-BN, and 0.5 wt % $B/SiO_2$ at 500° C.

Figure 13:
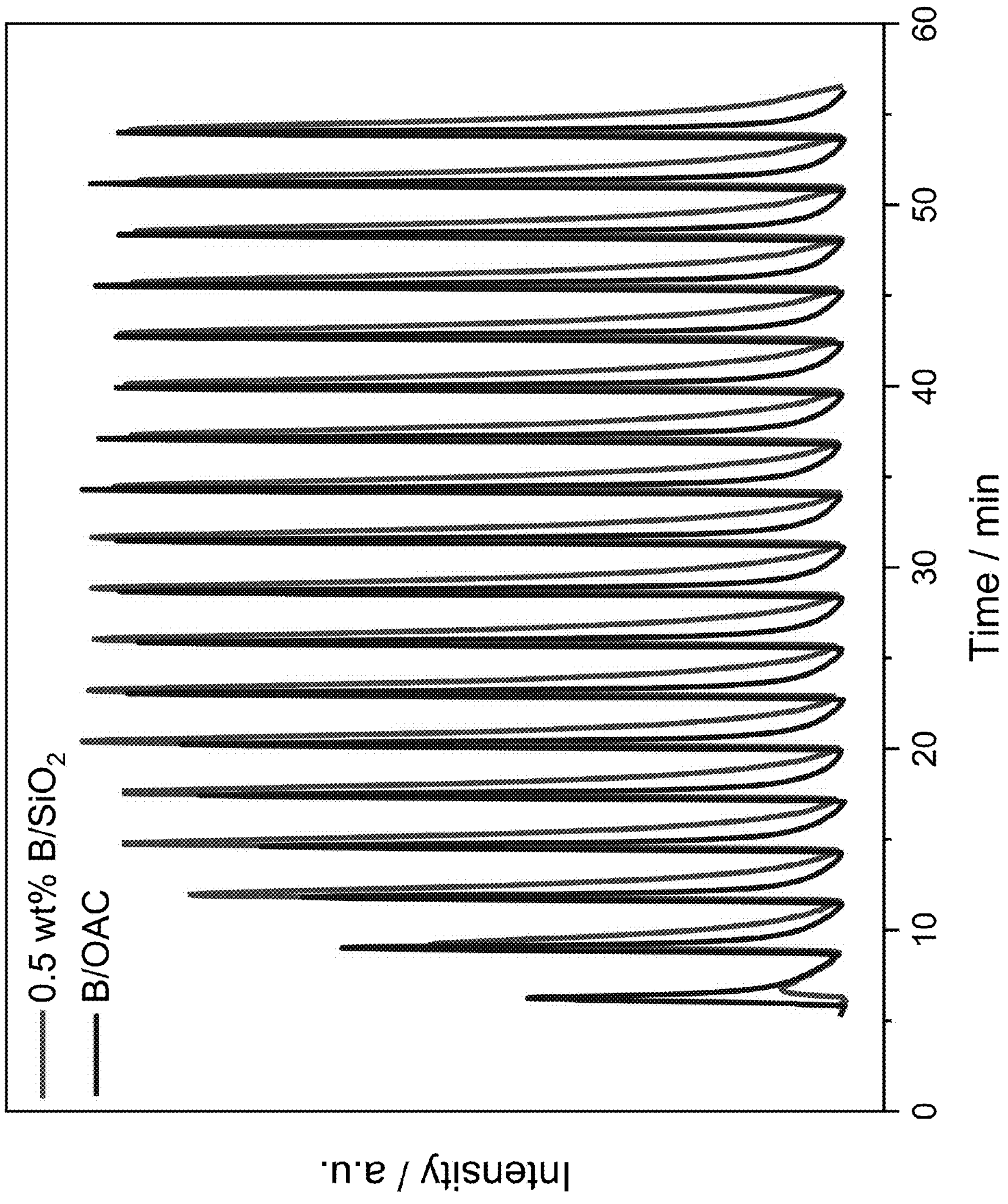

FIG. 13 shows pulse water adsorption for 0.5 wt % $B/SiO_2$ (2.78 $mL_{H2O}\ g_{cat}^{-1}$) and B/OAC (0.58 $mL_{H2O}\ g_{cat}^{-1}$).

Figure 14:
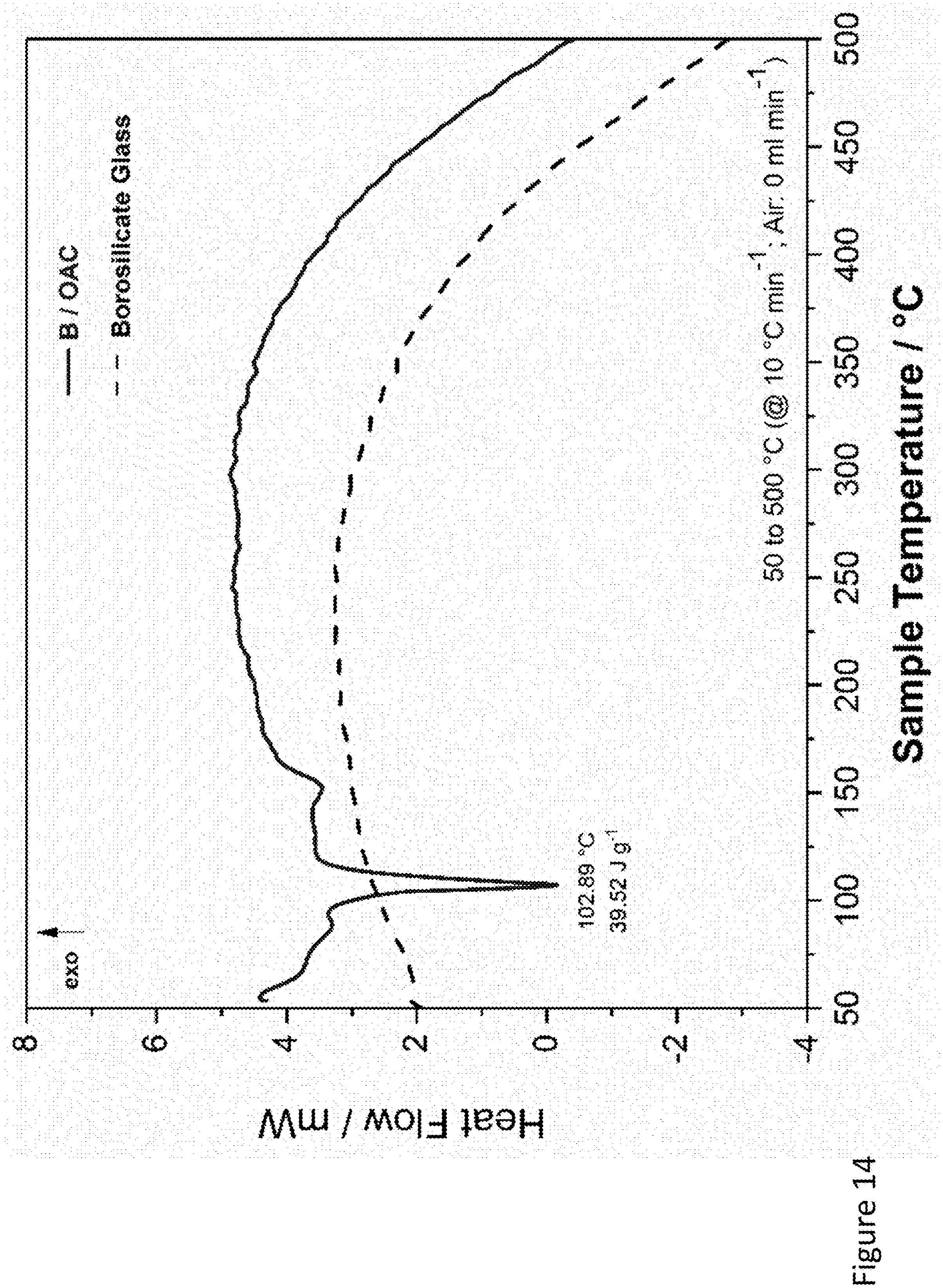

FIG. 14 shows differential Scanning calorimetry (DSC) scans for B/OAC (red straight line) and finely crushed borosilicate glass powder (black dashed line).

FIG. 15 shows the XPS B is region of fresh (solid) and spent (dotted) B/OAC.

Figure 16:
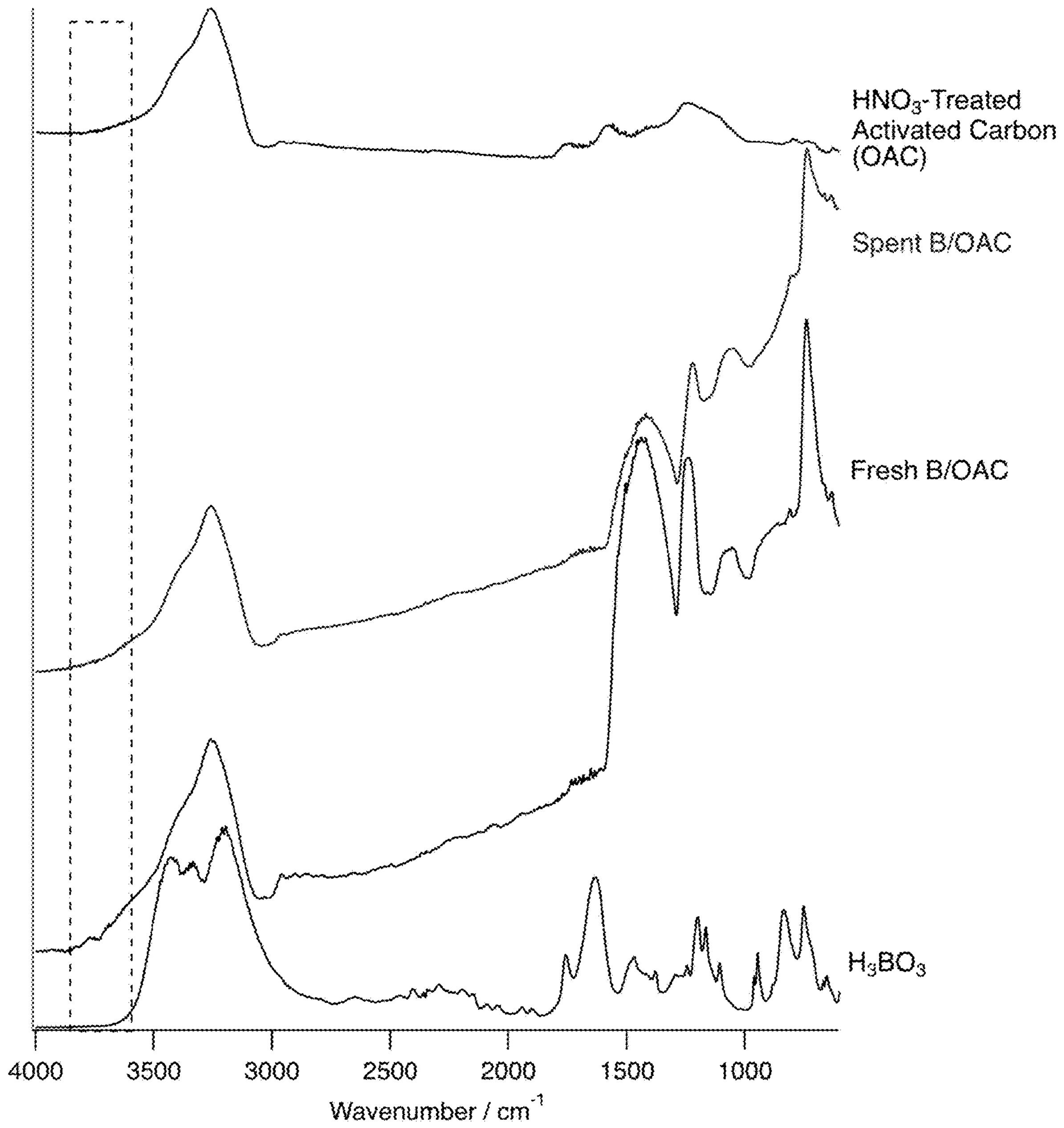

FIG. 16 shows DRIFTS of $H_3BO_3$, fresh and spent B/OAC, and OAC from 600 to 4000 $cm^{-1}$. The dashed box highlights the presence or lack of features around 3750 $cm^{-1}$.

Figure 17:
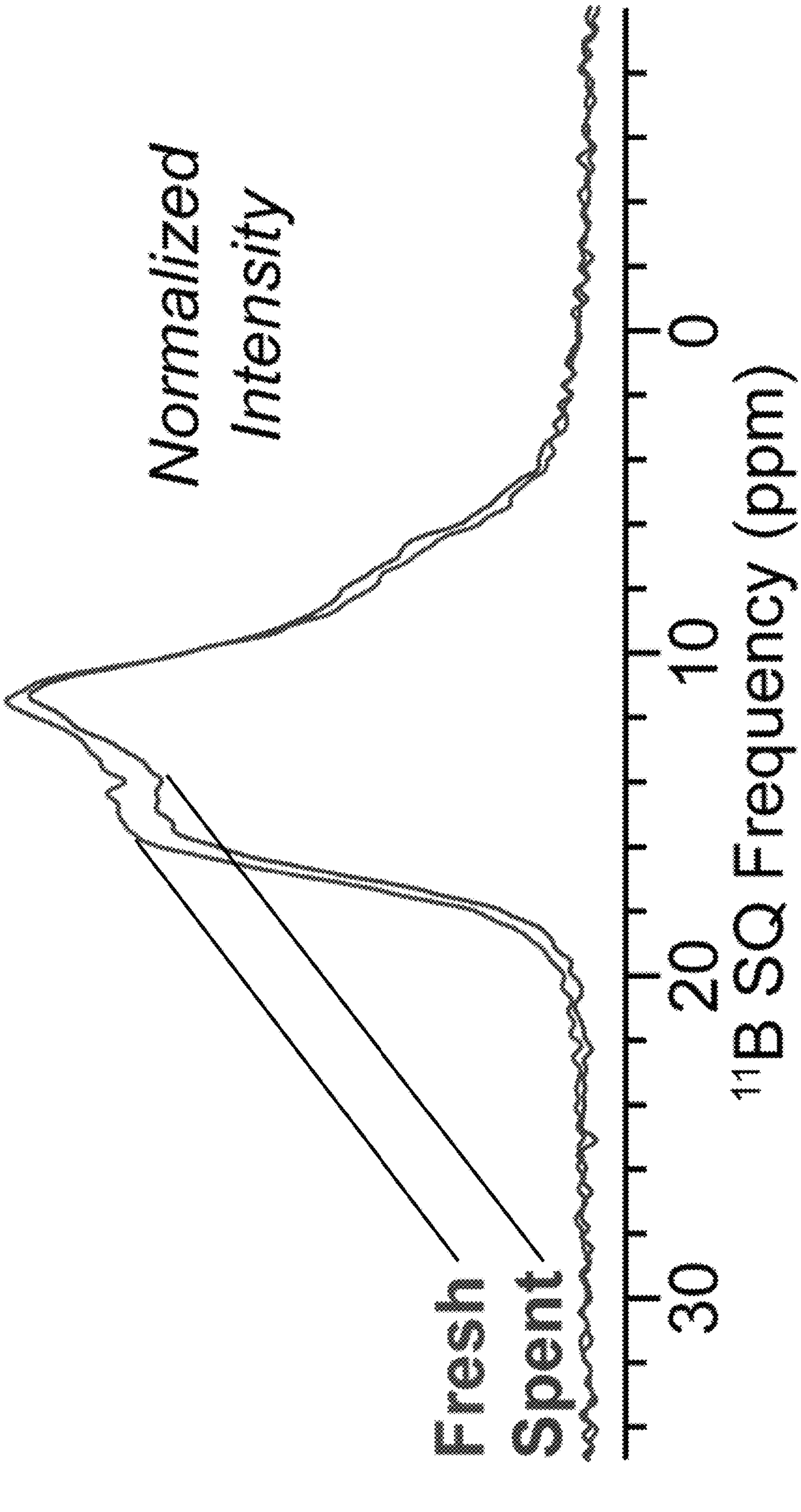

FIG. 17 shows 1D $^{11}B$ 10° tip-angle single-pulse (SP) spectra of fresh and spent B/OAC. Both spectra were acquired with identical experimental parameters, same relatively recycle delay (>5*$T_1$), 25 kHz MAS and $B_0$=14.1 T. The intensities of both spectra are normalized, revealing near identical amount and type of boron species present in the fresh and spent catalysts.

Figure 18A:
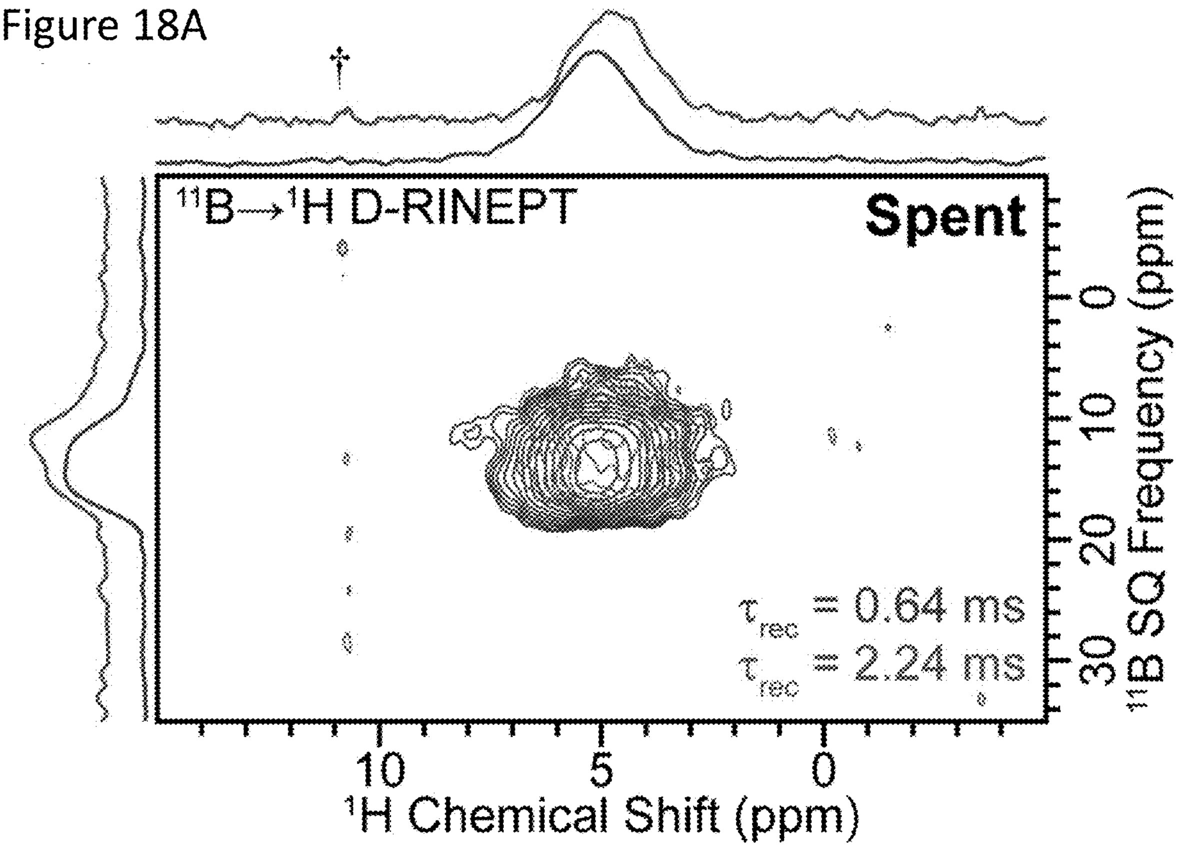

FIG. 18A shows 2D $^{11}B \rightarrow {}^{1}H$ D-RINEPT spectra of spent B/OAC recorded with either 0.64 or 2.24 ms of total $$SR4_1^2$$

heteronuclear dipolar recoupling applied to the $^1H$ spins, 25 kHz MAS and $B_0$=14.1 T. The dagger at ca. 11 ppm indicates an artefact in the 2D spectra.

Figure 18B:
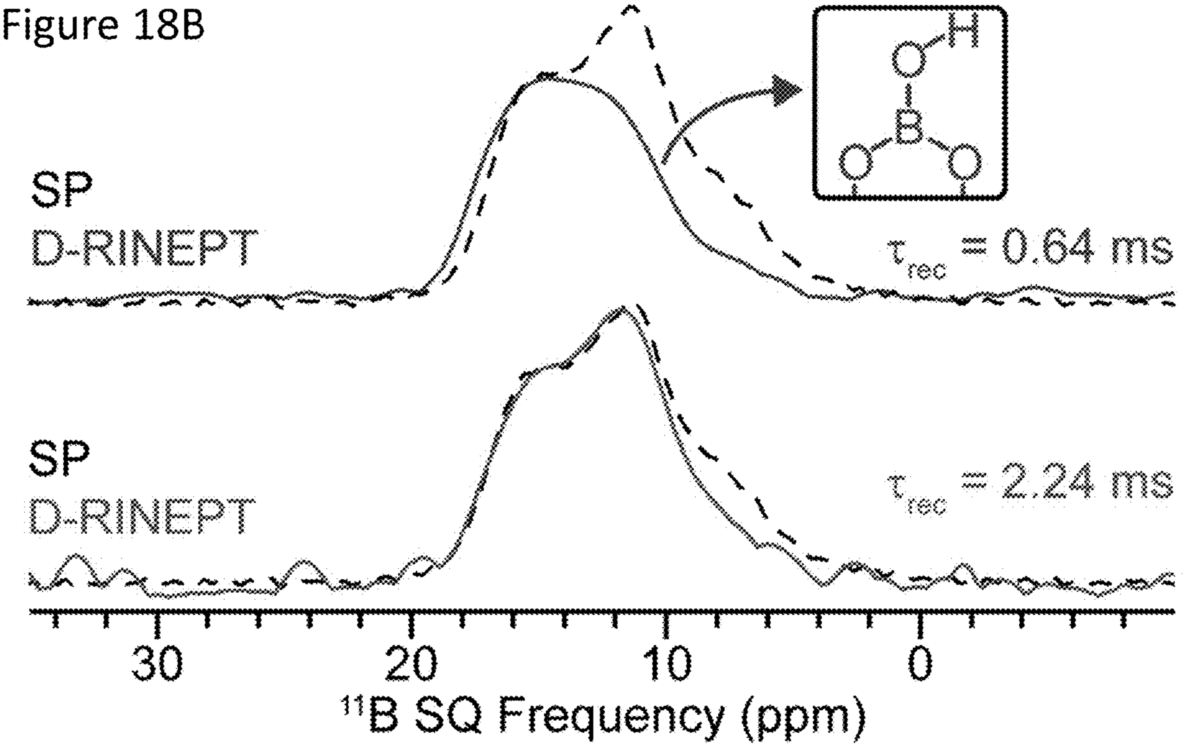

FIG. 18B shows comparison of the (solid lines of FIG. 18A) D-RINEPT $^{11}B$ projections with the (dashed lines) 10° tip-angle single pulse (SP) $^{11}B$ NMR spectrum of spent B/OAC.

Figure 19:
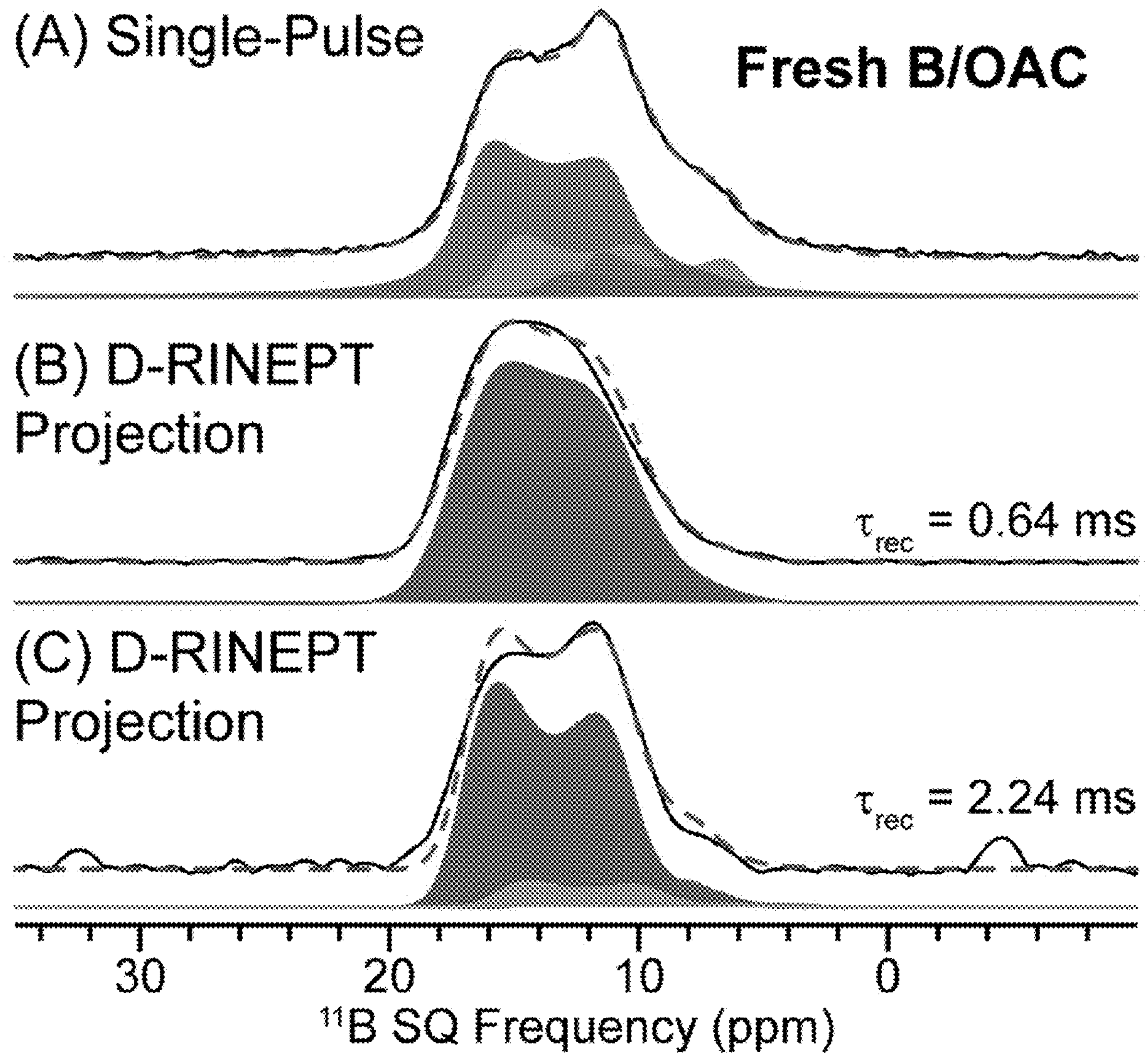

FIG. 19 shows (A) direct exciation single-pulse NMR spectrum of fresh B/OAC and (B, C) $^{11}B$ projections from the 2D $^{11}B \rightarrow {}^{1}H$ D-RINEPT spectra of fresh B/OAC recorded with (B) 0.64 or (C) 2.24 ms of total $$SR4_1^2$$

heteronuclear dipolar recoupling applied to the $^1H$ spins. Dashed lines correspond to experimental and analytically simulated spectra, respectively. The color of the fits correspond to the fits given in FIG. 4 and Table 1.

Figure 20A:
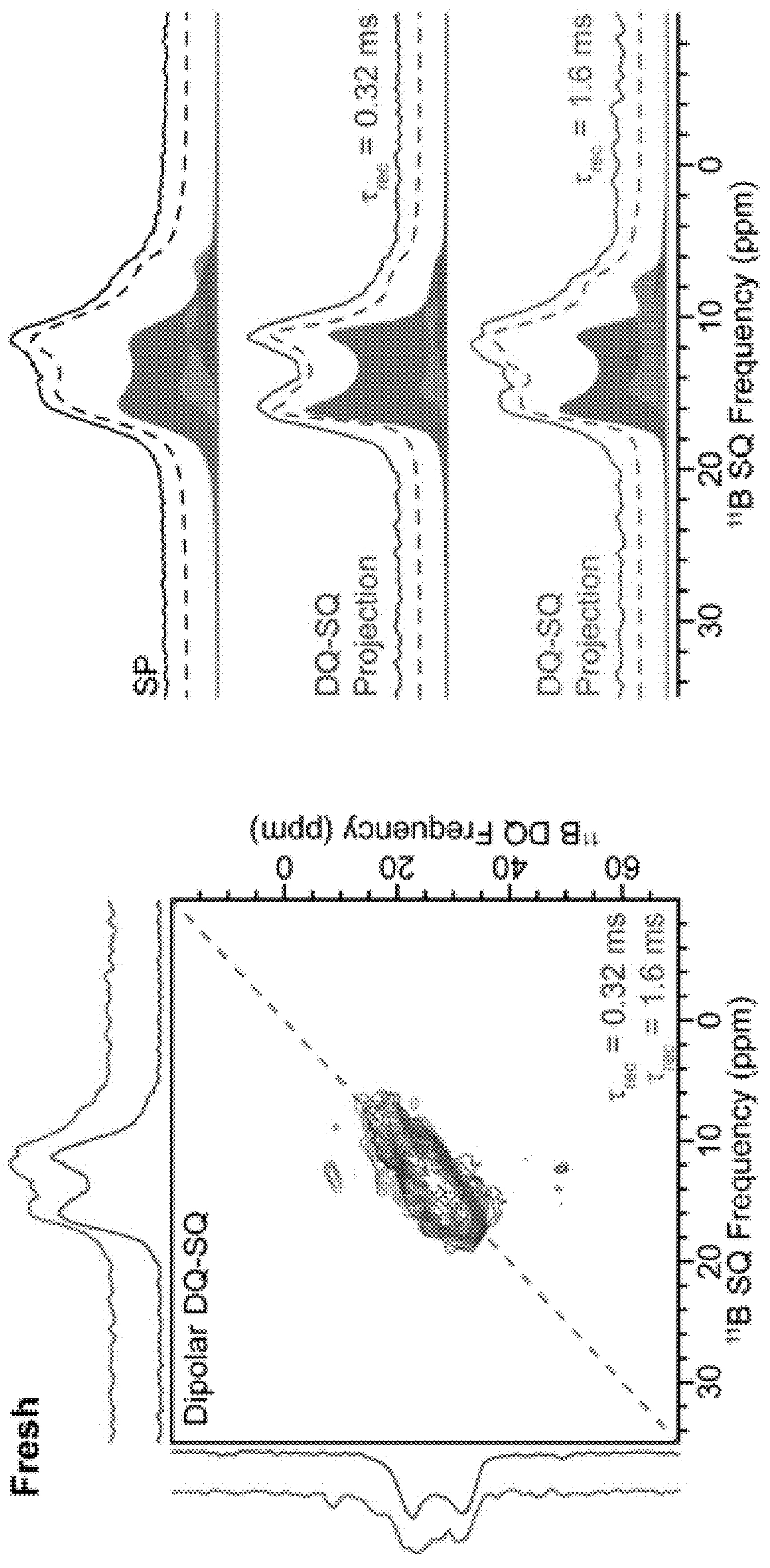
Figure 20B:
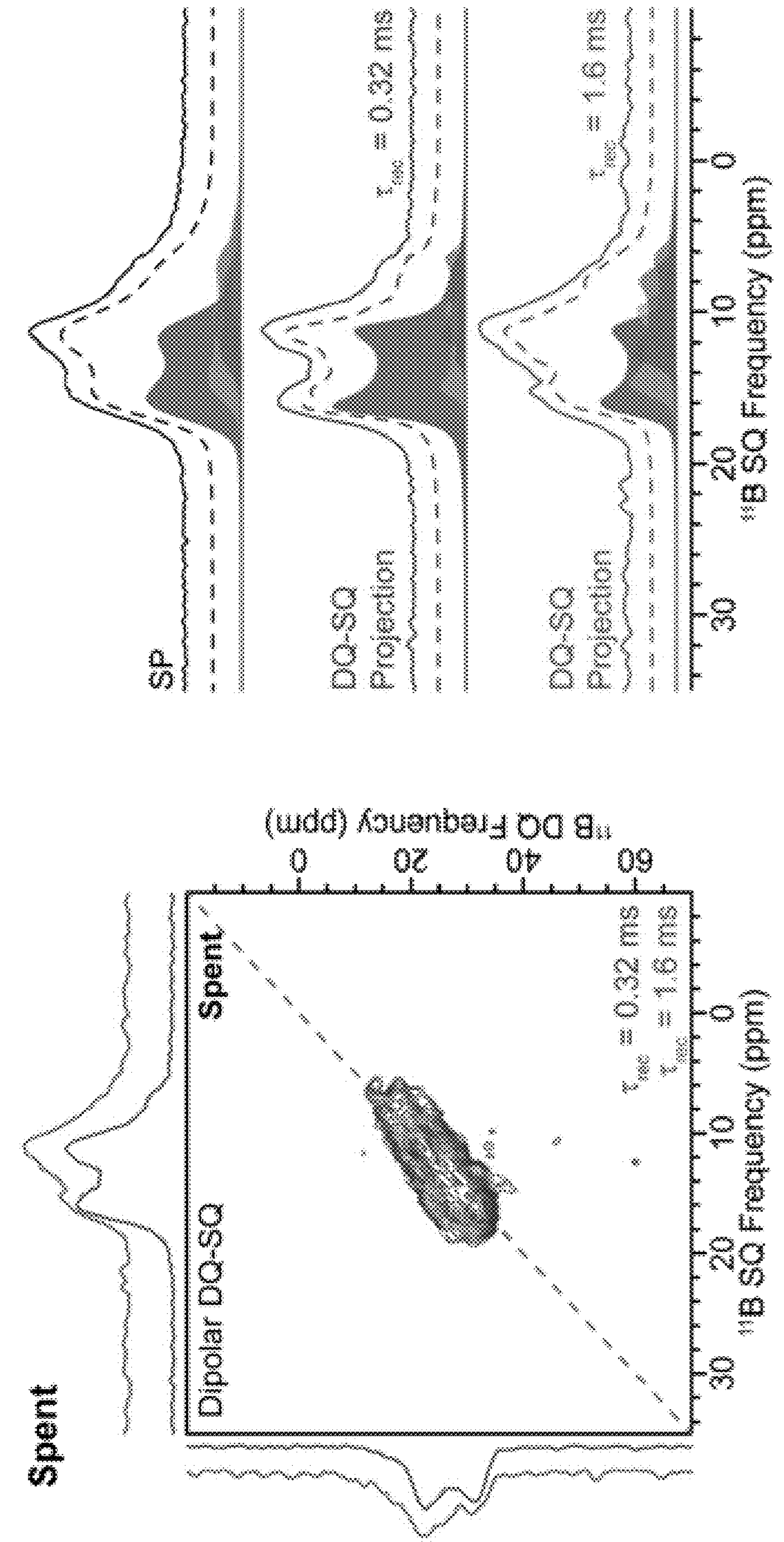

FIGS. 20A-20B (left) shows 2D $^{11}B$ dipolar double-quantum-single-quantum (DQ-SQ) spectra of (FIG. 20A) fresh and (FIG. 20B) spent B/OAC recorded with either (blue) 0.32 or (red) 1.6 ms of total $$BR2_2^1$$

homonuclear dipolar recoupling, 25 kHz MAS and $B_0$=14.1 T. FIG. 20 (right) shows Comparison of SP $^{11}B$ spectra with the $^{11}B$ direct dimension projections from the 2D DQ-SQ spectra. The solid and dashed lines correspond to experimental and analytically simulated spectra, respectively. The color of the fits correspond to the fits given in FIG. 4 and Table 1.

Figure 21:
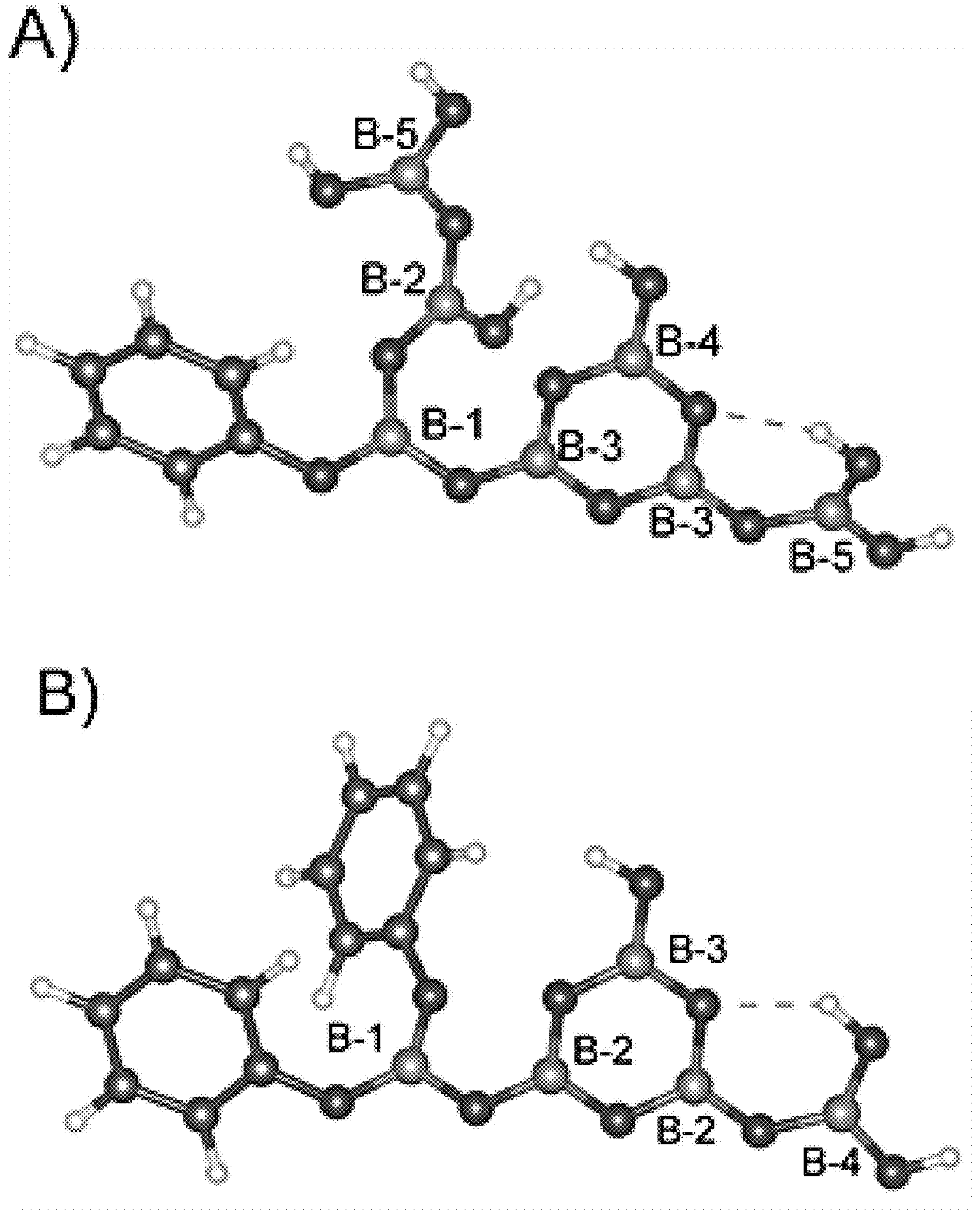
Figure 21:
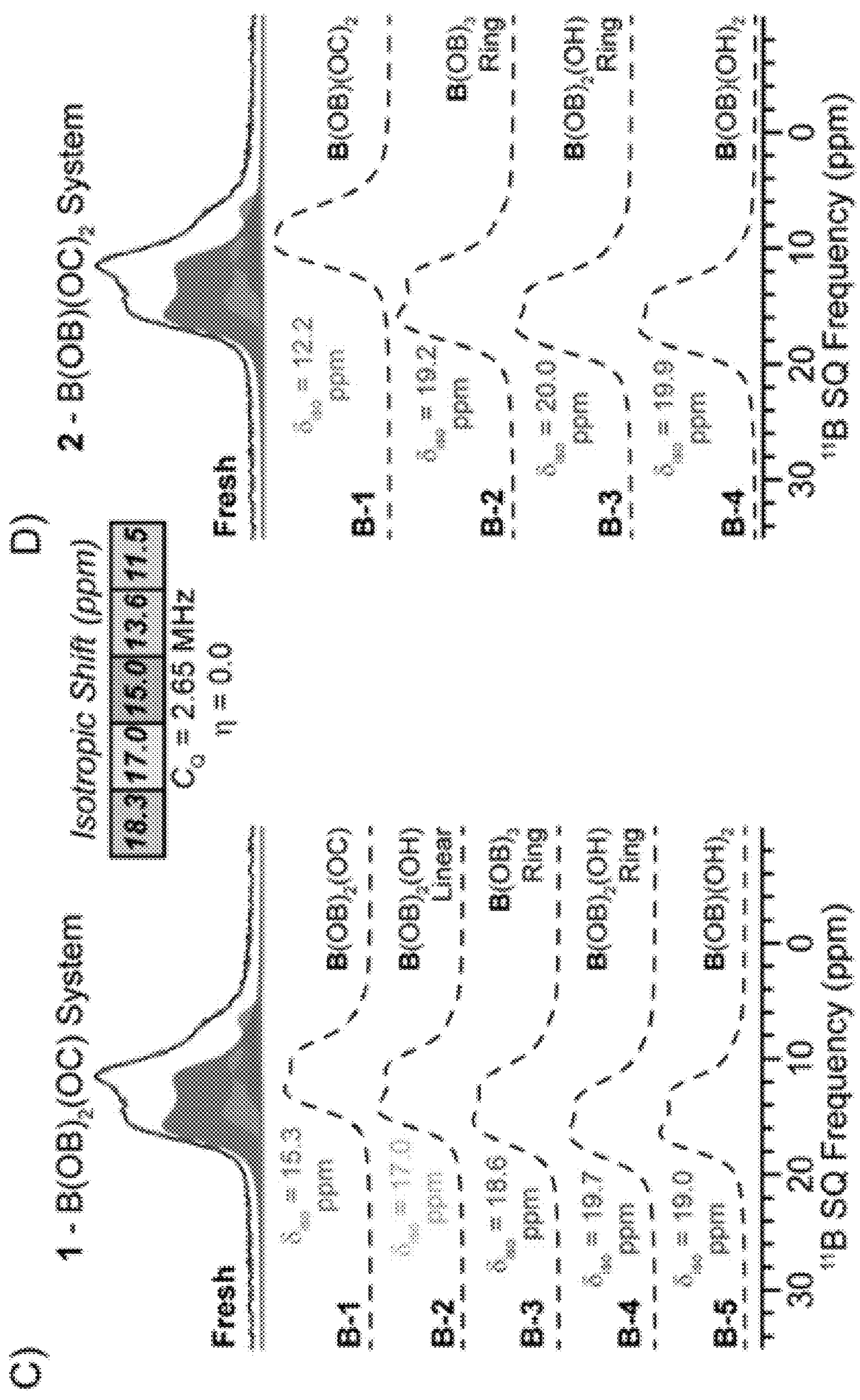

FIG. 21 shows (A, B) plane-wave DFT geometry optimized structures of model phenyl borate systems containing a (A) $B(OB)_2(OC)$ or (B) $B(OB)(OC)_2$ unit; white, green, brown and red balls correspond to H, B, C and P atoms, respectively. (C, D) Comparison of DFT predicted $^{11}B$ NMR spectra with the experimental $^{11}B$ NMR spectrum of fresh B/OAC. The boron atom labeling (i.e., B-1, B-2, etc.) corresponds with the labeling in the structure; structure (A) goes with spectra (C) and structure (B) goes with spectra (D). The exact $^{11}B$ NMR parameters ($d_{iso}$, $C_Q$ and h) are given in Table 2. Note, a few of the labels for the same boron species are duplicated (in (C), B-3 and B-5, in (D) B-2). The $^{11}B$ spectra shown here is the average of the two calculated parameters. Individual parameters are given in Table 2. Experimental and DFT spectra were recorded or simulated at $B_0$=14.1 T with 25 kHz MAS.

Figure 22:
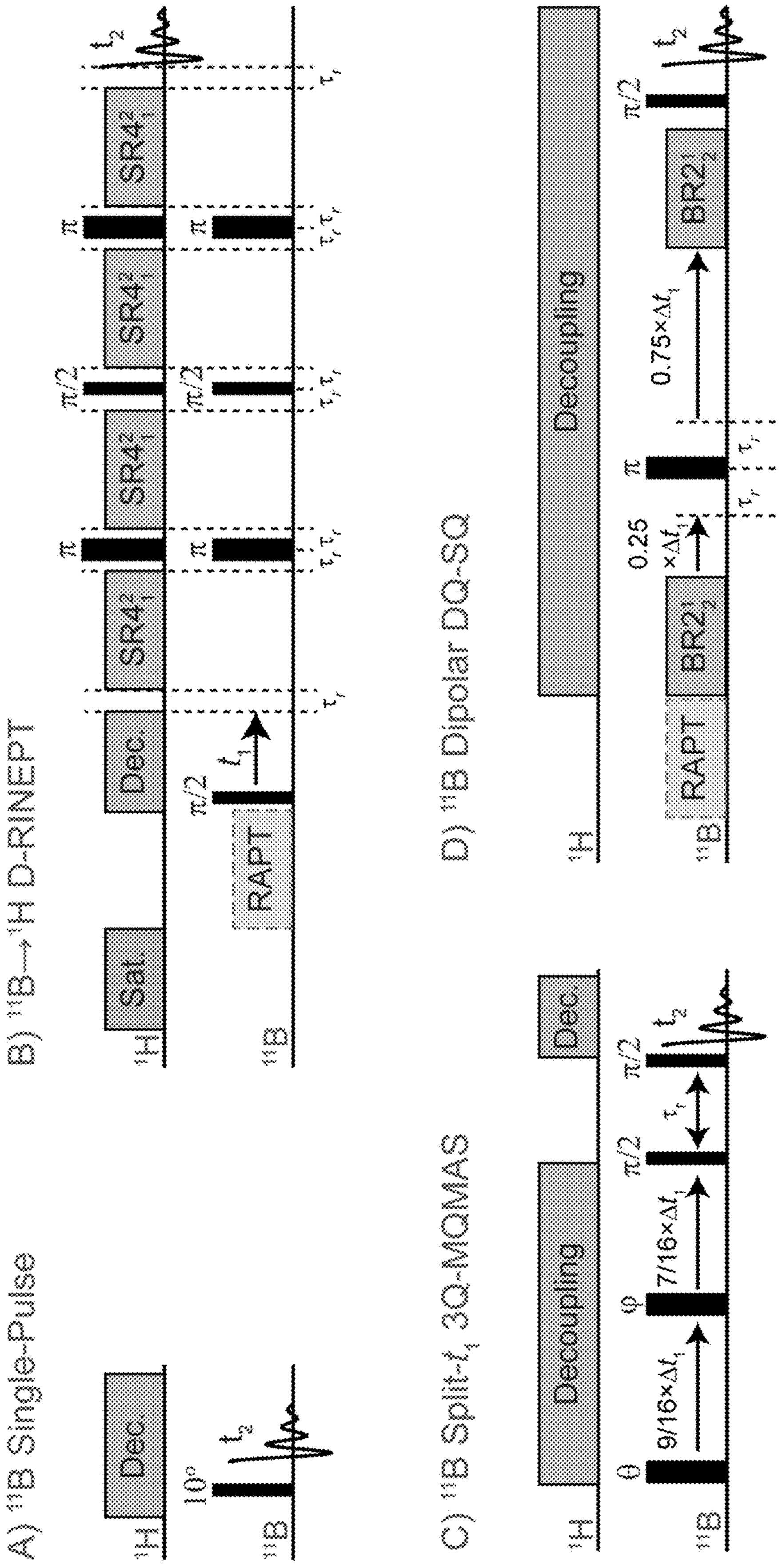

FIG. 22 shows schematic illustrations of (A) $^{11}B$ 10° single-pulse, (B) $^{11}B \rightarrow {}^{1}H$ D-RINEPT, (C) $^{11}B$ split-$t_1$ 3Q-MQMAS and (D) $^{11}B$ dipolar DQ-SQ NMR pulse sequences used in this work. (C) q and j correspond to 0Q→3Q excitation and 3Q→1Q reconversion pulse lengths.

While the disclosed methods and catalysts may include various modifications and alternative forms, specific embodiments are shown by way of example in the drawings and are described in detail herein. However, the description of specific embodiments herein is not intended to limit the invention to the particular forms disclosed, but on the contrary, the intention is to cover all modifications, equivalents, and alternatives falling within the spirit and scope of the invention as defined by the appended claims.

DETAILED DESCRIPTION

This disclosure is based on our discovery that the use of a boron-impregnated oxidized amorphous carbon catalyst facilitates improved oxidative dehydrogenation of alkanes, such as propane, to desired olefins, such as propene. Specifically, the disclosed methods exhibit high selectivity towards the desired product while decreasing the production of unwanted byproducts, such as CO and $CO_2$. Furthermore, the process occurs at relatively low temperatures, and the catalyst is stable over time, and does not need to be frequently regenerated. Furthermore, the disclosed catalysts exhibit a significantly improved induction period as compared to other boron-containing catalysts, and would be significantly less expensive to implement in large scale, industrial applications than other boron-containing catalysts.

This disclosure is not limited to the particular methodology, protocols, materials, and reagents described, as these may vary. Furthermore, the terminology used in this disclosure describes particular embodiments only, and is not intended to limit the scope of the present invention, which will be limited only by the language of the appended claims.

As used in this disclosure and in the appended claims, the singular forms "a", "an", and "the" include plural reference unless the context clearly dictates otherwise. The terms "a" (or "an"), "one or more" and "at least one" can be used interchangeably. The terms "comprising", "including", and "having" can also be used interchangeably.

Unless defined otherwise, all technical and scientific terms used in this disclosure, including element symbols, have the same meanings as commonly understood by one of ordinary skill in the art. Chemical compound names that are commonly used and recognized in the art are used interchangeably with the equivalent IUPAC name. For example, ethene is the same as ethylene, propene is the same as propylene, butene is the same as butylene, 2-methylpropane is the same as isobutane, and 2-methylpropene is the same as isobutene.

The following abbreviations are used throughout this disclosure: BN, boron nitride; B/OAC, boron-impregnated oxidized activated carbon; DH, dehydrogenation; h-BN, hexagonal form of boron nitride; NDC, Norit Darco 12×40 activated carbon; OAC, oxidized activated carbon; ODH, oxidative dehydrogenation; ODHP, oxidative dehydrogenation of propane; P, partial pressure for a given gas; S, selectivity for a given product; $WHSV^{-1}$, inverse weight-hour-space-velocity; % X, conversion for a given reactant.

All publications and patents specifically mentioned in this disclosure are incorporated by reference herein for all purposes, including for describing and disclosing the chemicals, instruments, statistical analysis and methodologies that are reported in the publications that might be used in connection with the disclosed methods and devices. All references cited in this disclosure are indicative of the level of skill in the art.

As demonstrated in the Examples, amorphous carbon may be oxidized by contacting the amorphous carbon with an oxidizing agent, such as nitric acid. The method used to oxidize the carbon is not limited to this process, and any method of oxidizing amorphous carbon could be used. For example, U.S. Pat. No. 4,371,454 discloses methods used to oxidize carbon to create spherical from pitch and amorphous carbon.

In another non-limiting example, ozone could be used to oxidize the amorphous carbon. Ozone oxidation forms hydroxyl, carbonyl, and —C—O— surface moieties, with —CH species being consumed and resulting in —COOH species (see Mawhinney, D. B. and Yates Jr. J. T. Carbon, 2001, 39, 1167-1173).

In yet another non-limiting example, hydrogen peroxide could be used to oxidize the amorphous carbon. Schlögl and Su (Phys. Chem. Chem. Phys. 2015, 17, 1567-1571) showed that $H_2O_2$ can successfully oxidize carbon nanotubes (CNTs), while inducing lower oxygen functionalities (carboxylic groups and anhydrides) than $HNO_3$. Carbon oxidation was conducted by autoclaving reduced CNT, water, and $H_2O_2$ at 100° C. for 4 hours (reduced CNT is HCl treated commercially available CNT).

The Examples also demonstrate that boron may be impregnated onto the oxidized amorphous carbon surface by exposing the surface to boron, such with boric acid in water solution. However, other methods for exposing the surface with boron and related boron oxide moieties may be used.

The Examples also demonstrate that the catalytic materials prepared from impregnation of oxidized amorphous carbon is an active and selective catalyst for ODH. Moreover the catalytic material exhibits equal propylene selectivity and improved productivity ($kg_{propylene}\ kg_{cat}^{-1}\ hr^{-1}$) as compared to h-BN.

The Examples are illustrative only, and do not limit the scope of the invention in any way. Indeed, various modifications of the invention in addition to those shown and described herein will become apparent to those skilled in the art from the foregoing description and the following examples and fall within the scope of the appended claims.

Definitions

As used herein, the term "amorphous carbon" refers to a carbon material without long-range crystalline order. The term "oxidized amorphous carbon" refers to amorphous carbon that undergo an oxidation reaction, which can be defined as the loss of electrons (or gain of oxygen, or loss of hydrogen) during a reaction by a molecule, atom, or ion. In some embodiment, oxidized amorphous carbon comprises one or more moieties selected from the group consisting of a carboxyl, a phenolic hydroxyl, a carbonyl, an anhydride, and a —C—O—.

As used herein, the term "carboxyl" refers to the functional group of the formula —C(O)OH (i.e. 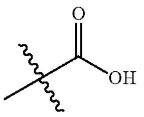 ).

As used herein, the term "phenolic hydroxyl" refers to the functional group of the formula —$C_6H_5OH$ (i.e. 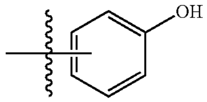 ).

As used herein, the term "carbonyl" refers to the functional group of the formula —C(O)—

(i.e. 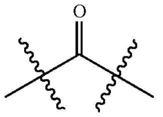 ).

As used herein, the term "anhydride" refers to the functional group of the formula —C(O)OC(O)—

(i.e. 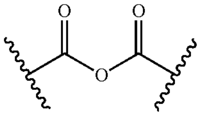 ).

In some embodiments, the oxidized amorphous carbon is oxidized activated carbon. As used herein, the term "activated carbon" refers to a type of purified, powdered charcoal that is treated physically or chemically to generate microfissures that vastly increase its adsorptive surface area available for adsorption or chemical reactions.

In some embodiments, the amorphous carbon is oxidized by an "oxidizing agent." As used herein, the term "oxidizing agent" refers to chemicals that have the ability to oxidize other compounds. In some embodiments, the oxidizing agent is nitric acid, ozone, or hydrogen peroxide.

As used herein, the term "impregnated" or "impregnation" refers to a procedure to load a given porous support (e.g. activated carbon) with a metal or metalloid component in (i) the solid-state way (i.e. physical mixture of both components in solid state) or (ii) more commonly via wet impregnation (i.e. physical mixture of the support in solid state and the metal or metalloid component dissolved in a liquid solution), in some embodiments, the boron is impregnated onto the surface of the oxidized amorphous carbon. In some embodiments, impregnating the surface of the oxidized amorphous carbon with boron is performed by contacting the oxidized amorphous carbon with excess boric acid.

As used herein, the term "3-coordinate boron species" refers to boron-containing group wherein the boron atom is bonded to three moieties and possesses a hybridization state of $sp^2$. The "3-coordinate boron species" typically have a molecular geometry of trigonal planar. The 3-coordinate boron species may be represented by OH, OB, or OC moieties. It should be understood that the moieties represented as OB or OC may have the boron or carbon atom bound to additional atoms (e.g., 2 or 3 additional atoms) to form the catalytic material. OH moieties may be typically found at the outer surface of the catalytic material. OC moieties may typically be found at the interface between the amorphous carbon and a layer of boron covering the oxidized amorphous carbon. OB moieties may typically be found within a layer of boron covering the oxidized amorphous carbon. The 3-coordinate boron species may comprise $B(OB)(OH)_2$, $B(OB)_2(OH)$, $B(OB)_3$, $B(OB)_2(OC)$, B(OB)(OC), $B(OC)_3$, or any combination thereof.

In some embodiments, the majority of 3-coordinate boron species are clustered. As used herein, the term "clustered" or "clusters" refers to a 3-carbon species that exhibit B—O—B bonds, e.g., $B(OB)(OH)_2$, $B(OB)_2(OH)$, or $B(OB)_3$. In some embodiments, between Clustered 3-coordinate boron species may form part of a cluster extending from the amorphous carbon or layer of boron covering the amorphous carbon having a multiplicity of layers of boron.

In some embodiments, between 60 and 90% of the plurality of 3-coordinate boron species are $B(OB)(OH)_2$, $B(OB)_2(OH)$, and $B(OB)_3$. In some embodiments, between 65 and 85% or between 70% and 80% of the plurality of 3-coordinate boron species are $B(OB)(OH)_2$, $B(OB)_2(OH)$, and $B(OB)_3$.

In some embodiments, between 40 and 70% of the plurality of 3-coordinate species are $B(OB)(OH)_2$ and $B(OB)_2(OH)$. In some embodiments, between 45 and 65%, between 50 and 65%, or between 55 and 65% of the plurality of 3-coordinate boron species are $B(OB)(OH)_2$ or $B(OB)_2(OH)$.

In some embodiments, the catalytic material comprises from 25 wt % to 40 wt % boron, based on the total weight of the catalytic material. In some embodiments, the catalytic material comprises from 25 wt % to 35 wt % boron, based on the total weight of the catalytic material.

In some embodiments, the catalytic material comprises a complete layer of boron covering the oxidized amorphous carbon. As used herein, the term "a complete layer of boron" refers to a layer containing 3-coordinate boron species comprising $B(OB)(OH)_2$, $B(OB)_2(OH)$, $B(OB)_3$, $B(OB)_2(OC)$, B(OB)(OC), and $B(OC)_3$, wherein the layer substantially surrounds the amorphous carbon. A complete layer of boron can surround and protect the underlying amorphous carbon from decomposition or combustion at elevated reaction temperatures. In contrast, an incomplete layer of boron may leave substantial portions of amorphous carbon vulnerable to decomposition or combustion at reaction temperatures.

As used herein, the term "oxidative dehydrogenation" refers to an oxidative process of dehydrogenating hydrocarbons (e.g. alkanes and hydrocarbons comprising an alkyl group) to corresponding olefinic counterparts in the presence of oxygen. When oxygen is co-fed with one of more liquid of gaseous reactant to act as a reactant, the reaction thermodynamics are altered such that the resulting net reaction is exothermic. Accordingly, the reaction can proceed at much lower reaction temperatures, resulting in decreased energy costs and increased catalyst stability. Oxygen in the feed stream also eliminates coke formation on the catalyst surface and thus creates no need for catalyst regeneration.

As used herein, the term "hydrocarbon" refers to an organic compound containing only hydrogen and carbon atoms. In some embodiments, the catalytic material is capable of catalyzing oxidative dehydrogenation (ODH) of an alkane or an alkyl group.

As used herein, the term "alkane" refers to saturated hydrocarbons having a formula of $C_nH_{2n+2}$, wherein n is a positive integer greater than or equal to 1. Examples of alkanes include, but are not limited to methane, ethane, n-propane, iso-propane, butane, etc. As used herein, the term "alkyl" refers to a saturated, straight or branched hydrocarbon chain radical. In some embodiment, the number of carbon atoms in an alkane or alkyl moiety is indicated by the prefix "$C_x$-$C_y$", wherein x is the minimum and y is the maximum number of carbon atoms in the substituent. Representative examples of alkyl include, but are not limited to, methyl, ethyl, n-propyl, iso-propyl, n-butyl, sec-butyl, isobutyl, tert-butyl, n-pentyl, isopentyl, neopentyl, etc.

As used herein, the term "olefin" refers to an unsaturated hydrocarbon containing at least one "C═C" double bond. The term "alkenyl" as used herein, refers to a straight or branched hydrocarbon chain containing at least one carbon-carbon double bond. Non-limiting examples of alkenyl include buta-1,3-dienyl, ethenyl, 2-propenyl, 2-methyl-2-propenyl, 3-butenyl, 4-pentenyl, 5-hexenyl, etc.

As used herein, the term "alkylbenzene" refers to benzene attached to at least one alkyl group as described herein. Non-limiting examples of alkylbenzene refers to methylbenzene, ethylbenzene, propylbenzene, etc. In some embodiments, the one or more liquid or gaseous reactants comprise an alkylbenzene, such as ethylbenzene.

As used herein, the term "induction period" refers to the initial slow phase of a chemical reaction which later accelerates. In some embodiments, the catalytic material has an ODH induction period of less than 12 hours. In some embodiments, the catalytic material has an ODH induction period of less than 11, 10, 9, or 8 hours.

As used herein, the term "thermally stable" refers to the ability of a compound or material to resist the action of heat and to maintain its physical and chemical properties. In some embodiments, the catalytic material is thermally stable at a temperature equal to or less than 600° C. In some embodiments, the catalytic material is thermally stable at a temperature equal to or less than 550° C., or equal to or less than 500° C.

As used herein, the term "inert atmosphere" refers to a reaction atmosphere which is composed mainly of chemically inactive gases. Common chemically inert gases include but are not limited to argon and nitrogen.

EXAMPLES

Example 1: Oxidative Dehydrogenation of Propane to Propene Using the B/OAC Catalyst Bulk boron materials, such as hexagonal boron nitride (h-BN), are highly selective catalysts for the oxidative dehydrogenation of propane (ODHP). Previous attempts to improve the productivity of these systems involved the immobilization of boron on silica and resulted in less selective catalysts. Here, we report that acid-treated, activated carbon-supported boron prepared via incipient wetness impregnation with boric acid (B/OAC) exhibits equal propylene selectivity and improved productivity ($kg_{propylene}$ $kg_{cat}^{-1}$ $hr^{-1}$) as compared to h-BN. Characterization of the fresh and spent catalysts with infrared, Raman, X-ray photoelectron, and solid-state NMR spectroscopies reveals the presence of oxidized/hydrolyzed boron that is clustered on the surface of the support.

Introduction.

Boron-containing materials have been shown to be high performing for the oxidative dehydrogenation (ODH) of light alkanes to light olefins.[1-6] In particular, bulk and nanotubular hexagonal boron nitride (h-BN) exhibit benchmark-high selectivity towards propylene for the ODH of propane (e.g., ca. 85% at 9% conversion), significantly outperforming previous state-of-the-art silica-supported vanadium oxide ODH catalysts (61% at 9% conversion).[11] The enhanced performance of h-BN for ODH is attributed to an amorphous oxidized/hydrolyzed boron layer [$B_2(OH)_{2x}O_{3-x}$, x=0-3] which resides on the BN sheets.[2,7-10] Solid-state NMR spectroscopy and other surface characterization techniques have shown that the amorphous oxidized/hydrolyzed boron layer is primarily composed of 3-coordinate boron oxide/hydroxide species ($B_2(OH)_{2x}O_{3-x}$, x=0-3) that form under reaction conditions.[2,9,11,12] Ultra-high field $^{11}B$ NMR spectroscopy revealed that the oxidized/hydrolyzed boron layer grows off the BN sheets through $BN_2O$ groups, where the O atom is bridging to the oxidized/hydrolyzed boron layer.[12] Notably, h-BN does not appear to deactivate but features an induction period for optimal catalytic performance, suggesting that the oxidized/hydrolyzed boron layer provides the active species.[1,5,8,11] This is in agreement with previous quantum chemical calculations that suggested clustering of boron oxide/hydroxide species are required for ODH.[10]

Figure 2A:
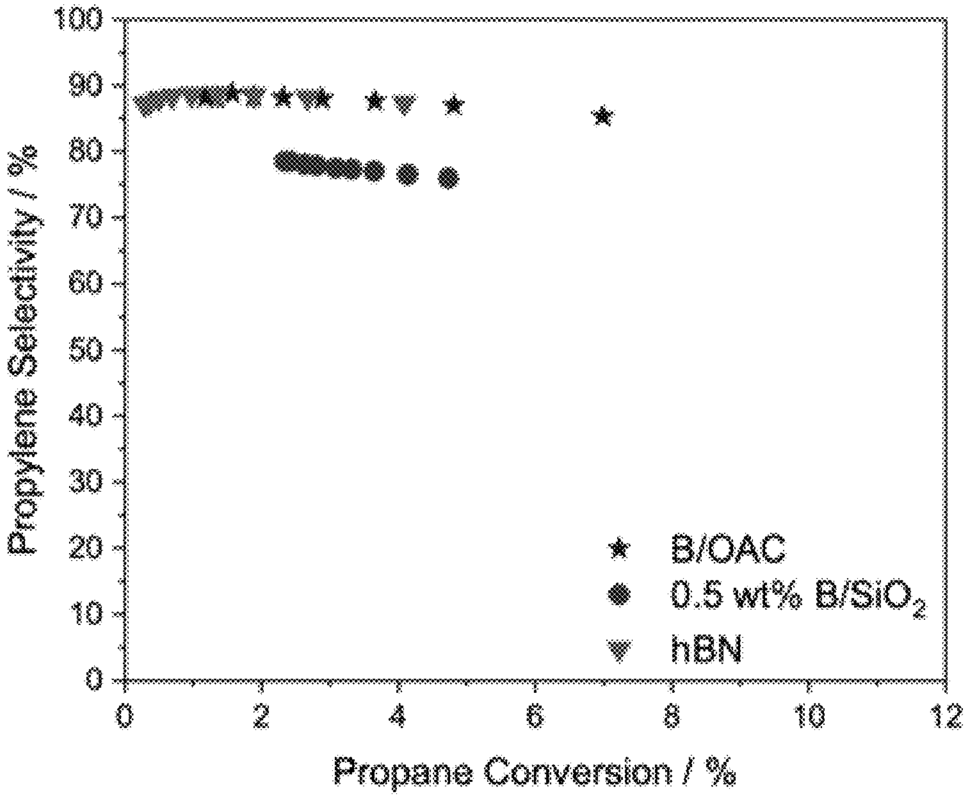
FIG. 2A is a graph illustrating propylene selectivity versus propane conversion data for ODH of propane over (stars) B/OAC, (triangles) h-BN, and (circles) 0.5 wt % $B/SiO_2$ at 500° C. $O_2$ conversion was held at 10% for 7% propane conversion and remained below 10% for all other conversions. Different conversions were achieved by changing the gas flow rate between 40 and 200 mL $min^{-1}$ (30% propane, 15% $O_2$, 55% nitrogen).
Figure 2B:
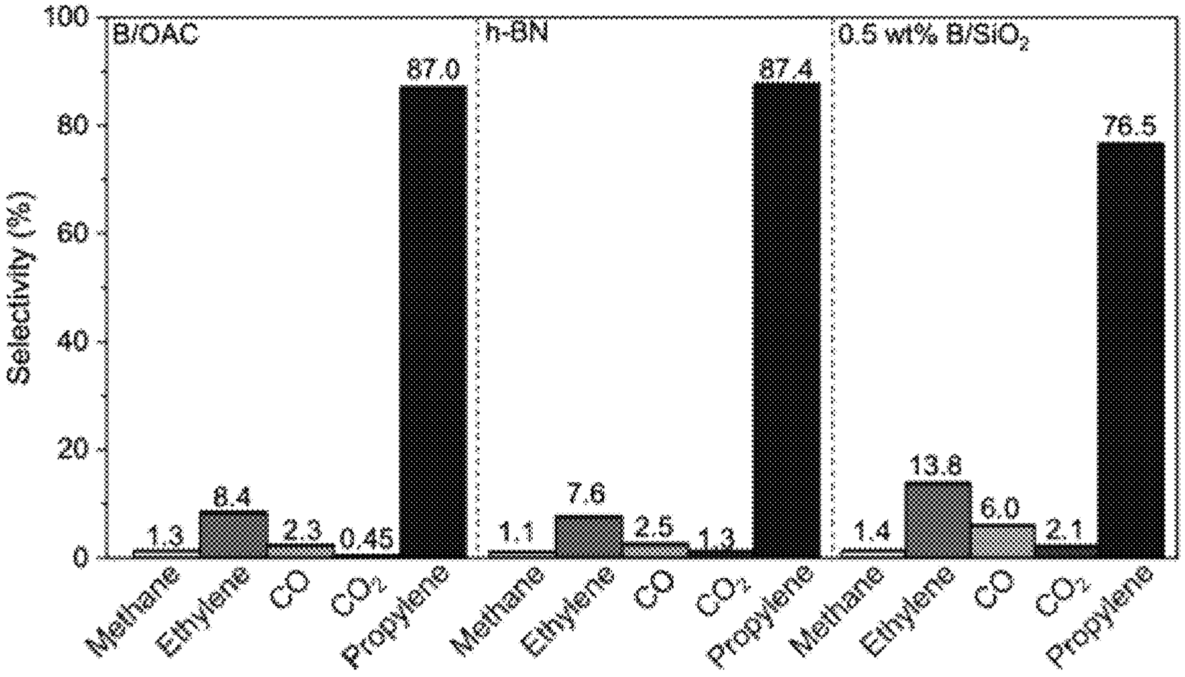
FIG. 2B is a bar graph illustrating product distribution comparison at isoconversion (ca. 5% propane conversion) for (left to right) B/OAC, h-BN, and 0.5 wt % $B/SiO_2$ at 500° C.

Further investigation of oxidized/hydrolyzed boron oxide species for ODH have been conducted through the synthesis and characterization of silica-supported boron oxide materials ($B/SiO_2$).[5,13] Detailed characterization of $B/SiO_2$ ODH catalysts showed that the majority of boron is composed of clustered 3-coordinate boron oxide/hydroxide species [$B_2(OH)_{2x}O_{3-x}$, x=0-3], likely representing similar species observed in h-BN ODH catalysts.[5,12,13] Alternatively, an MCM-22 zeolite isomorphously substituted with boron primarily contains $B(OSi)_3$ species isolated in the zeolite framework and is inactive for ODH. This observation further supports the hypothesis that the clustering of oxidize/hydrolyzed boron gives rise to its ODH catalytic activity.[12,14] However, $B/SiO_2$ catalysts show worse selectivity for ODH of propane to propylene than h-BN ($B/SiO_2$: 76.5%, h-BN: 87.4%; FIG. 2B), which is attributed to oxygen functionalities on the silica surface that induce unwanted side reactions with intermediates.[5] Silica, while alone is inert, has been shown to induce unwanted side reactions in the presence of boron by previous studies that demonstrated that a physical mixture of silica and h-BN has a negative effect on propylene selectivity.[5] In addition, ca. 50% of boron leaches from the 1 wt. % $B/SiO_2$ catalysts over 24-hours of ODH catalysis.[5] The leaching of boron is likely attributed to the use of a silica support, on which boron significantly restructures under reaction conditions.[5]

Figure 1:
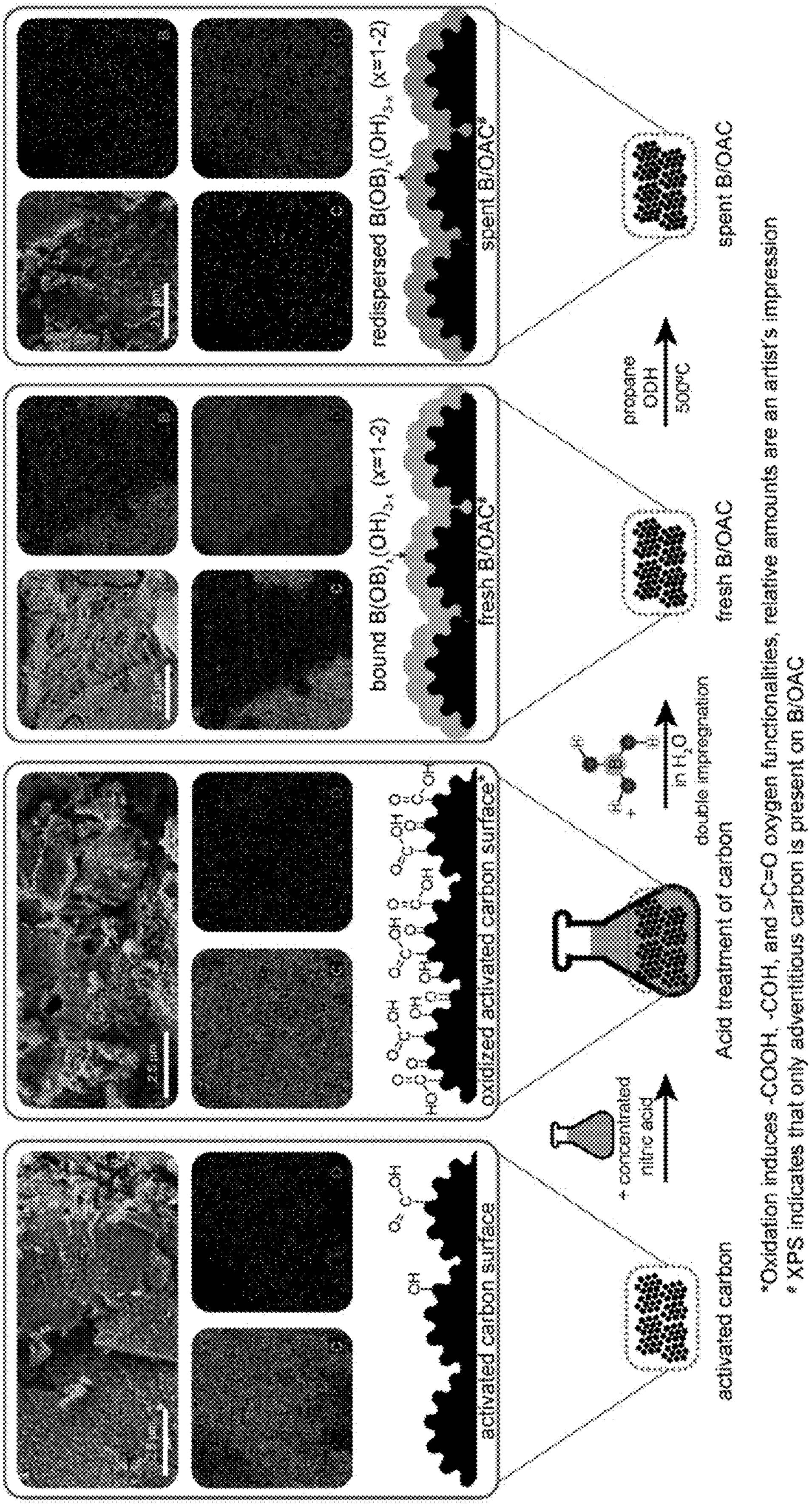
FIG. 1 is a schematic illustration for the synthesis of the B/OAC catalyst and SEM/EDX microscopy of the denoted carbon sample.

Here, the Examples demonstrate the use of activated carbon, treated with nitric acid and impregnated with boric acid as a boron source (referred to as B/OAC, FIG. 1). We characterize the B/OAC materials with scanning electron microscopy and a combination of infrared (IR), Raman, X-ray photoelectron, and solid-state NMR spectroscopies to develop an understanding of the boron sites on these materials.

Experiments, Results and Discussion

Activated carbons have long been used as catalyst supports.[15-24] Further, amorphous carbon itself has shown significant activity and selectivity for ODH reactions (i.e. ethylbenzene to styrene, isobutane to isobutene, 2-butanol to 2-butanone, and ethanol to acetaldehyde), while structured, stable carbons (i.e. carbon nanotubes, carbon nanofibers, nanodiamonds, onion-like carbons, etc.) have been used for more challenging substrates like propane.[25-32] However, amorphous carbon-based catalysts have not been explored for propane ODH, likely due to the combustion of the material at the required reaction conditions (500° C.).[33-36] Structured carbon surfaces are often functionalized by chemical treatments to induce thermal stability under oxidative conditions (FIG. 4[6-14] This is done by inducing surface functional groups, such as —OH and —COOH, with an oxidizing treatment (e.g. nitric acid).[6-14] These functionalities are anchoring sites for boron precursors, thus giving the ability for carbon to support greater quantities of active sites, but also restricting the surface mobility of the species. By inducing anchor site oxygen functionalities and impregnating the material with excess boron, combustible carbon sites on the support are likely eliminated. Indeed, a boron overlayer is formed as shown by SEM-EDX (FIG. 1) and C1s XPS (FIG. 6), where boron is well-dispersed across the catalyst surface and only adventitious carbon is present, respectively. The catalyst was found to be thermally stable where B/OAC experienced mass gain as a result of a 24 h pretreatment and up to 12 h under reaction at 500° C. under oxidizing conditions (199.2 mg prior to reaction, 205.6 mg post-reaction) and TGA showed minimal weight loss (FIG. 7). Additionally, we examined B/C (no acid oxidation) at low and high weight loadings. At low weight loadings, reaction data could not be collected due to complete combustion of the support during the 24-hour pretreatment. At high weight loadings, the catalyst exhibited high propylene selectivity (85% propylene at 2.0% conversion) however significant combustion occurred, resulting in loss of nearly half the catalyst (200 mg prior to reaction, 122.4 mg post-reaction).

The Examples demonstrate the unprecedented selectivity to alkenes in ODH reactions is not exclusive to bulk boron materials but can be achieved by amorphous carbon-supported boron oxide. Boron-coated oxygen-functionalized carbon (ca. 28 wt % B) catalyzes propane ODH and produces near identical product distribution trends to h-BN (FIG. 2) and other bulk boron materials.[1,2] To ensure that we were exploring ODH, $O_2$ conversion was kept below 10%. Further, we confirmed that the reaction orders in $C_3H_8$ and $O_2$ for B/OAC are similar to that of h-BN, indicating that the reaction mechanism are analogous over the two materials (FIG. 8).[1,4] B/OAC was found to be more selective towards propylene than $B/SiO_2$ (FIG. 2), however it is important to note that the weight loadings between the two materials are significantly different. It is not possible to explore low weight loading B/OAC or high weight loading $B/SiO_2$ due to catalyst combustion and limited anchoring sites, respectively. We have attempted low weight loading B/C and nearly all the material was consumed under reaction conditions. Similarly, we previously attempted high weight loading $B/SiO_2$ and were only able to achieve 1.7 wt % B likely due to limited number of silanol anchoring sites, in addition to leaching that further reduces the boron content.[5] While the two materials are not direct comparisons, important information such as support effects, or lack thereof due to the boron overlayer, can be extracted from the reactor data. For example, B/OAC exhibits a linear trend (similar to h-BN) for propane conversion as a function of contact time while propane conversion for $B/SiO_2$ levels off with increasing contact time (FIG. 9). The linear conversion-contact time trend of B/OAC indicates that the carbon support is uninvolved in the reaction, unlike silica.

B/OAC and bulk boron catalysts, namely h-BN, only differ in their rates of propane consumption, productivity, and induction periods (FIGS. 9-12). B/OAC was ca. 35% more reactive and ca. 54% more productive than h-BN. Further, analysis of the propane conversion as a function of catalyst time-on-stream shows that B/OAC reaches apparent steady-state much more quickly (ca. 8 h) than h-BN (10-20 h) and $B/SiO_2$ (ca. 24 h) (FIG. 11). It is hypothesized that this steady-state conversion correlates with the boron content after 24 h and the induction period is a required amount of time for the catalyst to achieve its stable active state. For other supported boron catalysts, the induction period involves the leaching of weakly bound boron species from the surface, however NMR and ICP analysis indicate that minimal boron leaching occurs during catalysis with B/OAC (FIG. 17). This was attributed to the increased hydrophobicity of the B/OAC material as compared to other supported boron catalysts (e.g. $B/SiO_2$, FIG. 7). Rather than leaching, the induction period for B/OAC is attributed to a redistribution of the boron overlayer (SEM in FIG. 1). This is confirmed by differential scanning calorimetry (DSC, FIG. 14), where a broad, endothermic peak appears at temperatures above 325° C., indicating material restructuring. Further, prior computational work suggests that boron, under reaction conditions, is highly mobile and undergoes restructuring.[10] The reduced induction time suggests that the initial structure of the fresh sample is nearer to the stable active phase required for propane ODH than h-BN and $B/SiO_2$. It should be noted that while B/OAC is only a slightly more efficient catalyst than bulk h-BN for ODHP, B/OAC is also cheaper than h-BN.

Figure 3A:
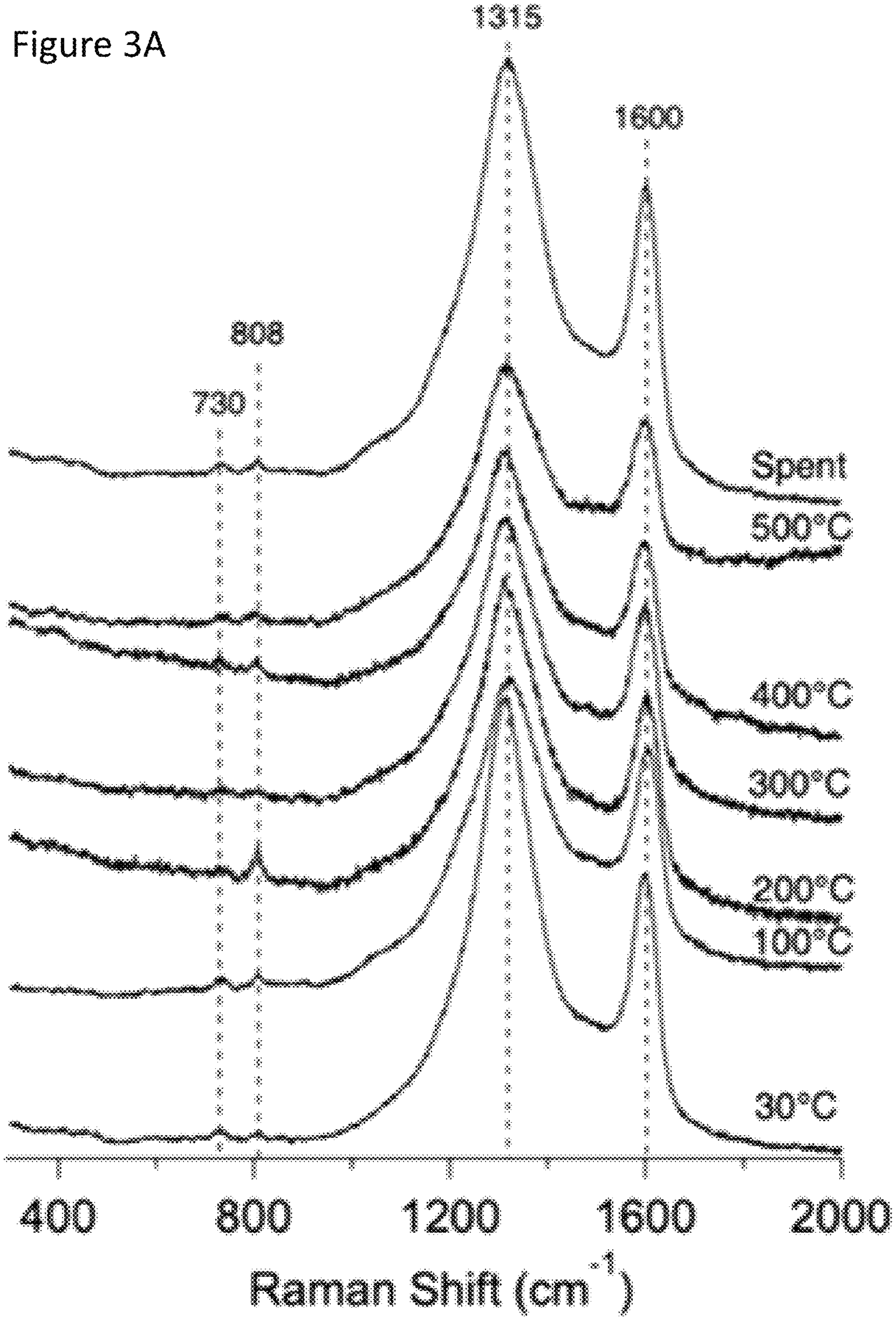
FIG. 3A is a graph illustrating in situ Raman study of the dehydration of fresh B/OAC to 500° C. in air. The top spectrum (labeled spent) is of spent B/OAC taken after catalysis.

Due to the reduced induction period and the hypothesis that fresh B/OAC is nearer to the stable active phase for propane ODH than h-BN and $B/SiO_2$, spectroscopic characterization is necessary for the advancement of boron-based catalysts. Fresh and spent B/OAC catalysts were characterized through a combination of solid-state NMR, infrared (IR), Raman, and X-ray photoelectron spectroscopies (XPS). XPS spectra of the B is region of fresh and spent B/OAC catalysts both display a broad, slightly asymmetric signal centered at ca. 194-195 eV, in the general region for boron oxide/hydroxide type species (FIG. 15).[2,5] The near identical XPS spectra of the fresh and spent catalysts suggest similar species are present in both materials, consistent with $^{11}B$ solid-state NMR spectroscopy spectra discussed below. Raman spectra of fresh B/OAC were recorded during in situ dehydration up to 500° C. in air and compared to the spent material (FIG. 3*a*). All Raman spectra display peaks at ca. 730 and 808 $cm^{-1}$ (indicative of agglomerated and chain-type metaborate species), 1315, and 1600 $cm^{-1}$ (consistent with disordered (D) and graphitic (G) peaks, respectively from the carbon support).[44-46] Consistent with XPS, the Raman spectra of fresh and spent B/OAC are near identical, regardless of temperature (FIG. 3*a*). However, it is important to note that while the induction period is hypothesized to redistribute the boron phase to its active state, this may only be present under reaction conditions (500° C., 40-200 mL $min^{-1}$ of propane, $O_2$, and $N_2$).[10] Upon removal of gases and cooling down of the system, the boron phase redistributes to its initial state.

It was previously reported that ODHP catalytic activity was not reliant on the surface area of the boron-containing catalyst, but rather due to differences in active site densities and/or electronic interactions between the catalyst surface and the bulk structure.[15] For example, for vanadium oxide ODHP catalysts, it was found that support material can exert variable electronic influence on the active $VO_4$ sites on the surface and affect the observed rate. Here, we attribute the superior observed rate and productivity of $B/SiO_2$ to electronic interactions between the active site and support.

Figure 3B:
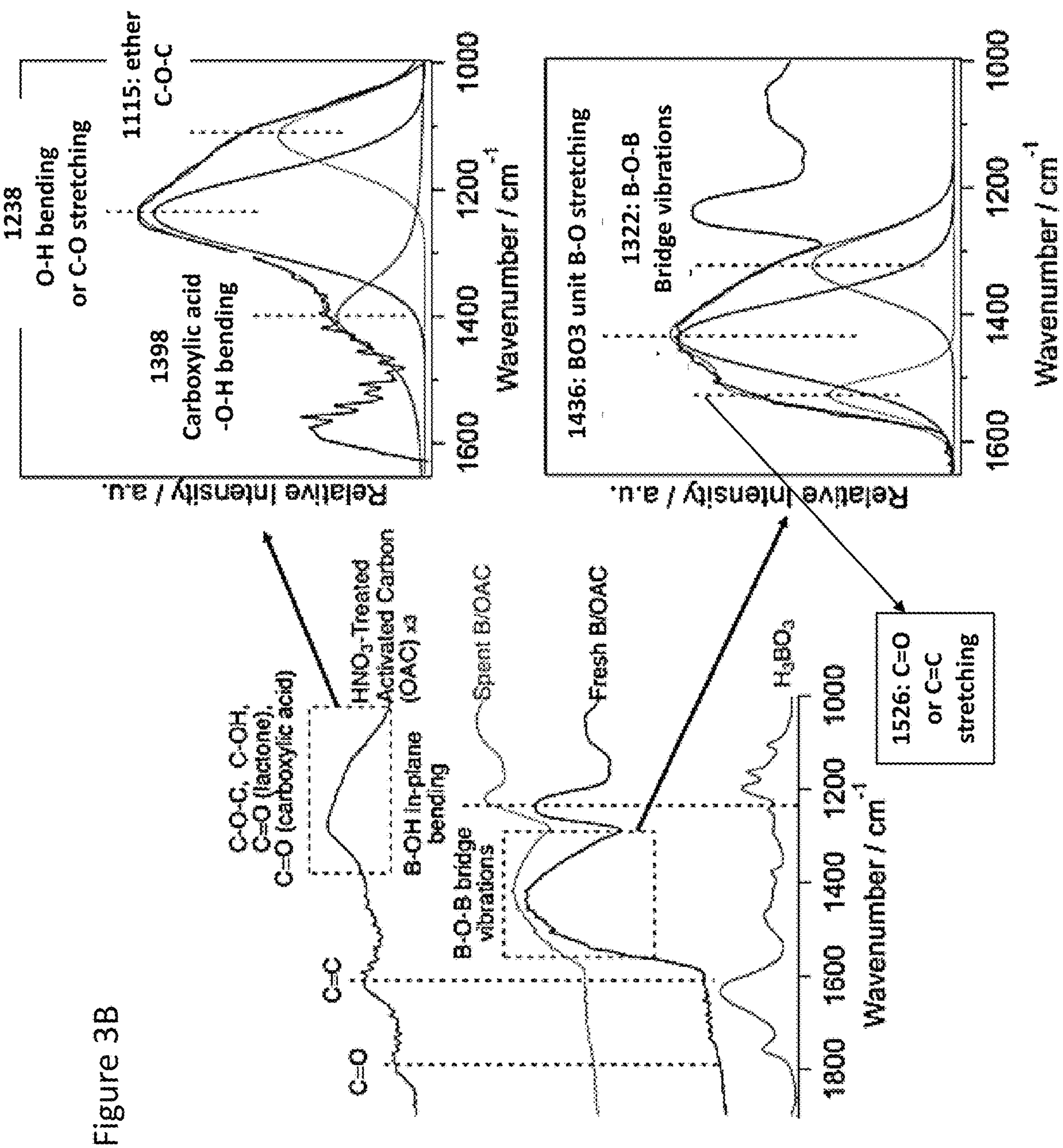
FIG. 3B is a graph illustrating DRIFTS spectra of fresh and spent B/OAC, OAC, and $H_3BO_3$ between 1000-1900

Diffuse reflectance infrared Fourier transform spectroscopy (DRIFTS) spectra of fresh and spent B/OAC, OAC (no boron), and $H_3BO_3$ (boric acid) were recorded to further probe surface structure and the incorporation of boron onto the carbon support (FIG. 3*b*, S11). All samples were dehydrated in the DRIFTS cell by heating under dry air to 200° C. for 30 minutes before cooling to room temperature for data collection. Both fresh and spent B/OAC, as well as the OAC, have a strong, asymmetric peak centered at 3260 $cm^{-1}$ (FIG. 16). The feature is representative of —OH stretching vibrations either from B—OH and/or C—OH species residing in the oxidized/hydrolyzed boron cluster or on the surface of the carbon support.[47,48] The B/OAC (fresh and spent) and OAC materials both exhibit minor peaks between 2800-3000 $cm^{-1}$ which are attributed to aliphatic C—H stretching from the carbon support (FIG. 16).

DRIFTS spectra of B/OAC and OAC differ significantly in the low wavenumber regime, where vibrations at 1220 $cm^{-1}$ and a broad peak between 1290 and 1580 $cm^{-1}$ are seen in both fresh and spent B/OAC, while OAC exhibits peaks centered at ca. 1240, 1580, and 1756 $cm^{-1}$ (FIG. 3B). These modes in fresh and spent B/OAC are consistent with B—OH in plane bending (1290 $cm^{-1}$) and B—O—B bridge vibrations of metaborate-type species (1580 $cm^{-1}$), respectively.[48-50] The deconvolution of the broad peak centered at ca. 1580 $cm^{-1}$ shows that three features are apparent at 1322, 1436, and 1526 $cm^{-1}$ (FIG. 3B). These are attributed to B—O—H deformations[49,51-54], B—O stretching of $BO_3$ units 153-551, and C═C stretching from the support, respectively[47]. On non-borated OAC, the features at 1756 and 1580 $cm^{-1}$ are assigned to C═O and conjugated aromatic C═C functional groups, respectively.[47,56] It is important to note that C═O peak at 1756 $cm^{-1}$ is absent in B/OAC (fresh and spent), suggesting a high fraction of C═O sites on the surface of the carbon support are consumed by boron during impregnation of $H_3BO_3$ (FIG. 1). Deconvolution of the broad OAC peak at 1240 $cm^{-1}$ results in 3 species at 1115, 1238, and 1398 $cm^{-1}$ (FIG. 4*b*). These are attributed to oxygen functionalities of ether C—O—C[56], O—H bending or C—O stretching[47], and carboxylic acid —O—H bending[57]. Much of this broad peak appears to be consumed following boron impregnation as evidenced by the absence of such a peak in the fresh and spent B/OAC spectra, corroborating the observation that boron consumes C═O/C—O species on the surface of the carbon support.

Magic-angle spinning (MAS) $^{11}B$ solid-state NMR spectroscopy (ex-situ) was used to further probe structure within fresh and spent B/OAC heterogenous catalysts and identify the type of boron species formed on the surface of the carbon support. All solid-state NMR spectroscopy experiments were performed at $B_0$=14.1 T with 25 kHz MAS. Quantitative single-pulse (recycle delay>5×$T_1$, 10° tip-angle) $^{11}B$ solid-state NMR spectra of the fresh and spent catalysts show near identical NMR signals in the typical region of 3-coordinate $BO_3$ containing species (FIG. 5*a*).[5,12,58-60] In fact, the absolute $^{11}B$ NMR signal intensities for the fresh and spent catalysts are near identical, suggesting minimal boron leaching (FIG. 17). This observation is in agreement with the XPS and Raman spectra, as well as ICP which suggest that boron loading is 28.0±0.5 wt. % before and after catalysis. 2D $^{11}B$ triple-quantum multiple-quantum magic-angle spinning (3Q-MQMAS) NMR experiments were performed on the fresh and spent catalysts to identify all boron species. This is because the indirect dimension of a 2D MQMAS spectrum reveals NMR signals that are free of second-order quadrupolar broadening and the peak positions are determined by the isotropic chemical shift ((iso) and quadrupolar induced shift (QIS).[61-63] The 2D $^{11}B$ Q-MQMAS NMR spectra of fresh and spent B/OAC are near identical, further suggesting that similar species are present before and after catalysis (FIG. 4B-C).

A simultaneous analytical fit of the $^{11}B$ 3Q-MQMAS and single-pulse direct excitation NMR spectra reveals that there are five unique boron species with quadrupolar coupling constants ($C_Q$) of 2.65 MHz and $d_{iso}(^{11}B)$ of (blue fit) 18.3 ppm, (orange fit) 17.0 ppm, (brown fit) 15.0 ppm, (green fit) 13.6 ppm and (pink fit) 11.5 ppm (FIG. 5A-B). The observed $\delta_{iso}(^{11}B)$ and $C_Q$ are consistent with 3-coordinate $BO_3$ containing species; $B(OB)_3$ and $B(OSi)_3$ groups found in B/$SiO_2$ exhibit $\delta_{iso}$ ($^{11}B$) of ca. 16 and 10 ppm, respectively.[5,12,58-60] Therefore, based on the $C_Q$ and $\delta_{iso}(^{11}B)$, all boron species are covalently bonded to 3 O-atoms, taking the general form of $BO_3$. Below, 2D $^1H$—$^{11}B$ heteronuclear correlation (HETCOR) and $^{11}B$ homonuclear correlation spectra are used to identify which atoms are bonded to the B—O O-atoms (e.g. B—O—H, B—O—B or B—O—C), enabling the determination of molecular structure. Due to the similarities in the fresh and spent catalysts, we focus on the solid-state NMR characterization of only the fresh catalysts. Note that the exact same NMR experiments were performed on the spent catalysts and the spectra are given in the Supporting Information.

$^1H$—$^{11}B$ dipolar-based HETCOR NMR experiments were performed to identify boron species in close-spatial proximity to hydrogen atoms (FIG. 5, 18). Short durations of dipolar recoupling will selectively probe species with short H—B internuclear distances as the dipolar coupling constant ($D_{ij}$) between two spins is proportional to the inverse cube of their internuclear distance ($D_{ij} \propto r_{ij}^{-3}$); longer durations of dipolar recoupling will enable the observation of species with longer H—B internuclear distances. A 2D $^{11}B \rightarrow {}^1H$ dipolar-refocused INEPT (D-RINEPT)[64,65] NMR spectrum recorded with a short duration (total recoupling time=0.64 ms) of $$SR4_1^2$$

heteronuclear dipolar recoupling applied to the $^1H$ spins reveal correlations between a broad $^1H$ NMR signal centered at ca. 5 ppm and the $^{11}B$ NMR signal at $d_{iso}(^{11}B)$=18.3 ppm (FIG. 5A, blue). The short duration of dipolar recoupling ensures only species with B—OH functionalities are observed, illustrating that the $^{11}B$ NMR signal at $d_{iso}(^{11}B)$=18.3 ppm contains 1 or 2 —OH groups [i.e. $BO_x(OH)_{3-x}$ (x=1, 2)]; the $^1H$ NMR signal at ca. 5 ppm is assigned to HO—B hydroxyl species. As the total dipolar recoupling duration is increased to 2.24 ms, the $^1H$ NMR signal centered at ca. 5 ppm mainly show correlations to the $^{11}B$ NMR signal at $\delta_{iso}(^{11}B)$=18.3 ppm (FIG. 5A, red). Closer examination of the $^{11}B$ D-RINEPT projection shows that the lower frequency $^{11}B$ NMR signals also correlate to the HO—B $^1H$ species at ca. 5 ppm and the D-RINEPT projection starts to resemble that of the single-pulse direct excitation $^{11}B$ NMR spectrum (FIGS. 5B and 19). This suggests that the $^{11}B$ species at $\delta_{iso}(^{11}B)$=15-17 ppm are proximate to the B—OH H-atom, likely by having 1 or more B—O—B bond(s) to the $BO_x(OH)_{3-x}$ (x=1, 2) B-atom at $\delta_{iso}(^{11}B)$=18.3 ppm.

Next, homonuclear $^{11}B$ dipolar double-quantum-single-quantum (DQ-SQ) correlation experiments were performed to identify boron species in close spatial proximity to other boron atoms.[12,67,68] As mentioned above, the 1D single-pulse and 2D 3Q-MQMAS spectra revealed all boron species take the general formula of $BO_3$. Therefore, the $^{11}B$ dipolar DQ-SQ experiments will reveal boron species with B—O—B bonds as two $^{11}B$ spins are required to generate the observed DQ-coherence.[69] 2D $^{11}B$ dipolar DQ-SQ spectra of fresh B/OAC were recorded with either 0.32 or 1.6 ms of total $$BR2_2^1$$

homnuclear dipolar recoupling[70] applied to the $^{11}B$ spins (FIG. 20). Unfortunately, the signal overlap between all $^{11}B$ NMR signals is large at $B_0$=14.1 T which hinders the unambigous determination of B—O—B connectivity between all sites. Significantly stronger magnetic fields are required to decrease the signal broadening by the quadrupolar interaction to enable the observation of all homonuclear correlations.[12] Nevertheless, analytical simulations of the $^{11}B$ SQ projections reveal that all $^{11}B$ NMR signals except at $d_{iso}(^{11}B)$=11.5 ppm come through the DQ-filter. While the connectivity between the boron species at $\delta_{iso}(^{11}B)$=13.5-18.3 ppm cannot be determined through the 2D spectra due to significant signal overlap, the observation of those $^{11}B$ NMR signals in the $^{11}B$ SQ projection reveals they all contain at least 1 B—O—B bond. As the $^{11}B$ NMR signal at $\delta_{iso}(^{11}B)$=11.5 ppm was never observed, it suggests no B—O—B bonds are present for that species. It is well known that the $\delta_{iso}(^{11}B)$ decreases as B—O—B units are replaced with B—O—Si bonds for boron oxide on silica or zeolites, where $B(OB)_3$ and $B(OSi)_3$ species typically resonates at $\delta_{iso}(^{11}B)$~16-18 ppm and 10-12 ppm, respectively.[5,12,14,59,60] Therefore, based on the high $\delta_{iso}(^{11}B)$ and strong correlations observed in the $^1H$—$^{11}B$ HETCOR (with short duration of recoupling) and $^{11}B$ homonuclear correlation spectra, we assign the $^{11}B$ NMR signal at $\delta_{iso}(^{11}B)$=18.3 ppm to $B(OB)_x(OH)_{3-x}$ (x=1 or 2) (Table 1). The lower frequency $^{11}B$ NMR signals only showed $^1H$—$^{11}B$ correlations at long durations of dipolar recoupling, suggesting close spatial proximity to the $B(OB)_x(OH)_{3-x}$ (x=1 or 2) species. In addition, the $^{11}B$ NMR signals at $\delta_{iso}(^{11}B)$=13.5-17.0 ppm were observed in the 2D $^{11}B$ DQ-SQ homonuclear correlation spectra, revealing B—O—B functionality. Following the logic that the $\delta_{iso}(^{11}B)$ decreases as B—O—B units are replaced with B—O—Si, the $^{11}B$ NMR signals at $\delta_{iso}(^{11}B)$=13.5, 15.0 and 17.0 ppm correspond to $B(OB)(OC)_2$, $B(OB)_2(OC)$ and $B(OB)_3$, respectively (Table 1). Similarly, the $^{11}B$ NMR signal at $\delta_{iso}(^{11}B)$=11.5 ppm is assigned to $B(OC)_3$ as no correlations were observed in the $^1H$-$^{11}B$ HETCOR and $^{11}B$ homonuclear correlation spectra (Table 1). Plane-wave density functional theory (DFT) calculations were performed on model phenyl borate systems to further aid in the assignment of the experimental $^{11}B$ NMR spectra (FIG. 21). Indeed, DFT predicts that the $\delta_{iso}(^{11}B)$ decreases by ca. 2-3 ppm as B—OB/H (i.e., B—OB or B—OH) units are replaced with B—OC while $C_Q$ remains relatively constant, corroborating our $^{11}B$ NMR assignment above (FIG. 21 and Table 2). Analytical simulations of the quantitative single-pulse $^{11}B$ NMR spectra of fresh and spent B/OAC were used to determine the population each boron species (FIG. 4A, Table 1). As expected from the discussions above, the populations of all boron species are relatively similar between the fresh and spent catalysts. Interestingly, $B(OB)_x(OH)_{3-x}$ (x=1 or 2) sites make up ca. 60% of all boron in the fresh catalysts (ca. 50% in spent catalysts), illustrating that majority of boron contains 1 or 2 hydroxyl groups (B—OH). In addition, $B(OB)_3$ species make up ca. 20% of the population, showing that ca. 80% of boron is clustered (i.e. exhibits B—O—B bonds) on the surface of the carbon support. Based on B/OACs high-boron weight loading (28 wt. %) and the observation that ca. 80% of boron is clustered (i.e. $B(OB)_x(OH)_{3-x}$ (x=1 or 2) and $B(OB)_3$; corresponding to a ca. weight loading of 22%), there is likely a complete layer of boron covering the surface of B/OAC, consistent with the SEM/EDX images that reveal a homogenous distribution of boron across the carbon support. In addition, as mentioned above, B/OAC prepared with low-boron weight loadings undergoes extensive combustion, consistent with the interpretation that B/OAC (28 wt. % B) gives complete surface coverage of boron oxide/hydroxide. The $B(OB)_2(OC)$ and $B(OB)(OC)_2$ species make up just under 20% of boron in the fresh material. These $B(OB)_2(OC)$ and $B(OB)(OC)_2$ sites likely connect the clustered $B(OB)_x(OH)_{3-x}$ (x=1 or 2) and $B(OB)_3$ species to the surface of the carbon support, which is supported by the observation of $B(OB)_2(OC)$ and $B(OB)(OC)_2$ species correlating to B—OH $^1H$ NMR signals in the $^{11}B \rightarrow ^1H$ D-RINEPT spectrum recorded with a long duration of recoupling. The $B(OC)_3$ groups make up a minuscule fraction of boron (ca. 2 and 6% for the fresh and spent materials), suggesting that only a minor component of boron is isolated on the carbon support. We note that DRIFTS spectra revealed that majority of C═O/C—O groups on the surface of the carbon support were consumed during impregnation with $H_3BO_3$. Comparison with solid-state NMR spectroscopy suggest that the $B(OB)_2(OC)$ and $B(OB)(OC)_2$ boron atoms likely attach to the surface of the carbon through C═O/C—O species. Further investigation of the $B(OB)_2(OC)$, $B(OB)(OC)_2$ and $B(OC)_3$ species, as well as the surface of the carbon support, will be conducted through $^{13}C$ and $^{17}O$ solid-state NMR spectroscopy on $^{13}C$ and $^{17}O$-enriched materials.

TABLE 1

Boron Speciation and Populations[a] Determined by Solid-State NMR Spectroscopy.

| Boron Species[b] | 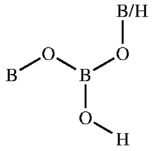 | 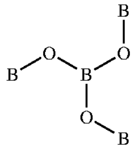 | 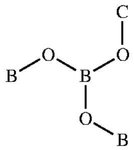 | 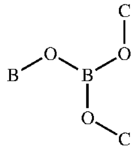 | 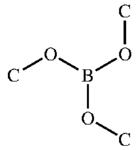 |
|---|---|---|---|---|---|
| $\delta_{iso}$ (ppm)[c] | 18.3 | 17.0 | 15.0 | 13.6 | 11.5 |
| Fresh Population (%) | 60 | 19 | 7 | 12 | 2 |
| Spent Population (%) | 51 | 17 | 11 | 15 | 6 |

[a]Populations were determined from the quantiative (recyle delay > $5 \times T_1$) 10° tip-angle single pulse spectra.
[b]The color of the highlighted boron atom corresponds to the color of the analyitical fits given in FIG. 5.
[c]All boron species have $C_Q$ = 2.65 MHz and h = 0.

TABLE 2

Plane-wave DFT calculated $^{11}B$ NMR parameters of model phenyl borate systems.

| Key[a] | σ (ppm) | $\delta_{iso}$ (ppm)[b] | $C_{Q,\ calc.}$ (MHz) | $C_{Q,\ corr.}$ (MHz)[c] | η |
|---|---|---|---|---|---|
| 1 - $B(BO)_2(OC)$ System | | | | | |
| B-1 | 80.73 | 15.30 | 2.73 | 2.45 | 0.18 |
| B-2 | 78.78 | 17.02 | 2.90 | 2.61 | 0.13 |
| B-3a[d] | 77.22 | 18.40 | 2.95 | 2.65 | 0.28 |
| B-3b[d] | 76.76 | 18.81 | 2.94 | 2.64 | 0.33 |
| B-4 | 75.73 | 19.72 | 2.89 | 2.60 | 0.31 |
| B-5[d] | 77.73 | 17.95 | 2.80 | 2.52 | 0.04 |
| B-5[d] | 75.2 | 20.19 | 2.83 | 2.54 | 0.28 |
| 2 - $B(BO)(OC)_2$ System | | | | | |
| B-1 | 84.18 | 12.25 | 2.5 | 2.25 | 0.29 |
| B-2a[d] | 75.85 | 19.61 | 3.1 | 2.79 | 0.23 |
| B-2b[d] | 76.71 | 18.85 | 2.95 | 2.65 | 0.32 |
| B-3 | 75.34 | 20.07 | 2.88 | 2.59 | 0.29 |
| B-4 | 75.57 | 19.86 | 2.81 | 2.53 | 0.28 |

[a]Key corresponds to B atoms in FIG. 21A and 21B.
[b]$d_{iso}(^{11}B)$ calculated via a calibration curve with the following equation: $\delta_{iso} = -0.8845\sigma + 86.704$.[20]
[c]DFT calculated $^{11}B$ $C_Q$ were corrected via a calibration curve with the following equation: $C_{Q,\ corr.} = 0.8987 C_{Q,\ calc.}$.[20]
[d]Two of the same boron species exist in each structure (see FIG. S16); a and b correspond to the two different units (average $d_{iso}(^{11}B)$, $C_Q$ and h of the two are given in FIG. S16 simulated spectra).

Conclusion

Oxidized activated carbon-supported boron (B/OAC) was shown to be an active and highly selective catalyst for the oxidative dehydrogenation of propane to propylene. The B/OAC catalyst yielded excellent selectivity towards propylene and is the most selective supported boron catalysts reported thus far, where it exhibited nearly the same product distribution as h-BN. Furthermore, B/OAC is significantly cheaper than h-BN, making it potentially economically more viable. Reactivity data indicated that B/OAC did not experience support interactions that result in reduced selectivity, as in $B/SiO_2$, likely as a result of a boron overlayer stabilizing and coating the carbon support. Molecular level characterization through XPS, IR, Raman and solid-state NMR spectroscopies revealed that the B/OAC material under atmospheric conditions contains clustered oxidized/hydrolyzed boron species residing on the surface of the carbon support. Spectroscopic analysis of B/OAC before and after catalysis reveals minimal differences, suggesting that while the boron structure may change under reaction conditions, the material reverts back to its initial state upon removal of heat and reactants. 2D $^{11}B$ MQMAS solid-state NMR spectra of the fresh and spent catalysts revealed five unique boron species: $B(OB)_x(OH)_{3-x}$ (x=1-2), $B(OB)_3$, $B(OB)_2(OC)$, $B(OB)(OC)_2$ and $B(OC)_3$. 2D $^1H$—$^{11}B$ HETCOR and $^{11}B$ homonuclear correlation solid-state NMR spectra aided in the assignment of all NMR signals. Lastly, analytical fits of quantitative $^{11}B$ solid-state NMR spectra illustrated that $B(OB)_x(OH)_{3-x}$ (x=1-2) and $B(OB)_3$ species make up ca. 80% of all boron, confirming that the majority of boron is clustered on the surface of the carbon support. This work demonstrates that carbon-supported boron oxide is a promising catalyst for the oxidative dehydrogenation of propane while confirming mechanistic hypotheses.

REFERENCES FOR EXAMPLE 1

[1] J. T. Grant, C. A. Carrero, F. Goeltl, J. Venegas, P. Mueller, S. P. Burt, S. E. Specht, W. P. McDermott, A. Chieregato, I. Hermans, *Science* 2016, 354, 1570-1573.
[2] J. T. Grant, W. P. McDermott, J. M. Venegas, S. P. Burt, J. Micka, S. P. Phivilay, C. A. Carrero, I. Hermans, *ChemCatChem* 2017, 9, 3623-3626.
[3] P. Chaturbedy, M. Ahamed, M. Eswaramoorthy, *ACS Omega* 2017, 3, 369-374.
[4] L. Shi, Y. Wang, B. Yan, W. Song, D. Shao, A.-H. H. Lu, *Chem. Commun.* 2018, 54, 10936-10946.
[5] A. M. Love, M. C. Cendejas, B. Thomas, W. P. McDermott, P. Uchupalanun, C. Kruszynski, S. P. Burt, T. Agbi, A. J. Rossini, I. Hermans, *J. Phys. Chem. C* 2019, 123, 27000-27011.
[6] W. D. Lu, D. Wang, Z. Zhao, W. Song, W. C. Li, A. H. Lu, *ACS Catal.* 2019, 9, 8263-8270.
[7] L. Shi, B. Yan, D. Shao, F. Jiang, D. Wang, A. H. Lu, Chin. *J. Catal.* 2017, 38, 389-395.
[8] Y. Zhou, J. Lin, L. Li, X. Pan, X. Sun, X. Wang, *J. Catal.* 2018, 365, 14-23.
[9] A. M. Love, B. Thomas, S. E. Specht, M. P. Hanrahan, J. M. Venegas, S. P. Burt, J. T. Grant, M. C. Cendejas, W. P. McDermott, A. J. Rossini, et al., *J. Am. Chem. Soc.* 2019, 141, 182-190.
[10] J. M. Venegas, Z. Zhang, T. O. Agbi, W. P. McDermott, A. Alexandrova, I. Hermans, Angew. *Chem., Int. Ed.* 2020, 59, 16527-16535.
[11] L. Shi, D. Wang, W. Song, D. Shao, W.-P. P. Zhang, A.-H. H. Lu, *ChemCatChem* 2017, 9, 1-7.
[12] R. W. Dorn, M. C. Cendejas, K. Chen, I. Hung, N. R. Altvater, W. P. McDermott, Z. Gan, I. Hermans, A. J. Rossini, *ACS Catal.* 2020, 10, 13852-13866.
[13] W. D. Lu, D. Wang, Z. Zhao, W. Song, W. C. Li, A. H. Lu, *ACS Catal.* 2019, 9, 8263-8270.
[14] N. Altvater, R. Dorn, M. Cendejas, W. McDermott, B. Thomas, A. Rossini, I. Hermans, Angew. *Chem. Int. Ed.* 2020, 132, 1-6.
[15] E. Nikolla, A. Holewinski, J. Schwank, S. Linic, *J. Am. Chem. Soc.* 2006, 128, 11354-11355.
[16] J. Zhang, D. Su, A. Zhang, D. Wang, R. Schlögl, C. Hébert, Angew. *Chem. Int. Ed.* 2007, 46, 7319-7323.
[17] A. Thomas, A. Fischer, F. Goettmann, M. Antonietti, J. O. Müller, R. Schlögl, J. M. Carlsson, *J. Mater. Chem.* 2008, 18, 4893-4908.
[18] J. Zhang, J. O. Müller, W. Zheng, D. Wang, D. Su, R. Schlögl, *Nano Lett.* 2008, 8, 2738-2743.
[19] K. Chizari, I. Janowska, M. Houllé, I. Florea, O. Ersen, T. Romero, P. Bernhardt, M. J. Ledoux, C. Pham-Huu, *Appl. Catal., A* 2010, 380, 72-80.
[20] B. Frank, A. Rinaldi, R. Blume, R. Schlögl, D. S. Su, *Chem. Mater.* 2010, 22, 4462-4470.
[21] A. Marinkas, F. Arena, J. Mitzel, G. M. Prinz, A. Heinzel, V. Peinecke, H. Natter, *Carbon* 2013, 58, 139-150.
[22] E. Lam, J. H. T. Luong, *ACS Catal* 2014, 4, 3393-3410.
[23] R. Arrigo, M. E. Schuster, Z. Xie, Y. Yi, G. Wowsnick, L. L. Sun, K. E. Hermann, M. Friedrich, P. Kast, M. Hävecker, et al., *ACS Catal.* 2015, 5, 2740-2753.
[24] L. M. Esteves, H. A. Oliveira, F. B. Passos, *J. Ind. Eng. Chem.* 2018, 65, 1-12.
[25] M. F. R. Pereira, J. J. M. Órfão, J. L. Figueiredo, *Appl. Catal. A* 1999, 184, 153-160.
[26] M. F. R. Pereira, J. J. M. Órfão, J. L. Figueiredo, *Appl. Catal. A* 2001, 218, 307-318.
[27] G. Mestl, N. I. Maksimova, N. Keller, V. V. Roddatis, R. Schlögl, Angew. *Chem. Int. Ed.* 2001, 40, 2066-2068.
[28] N. Keller, N. I. Maksimova, V. V Roddatis, M. Schur, G. Mestl, Y. V Butenko, V. L. Kuznetsov, R. Schlogl, *Angew. Chem. Int. Ed.* 2002, 41, 1885-1888.

[29] T. J. Zhao, W. Z. Sun, X. Y. Gu, M. Rønning, D. Chen, Y. C. Dai, W. K. Yuan, A. Holmen, *Appl. Catal. A* 2007, 323, 135-146.
[30] V. Schwartz, W. Fu, Y. T. Tsai, H. M. Meyer, A. J. Rondinone, J. Chen, Z. Wu, S. H. Overbury, C. Liang, *ChemSusChem* 2013, 6, 840-846.
[31] F. Herold, S. Prosch, N. Oefner, K. Brunnengräber, O. Leubner, Y. Hermans, K. Hofmann, A. Drochner, J. P. Hofmann, W. Qi, et al., *Angew. Chem. Int. Ed.* 2021, 2-11.
[32] W. Qi, D. Su, *ACS Catal.* 2014, 4, 3212-3218.
[33] J. W. Shim, S. J. Park, S. K. Ryu, *Carbon* 2001, 39, 1635-1642.
[34] G. Zhang, S. Sun, D. Yang, J. P. Dodelet, E. Sacher, *Carbon* 2008, 46, 196-205.
[35] T. A. Saleh, *Appl. Surf Sci.* 2011, 257, 7746-7751.
[36] I. Ud, M. S. Shaharun, D. Subbarao, A. Naeem, 2016, 42, 966-970.
[37] J. Collins, T. Ngo, D. Qu, M. Foster, *Carbon* 2013, 57, 174-183.
[38] V. Gómez-Serrano, M. Acedo-Ramos, A. J. López-Peinado, C. Valenzuela-Calahorrro, *Thermochim. Acta* 1997, 291, 109-115.
[39] M. Takaoka, H. Yokokawa, N. Takeda, *Appl. Catal. B Environ.* 2007, 74, 179-186.
[40] J. Jaramillo, P. M. Álvarez, V. Gómez-Serrano, *Fuel Process. Technol.* 2010, 91, 1768-1775.
[41] J. Zawadzki, *Carbon* 1980, 18, 281-285.
[42] J. T. Grant, C. A. Carrero, A. M. Love, R. Verel, I. Hermans, *ACS Catal.* 2015, 5, 5787-5793.
[43] A. M. Love, C. A. Carrero, A. Chieregato, J. T. Grant, S. Conrad, R. Verel, I. Hermans, *Chem. Mater.* 2016, 28, 5495-5504.
[44] T. Jawhari, A. Roid, J. Casado, *Carbon* 1995, 33, 1561-1565.
[45] E. I. Kamitsos, M. A. Karakassides, G. D. Chryssikos, *J. Phys. Chem.* 1987, 91, 1073-1079.
[46] T. Sekiya, N. Mochida, A. Ohtsuka, A. Soejima, *J. Non. Cryst. Solids* 1992, 151, 222-228.
[47] U. J. Kim, C. A. Furtado, X. Liu, G. Chen, P. C. Eklund, *J. Am. Chem. Soc.* 2005, 127, 15437-15445.
[48] J. Romanos, M. Beckner, D. Stalla, A. Tekeei, G. Suppes, S. Jalisatgi, M. Lee, F. Hawthorne, J. D. Robertson, L. Firlej, et al., *Carbon* 2013, 54, 208-214.
[49] L. Jun, X. Shuping, G. Shiyang, *Spectrochim. Acta Part A Mol. Spectrosc.* 1995, 51, 519-532.
[50] L. Zhou, H. Lin, W. Chen, L. Luo, *J. Phys. Chem. Solids* 2008, 69, 2499-2502.
[51] T. R. Gilson, 1991, 2463-2466.
[52] L. Andrews, T. R. Burkholder, *J. Chem. Phys.* 1992, 97, 7203-7210.
[53] S. C. Baidoc, I. Ardelean, *Mod. Phys. Lett. B* 2010, 24, 51-58.
[54] O. Floweri, H. Jo, Y. Seo, N. Lee, *Carbon* 2018, 139, 404-414.
[55] D. W. McKee, C. L. Spiro, E. J. Lamby, *Carbon* 1984, 22, 507-511.
[56] P. U. Karanjkar, S. P. Burt, X. Chen, K. J. Barnett, M. R. Ball, M. D. Kumbhalkar, X. Wang, J. B. Miller, I. Hermans, J. A. Dumesic, et al., *Cat. Sci. Technol.* 2016, 6, 7841-7851.
[57] S. Aldrich, "IR Spectrum Table & Chart," 2021.
[58] S. Kroeker, J. F. Stebbins, *Inorg. Chem.* 2001, 40, 6239-6246.
[59] S. J. Hwang, C. Y. Chen, S. I. Zones, *J. Phys. Chem. B.* 2004, 108, 18535-18546.
[60] Y.-T. A. Wong, D. L. Bryce, Annu. Rep. *NMR Spectrosc.* 2018, 93, 213-279.
[61] A. Medek, J. S. Harwood, L. Frydman, *J. Am. Chem. Soc.* 1995, 117, 12779-12787.
[62] S. P. Brown, S. Wimperis, *J. Magn. Reson.* 1997, 124, 279-285.
[63] S. J. Hwang, C. Fernandez, J. P. Amoureux, J. Cho, S. W. Martin, M. Pruski, *Solid State Nucl. Magn. Reson.* 1997, 8, 109-121.
[64] J. Trebosc, B. Hu, J. P. Amoureux, Z. Gan, *J. Magn. Reson.* 2007, 186, 220-227.
[65] A. Venkatesh, M. P. Hanrahan, A. J. Rossini, *Solid State Nucl. Magn. Reson.* 2017, 84, 171-181.
[66] A. Brinkmann, A. P. M. Kentgens, *J. Am. Chem. Soc.* 2006, 128, 14758-14759.
[67] N. Feng, Q. Wang, A. Zheng, Z. Zhang, J. Fan, S. Bin Liu, J. P. Amoureux, F. Deng, *J. Am. Chem. Soc.* 2013, 135, 1607-1616.
[68] Y. Yu, B. Stevensson, M. Eden, *J. Phys. Chem. Lett.* 2018, 9, 6372-6376.
[69] G. Mali, G. Fink, F. Taulelle, *J. Chem. Phys* 2004, 120, 2835-2845.
[70] Q. Wang, B. Hu, O. Lafon, J. Trebosc, F. Deng, J. P. Amoureux, *J. Magn. Reson.* 2009, 200, 251-260.

Materials and Methods

Materials Synthesis. The materials B/OAC were synthesized via wetness impregnation. Prior to impregnation, 0.5 g activated carbon (Norit Darco 12×40, specific surface area of 600 $m^2 g^{-1}$) was oxidized by stirring the carbon with 100 mL of $HNO_3$ (56% v/v) solution at 60° C. for 24 hours. The mixture was filtered and washed with DI water until the pH was 7. The carbon was dried under static conditions overnight at 110° C. For impregnation, a solution of boric acid ($H_3BO_3$, Sigma Aldrich) in 18 milliQ water was prepared with sufficient water to allow for dissolution of boric acid. Impregnation was performed under stirring and mild heating at 50° C. overnight then the mixture was heated at 110° C. to evaporate excess water. The impregnated sample and excess boric acid was transferred to a tube reactor where it was thermally treated to 600° C. at 1° C. $min^{-1}$ under $N_2$ and held at 600° C. for 3 h. The impregnation was repeated again for a total of two impregnations.

Catalytic Testing. Carbon-supported boron catalysts were tested for their catalytic performance as prepared. Typically, about 200 mg of catalyst were loaded into quartz reactor tube (9 mm diameter) and supported on a bed of quartz wool in the center prior to being loaded into a split tube furnace. A diluent was not used due to the good thermal conductivity of activated carbon. Flow rates of propane (instrument grade, Matheson), oxygen (UHP, Airgas), and nitrogen (UHP, Airgas) were controlled using three mass flow controllers (Bronkhorst) calibrated to each individual gas to allow total flowrates of 40-200 mL $min^{-1}$. Catalysts were heated to reaction temperature under a flow of nitrogen prior to the introduction of the reaction mixture. The reactor effluent was passed through a thermoelectrically-cooled liquid-gas separator to condense formed water before being analyzed by an Inficon Micro GC Fusion equipped with three columns (Rt-Molsieve 5a, Rt-U Bond, and Rt-Alumina Bond/$Na_2SO_4$) with individual thermal conductivity detectors (TCD). The carbon balance of each data point closes within 2%.

Equations:

Alkane Conversion, X (%):

$$X = \frac{\sum F_{carbon\ out}}{F_{alkane\ in}} * 100\%$$

where $F_{carbon\ out}$=of all carbon products from reactor in mol $s^{-1}$ $g_{cat}^{-1}$, $F_{alkane\ in}$flow of all alkane into reactor in mol $s^{-1}$ $g_{cat}^{-1}$ Product Selectivity, S (%):

$$S = \frac{F_{product\ out}}{\sum F_{carbon\ out}} * 100\%$$

where $F_{product\ out}$=flow of product from reactor in mol $s^{-1}$ $g_{cat}^{-1}$, $F_{carbon\ out}$=flow of all carbon products from reactor in mol $s^{-1}$ $g_{cat}^{-1}$ Inverse weight-hour-space-velocity, $WHSV^{-1}$($kg_{cat}$ s $mol_{alkane}^{-1}$):

$$WHSV^{-1} = \frac{M_{cat} * (V/n)_{STP}}{F_{total} * N_{C3H8}}$$

where $M_{cat}$=mass of catalyst loaded in reactor (kg), $(V/n)_{STP}$=24.5 (L/mol) at 298.15 K, (1 atm, R=8.206*$10^{-2}$ L atm $K^{-1}$ $mol^{-1}$), $F_{tot}$=total flow of all inlet gases (L $s^{-1}$), $N_{alkane}$=mol percent alkane in gas feed (mol %)

Raman. In-situ Raman measurements were conducted with a Renishaw InVia Raman spectrometer with a 785 nm excitation laser. All spectra were collected using a 1200 lines $mm^{-1}$ grating and were taking with aa range of 100-2000 $cm^{-1}$ and a dispersion of 1.36565 $cm^{-1}$ $pixel^{-1}$. Each sample was loaded in a high-temperature Linkam CCR1000 cell and heated at 15° C./min under air to 500° C., stopping every 100° C. to record Raman spectra. The spectra are reported without background subtraction.

Infrared Spectroscopy. Diffuse Reflectance Infrared Fourier Transform Spectroscopy (DRIFTS) spectra were recorded by averaging 128 scans with a resolution of 8 $cm^{-1}$. A DiffusIR accessory (PIKE Technologies) was used. The accessory was flushed with dry air at a flow rate of 20 mL $min^{-1}$ and heated at a rate of 10° C. $min^{-1}$ up to a temperature of 500° C.

XPS. XPS measurements were done via Thermo Scientific XPS using a micro-focused monochromated Al K-alpha X-ray source with a flood gun to reduce surface charging. Samples conditions were $10^{-7}$ mbar pressure and room temperature. C 1s, O 1s, and B 1s regions were scanned using a 50 ev pass energy, a 50 ms dwell time, a 400 μm spot size, and a 0.2 ev energy step size. The number of scans per element was adjusted to improved signal-to-noise. All surface compositions, and peak integration/deconvolution were done via Avantage (Thermo Scientific) Software package.

ICP. Elemental analysis was performed by inductively coupled plasma-optical emission spectroscopy (ICP-OES) measurements on an Agilent 5110 VDV at the Water Science and Engineering Laboratory at the University of Wisconsin-Madison. Prior to analysis, 12-20 mg of B/OAC sample was leached using three consecutive acid treatments of 5 mL of 100% aqua regia. Leached samples were diluted by a factor of 20 using nano-pure $H_2O$. Samples were measured using both external standard curve and standard addition methods. The external standards were made using diluted aqua regia that was used to leach a bare carbon support. This treated aqua regia ensured a closer matrix match to the samples. Standard addition was done using a 6-point curve including the diluted neat sample. Three B wavelength were averaged to determine the concentrations, 208.956 nm, 249.678 nm, and 249.772 nm. All samples were measured in triplicate to ensure accuracy. Both methods returned the same results within the error margin.

Water Isotherm. $H_2O$ pulse adsorption was performed on a Micromeritics Autochem II 2920 instrument. For this experiment, between 100 to 200 mg of sample was calcined at 773 K (10 K/min) for 1 h under flowing air and subsequently cooled (10 K/min) to room temperature under He (all flowrates were 50 mL/min unless stated otherwise). The sample was then pulsed with He saturated with water vapor at 40° C. with a 5 mL STP loop until no more uptake of water was observed. The water pulsing end point was denoted by the consecutive appearance of constant area peaks as monitored by a TCD detector. Afterwards, the total volume of water adsorbed per sample was calculated by determining the amount of unadsorbed water and subtracting this amount to the total amount of water pulsed.

Differential Scanning calorimetry. Differential scanning calorimetry experiments were conducted on a TGA/DSC1 system (Mettler-Toledo). Samples were heated in 70 uL Alumina crucibles covered with a lid with a pinhole using the above heating method in the figure (bottom right). Two glass transition temperatures (Tg) for B/OAC were determined via the midpoint method at 61.18° C. and 80.36° C. Both B/OAC and borosilicate show major inflection points at 390.2° C. and 399.09° C. respectively.

Solid-State NMR Spectroscopy. All solid-state NMR spectroscopy experiments were conducted on a 14.1 T ($n_0(^1H)$=600 MHz) Bruker wide-bore magnet spectrometer equipped with a Bruker Avance II console and a 2.5 mm HXY magic-angle spinning (MAS) NMR probe configured in double resonance mode. A $^1H$ high-pass ($n_0(^1H)$=600 MHz) or $^{31}P$ low-pass ($n_0(^{31}P)$=243 MHz) filter was applied to the $^1H$ or X preamplifiers, respectively, to better isolate the two channels. Fresh and spent B/OAC catalysts were center packed between powdered Teflon into 2.5 mm NMR rotors in a $N_2$ filled glovebox and the rotors were spun with $N_2$ gas to minimize sample hydration/air exposure. The magnetic field strength was immediately calibrated following removal of each sample to $^1H$ chemical shifts of neat tetramethylsilane with adamantane as a secondary chemical shift reference ($d_{iso}(^1H)$=1.82 ppm). $^{11}B$ chemical shifts were referenced using previously reported IUPAC relative NMR frequencies ($BF_3 \cdot Et_2O$).[1] Bruker topspin 3.6.1 was used to process all NMR spectra. Analytical simulations of the $^{11}B$ single-pulse and MQMAS spectra were performed using the ssNake NMR software.[2]

All experimental parameters (number of scans, recycle delay, $t_1$ TD points, $t_1$ dwell ($Dt_1$), dipolar recoupling durations and total experimental times) are given in Table 3. $^1H$ and $^{11}B$ longitudinal relaxation constants ($T_1$) were measured using a saturation recovery experiment. $^1H$ radio frequency (RF) pulses were directly calibrated on the fresh and spent B/OAC materials. All $^1H$p/2 pulses were 2.5 ms in duration, corresponding to a 100 kHz RF field. Direct excitation single-pulse $^{11}B$ NMR experiments were recorded with a repetition delay of greater than 5×$T_1$ and a 10° tip angle (1.67 ms in duration, corresponding to a 8.3 kHz RF field and 16.6 kHz central-transition nutation frequency) to ensure the spectra were quantitative. The same experiment was performed on a rotor filled entirely with adamantane to subtract out $^{11}B$ NMR signals coming from the stator and other probe components. 100 kHz RF field of SPINA1-64 $^{1}H$ heteronuclear decoupling was performed during the acquisition of all $^{11}B$ spectra)

TABLE 3

Experimental solid-state NMR spectroscopy parametrs.

| FIG. | Experiment | Recycle delay (s) | # of Scans | $t_1$ TD points | $\Delta t_1$ (μs) | Duration of Recoupling (ms) | Total Experimental Time (h) |
|---|---|---|---|---|---|---|---|
| 4a (fresh) | $^{11}B$ Single-Pulse | 10[a] | 128 | — | — | — | 0.36 |
| 4a (spent) | $^{11}B$ Single-Pulse | 20[a] | 128 | — | — | — | 0.72 |
| 4c (fresh) | 2D $^{11}B$ MQMAS | 1.95 | 192 | 84 | 40 | — | 8.8 |
| 4c (spent) | 2D $^{11}B$ MQMAS | 3.0 | 192 | 84 | 40 | — | 13.5 |
| 5a (blue) | 2D $^{11}B\rightarrow{}^{1}H$ D-RINEPT | 1.5 | 32 | 74 | 40 | 0.64 | 1.1 |
| 5a (red) | 2D $^{11}B\rightarrow{}^{1}H$ D-RINEPT | 1.5 | 32 | 74 | 40 | 2.24 | 1.1 |
| S13 (blue) | 2D $^{11}B\rightarrow{}^{1}H$ D-RINEPT | 3.9 | 64 | 74 | 40 | 0.64 | 5.3 |
| S13 (red) | 2D $^{11}B\rightarrow{}^{1}H$ D-RINEPT | 3.9 | 64 | 74 | 40 | 2.24 | 5.3 |
| S15a (blue) | 2D $^{11}B$ DQ-SQ | 1.95 | 32 | 74 | 40 | 0.32 | 1.3 |
| S15a (red) | 2D $^{11}B$ DQ-SQ | 1.95 | 32 | 74 | 40 | 1.6 | 1.3 |
| S15b (blue) | 2D $^{11}B$ DQ-SQ | 3.9 | 32 | 74 | 40 | 0.32 | 2.6 |
| S15b (red) | 2D $^{11}B$ DQ-SQ | 3.9 | 32 | 74 | 40 | 1.6 | 2.6 |

[a]Recycle delay > 5 × $T_1$.

2D split-$t_1$ triple-quantum multiple-quantum MAS (3Q-MQMAS) experiments were recorded with previously described pulse sequences.[4-6] 0Q→3Q excitation and 3Q→1Q reconversion pulse lengths were 4.0 and 1.6 ms in duration, respectively. 100 kHz RF field of SPINA1-64 $^{1}H$ heteronuclear decoupling was performed throughout the entire experiment. The $^{11}B$ isotropic dimension spectral width was scaled by $(2.125)^{-1}$ to account for faster chemical shift evolution under 3Q coherence. The $^{11}B$ isotropic dimension was calibrated from an $^{11}B$ MQMAS of a sodium borate glass with identical transmitter offsets. The isotropic dimension of the $^{11}B$ MQMAS of the sodium borate glass was referenced by setting the 4-coordinate $BO_4$ signal to the same shift observed in the direct dimension since the $C_Q<0.5$ MHz (thus QIS is negligible). 2D $^{11}B\rightarrow{}^{1}H$ D-RINEPT heteronuclear correlation experiments were performed with previously described pulse sequences.[7,8] The symmetry based $$SR4_1^2$$

heteronuclear dipolar recoupling scheme was applied to the $^{1}H$ spins (50 kHz RF field) to re-introduce $^{1}H$—$^{11}B$ dipolar couplings.[9] 100 kHz RF field of SPINA1-64 $^{1}H$ heteronuclear decoupling was performed during the indirect acquisition of $^{11}B$. Central-transition (CT) selective $^{11}B$ p/2 and p pulse lengths were 15 and 30 ms in duration, respectively, corresponding to a 8.3 kHz RF field and 16.6 kHz CT nutation frequency. 2D $^{11}B$ DQ-SQ homonuclear correlation experiments were performed with previously described NMR pulse sequences.[10-12] A CT selective p pulse was applied during h evolution to ensure only CT DQ coherence between two $^{11}B$ spins were selected during phase cycling.[10] The bracket $$BR2_2^1$$

homonuclear dipolar recoupling scheme was used to generate DQ coherence directly from Z-magnetization.[12] Each p pulse in the $$BR2_2^1$$

homonuclear dipolar recoupling block was 40 ms in duration, corresponding to a 6.25 kHz RF field and 12.5 kHz CT nutation frequency. 100 kHz RF field of SPINA1-64 $^{1}H$ heteronuclear decoupling was performed throughout the entire experiment. A schematic illustration of all pulses sequences is given in FIG. 22.

Density Functional Theory Calculations. Period plane-wave density functional theory (DFT) calculations were performed in CASTEP[13] (version 2017 R2) with the gauge including projected augmented-wave (GIPAW) approach[14]. Plane-wave DFT geometry optimizations and NMR calculations utilized the Generalized Gradient Approximation (GGA) with the Perdew-Burke-Ernzerhof exchange-correlation functional,[15] Tkatchenko-Scheffler (TS) dispersion corrections[16], On-the-Fly ultrasoft pseudopotential[17,18] and zeroth-order regular approximation (ZORA) relativistic treatment.[19] A 0.07 $Å^{-1}$ k-point spacing and 630 eV kinetic energy cutoff was used for all calculations.

The phenyl borate systems were constructed in the open-source Avogadro molecular builder and visualization tool application prior to all DFT calculations.[19] For DFT, the structure was located in the middle of a 20 Å×20 Å×20 Å lattice that was surrounded by vacuum to ensure completer isolation between multiple species as the calculations were periodic (see CIF files). The calculated $^{11}B$ shielding (s) values were converted to isotropic chemical shift (disc) using a previously published calibration curve (experimentally determined shifts versus DFT calculated shielding values for samples with known crystal structures) utilizing identical DFT parameters.[20] The calculated $^{11}B$ $C_Q$ values were corrected via a previously published calibration curve, similar to that for converting shielding to shift.[20]

References in the Materials and Methods

[1] R. K. Harris, E. D. Becker, S. M. Cabral de Menezes, R. Goodfellow, P. Granger, *Solid State Nucl. Magn. Reson.* 2002, 22, 458-483.

[2] S. G. J. van Meerten, W. M. J. Franssen, A. P. M. Kentgens, *J. Magn. Reson.* 2019, 301, 56-66.

[3] B. M. Fung, A. K. Khitrin, K. Ermolaev, *J. Magn. Reson.* 2000, 142, 97-101.

[4] S. P. Brown, S. Wimperis, *J. Magn. Reson.* 1997, 124, 279-285.

[5] S. J. Hwang, C. Fernandez, J. P. Amoureux, J. Cho, S. W. Martin, M. Pruski, *Solid State Nucl. Magn. Reson.* 1997, 8, 109-121.

[6] A. Medek, J. S. Harwood, L. Frydman, *J. Am. Chem. Soc.* 1995, 117, 12779-12787.

[7] J. Trebosc, B. Hu, J. P. Amoureux, Z. Gan, *J. Magn. Reson.* 2007, 186, 220-227.

[8] A. Venkatesh, M. P. Hanrahan, A. J. Rossini, *Solid State Nucl. Magn. Reson.* 2017, 84, 171-181.

[9] A. Brinkmann, A. P. M. Kentgens, *J. Am. Chem. Soc.* 2006, 128, 14758-14759.

[10] G. Mali, G. Fink, F. Taulelle, *J. Chem. Phys* 2004, 120, 2835-2845.

[11] M. Eden, D. Zhou, J. Yu, *Chem. Phys. Lett.* 2006, 431, 397-403.

[12] Q. Wang, B. Hu, O. Lafon, J. Trebosc, F. Deng, J. P. Amoureux, *J. Magn. Reson.* 2009, 200, 251-260.

[13] S. J. Clark, M. D. Segall, C. J. Pickard, P. J. Hasnip, M. I. J. Probert, K. Refson, M. C. Payne, *Z. Krist.* 2005, 220, 567-570.

[14] A. M. Love, B. Thomas, S. E. Specht, M. P. Hanrahan, J. M. Venegas, S. P. Burt, J. T. Grant, M. C. Cendej as, W. P. McDermott, A. J. Rossini, et al., *J. Am. Chem. Soc.* 2019, 141, 182-190.

[15] J. P. Perdew, K. Burke, M. Ernzerhof, *Phys. Rev. Lett.* 1996, 77, 3865-3868.

[16] A. Tkatchenko, M. Scheffler, *Phys. Rev. Lett.* 2009, 102, 073005.

[17] J. R. Yates, C. J. Pickard, F. Mauri, *Phys. Rev. B.* 2007, 76, 1-11.

[18] C. J. Pickard, F. Mauri, *Phys. Rev. B.* 2001, 63, 2451011-2451013.

[19] T. F. G. Green, J. R. Yates, *J. Chem. Phys* 2014, 140, 234106.

[20] R. W. Dorn, M. J. Ryan, T.-H. Kim, T. W. Goh, A. Venkatesh, P. M. Heintz, L. Zhou, W. Huang, A. J. Rossini, *Chem. Mater.* 2020, 32, 3109-3121.

Example 2: Unsuccessful Boron on Carbon Catalyst Preparations—Oxidized Carbon Required In this example, we demonstrate that boron on carbon compositions made using amorphous carbon that is not oxidized are not viable catalysts. In each case, the composition was unstable and the entirety of the composition combusted to $CO_2$ during catalysis. Combustion of the resulting structure indicates the instability of the material under ODH reaction conditions.

In a first attempt at making such a composition, incipient wetness impregnation (IWI) of dehydrated Norit Darco 12×40 activated carbon (NDC) was performed with triisopropyl borate. The NDC was not oxidized before impregnation, and the entirety of the resulting structure combusted to $CO_2$ during catalysis.

The NDC was crushed up and thermally treated at 120° C. in an ambient catalyst oven overnight with triisopropyl borate in a purge box under $N_2$ flow. Calcination was then performed at 600° C. in a muffle furnace.

In a second attempt, wetness impregnation of dehydrated Norit Darco 12×40 was performed with boric acid solution. Again, the NDC was not oxidized before impregnation, and the resulting structure burned during catalysis.

NDC was crushed up and thermally treated at 120° C. in an ambient catalyst oven overnight. Subsequently, wetness impregnation with boric acid solution was conducted overnight. The NDC was stirred in solution on a hot plate at 80° C. and the solution and carbon were then dried in a catalyst oven until the water evaporated. Calcination was then performed at 600° C. in a muffle furnace. We also attempted a post-impregnation thermal treatment at 600° C. under $N_2$.

In a third attempt, wetness impregnation of reduced Norit Darco 12×40 was performed with boric acid solution. Once again, the resulting structure burned during catalysis.

The NDC was dispersed in DI water and adjusted to pH 9-10 using $NaCO_3$. $NaBH_4$ was added, and the mixture was heated at 80° C. for 1 hr on a hot plate. The mixture was then filtered and washed with DI water, and dried overnight in a catalyst oven (120° C.).

Wetness impregnation with boric acid solution was conducted overnight. The NDC was stirred in solution on a hot plate at 80° C., then the solution and carbon were dried in a catalyst oven until water evaporated. The resulting composition was thermally treated at 600° C. under $N_2$.

This example demonstrates that using oxidized amorphous carbon is essential to the thermal stability of the disclosed catalysts.

We claim:

1. A catalytic material comprising oxidized amorphous carbon impregnated with boron, wherein the catalytic material comprises a plurality of 3-coordinate boron species bound to the oxidized amorphous carbon, wherein the plurality of 3-coordinate boron species comprise $B(OB)(OH)_2$, $B(OB)_2(OH)$, $B(OB)_3$, $B(OB)_2(OC)$, $B(OB)(OC)_2$, and $B(OC)_3$.

2. The catalytic material of claim 1, wherein a majority of the plurality of 3-coordinate boron species are clustered.

3. The catalytic material of claim 2, wherein between 60 and 90% of the plurality of 3-coordinate boron species are $B(OB)(OH)_2$, $B(OB)_2(OH)$, and $B(OB)_3$.

4. The catalytic material of claim 3, wherein between 40 and 70% of plurality of 3-coordinate species are $B(OB)(OH)_2$ and the $B(OB)_2(OH)$.

5. The catalytic material of claim 1, wherein the catalytic material comprises from 25 wt % to 40 wt % boron, based on the total weight of the catalytic material;

wherein the catalytic material comprises a complete layer of boron covering the oxidized amorphous carbon;

wherein the boron is impregnated onto the surface of the oxidized amorphous carbon;

wherein the oxidized amorphous carbon comprises, at its unimpregnated surface, one or more moieties selected from the group consisting of a carboxyl, a phenolic hydroxyl, a carbonyl, an anhydride, and a —C—O—;

wherein the oxidized amorphous carbon is oxidized activated carbon;

wherein the catalytic material is capable of catalyzing oxidative dehydrogenation (ODH) of an alkane or an alkyl group;

wherein the catalytic material has an ODH induction period of less than 12 hours;

wherein the catalytic material is thermally stable; or any combination thereof.

6. A method of making one or more desired chemical products, comprising contacting a heterogeneous catalyst comprising the catalytic material of claim 1 with oxygen and one or more liquid or gaseous reactants, whereby the heterogeneous catalyst catalyzes the oxidative dehydrogenation of the one or more liquid or gaseous reactants to form the one or more desired chemical products.

7. The method of claim 6, wherein:

(a) the one or more liquid or gaseous reactants comprise an alkane or a hydrocarbon comprising an alkyl group; and (b) the one or more desired chemical products comprise one or more olefins or one or more hydrocarbons comprising an alkenyl group.

8. The method of claim 7, wherein the one or more liquid or gaseous reactants comprise a $C_2$-$C_5$ alkane or $C_2$-$C_5$ alkylbenzene.

9. The method of claim 8, wherein the one or more liquid or gaseous reactants comprise ethane, propane, n-butane, isobutane, or any combination thereof.

10. The method of claim 8, wherein the one or more liquid or gaseous reactants comprise ethylbenzene.

11. The method of claim 6, wherein the contacting step occurs at a temperature of from 400° C. to 800° C.;

wherein the oxygen and one or more liquid or gaseous reactants are in a reactant stream that is contacted with the heterogeneous catalyst;

wherein the heterogeneous catalyst has an induction period of less than 12 hours;

wherein the heterogeneous catalyst has a selectivity for the one or more desired chemical products of 70% or greater; or any combination thereof.

12. A method of producing a catalytic material, the method comprising impregnating oxidized amorphous carbon with boron.

13. The method of claim 12, wherein impregnating the surface of the oxidized amorphous carbon with boron is performed by contacting the oxidized amorphous carbon with boric acid.

14. The method of claim 12, further comprising oxidizing amorphous carbon to produce the oxidized amorphous carbon, calcining the impregnated oxidized amorphous carbon, thermally treating the impregnated oxidized amorphous carbon; or any combination thereof.

15. The method of claim 14, wherein the method comprises oxidizing amorphous carbon to produce the oxidized amorphous carbon by contacting amorphous carbon with an oxidizing agent under conditions suitable for producing the oxidized amorphous carbon.

16. The method of claim 15, wherein the oxidizing agent is nitric acid, ozone, or hydrogen peroxide.

17. The method of claim 14, wherein the method comprises calcining the impregnated oxidized amorphous carbon.

18. The method of claim 14, wherein the method comprises thermally treating the impregnated oxidized amorphous carbon by heating the impregnated oxidized amorphous carbon under an inert atmosphere.

19. The method of claim 14, wherein the method comprises oxidizing amorphous carbon to produce the oxidized amorphous carbon by contacting amorphous carbon with an oxidizing agent under conditions suitable for producing the oxidized amorphous carbon, calcining the impregnated oxidized amorphous carbon, and thermally treating the impregnated oxidized amorphous carbon by heating the calcined, impregnated oxidized amorphous carbon under an inert atmosphere.

* * * * *